US009150494B2

(12) United States Patent
Tonkovich et al.

(10) Patent No.: US 9,150,494 B2
(45) Date of Patent: Oct. 6, 2015

(54) PROCESS USING MICROCHANNEL TECHNOLOGY FOR CONDUCTING ALKYLATION OR ACYLATION REACTION

(75) Inventors: Anna Lee Tonkovich, Dublin, OH (US); Steven T. Perry, Galloway, OH (US); Timothy J. LaPlante, Columbus, OH (US); Kai Tod Paul Jarosch, Bexley, OH (US); Thomas P. Hickey, Dublin, OH (US); Sean Patrick Fitzgerald, Columbus, OH (US); Dongming Qiu, Bothell, WA (US); Ravi Arora, New Albany, OH (US); Timothy J. Sullivan, Dublin, OH (US); Paul Neagle, Westerville, OH (US)

(73) Assignee: Velocys, Inc., Plain City, OH (US)

( * ) Notice: Subject to any disclaimer, the term of this patent is extended or adjusted under 35 U.S.C. 154(b) by 1589 days.

(21) Appl. No.: 11/271,154

(22) Filed: Nov. 11, 2005

(65) Prior Publication Data
US 2006/0129015 A1    Jun. 15, 2006

Related U.S. Application Data

(60) Provisional application No. 60/627,269, filed on Nov. 12, 2004, provisional application No. 60/697,900, filed on Jul. 8, 2005, provisional application No. 60/727,126, filed on Oct. 13, 2005, provisional application No. 60/731,596, filed on Oct. 27, 2005.

(51) Int. Cl.
*C07C 2/56* (2006.01)
*C07C 209/68* (2006.01)
(Continued)

(52) U.S. Cl.
CPC ............. *C07C 209/68* (2013.01); *B01F 5/0475* (2013.01); *B01F 13/0059* (2013.01);
(Continued)

(58) Field of Classification Search
USPC .......................... 585/709, 721–729
See application file for complete search history.

(56) References Cited

U.S. PATENT DOCUMENTS

| 4,392,362 A | 7/1983 | Little ........................... 62/514 |
| 4,516,632 A | 5/1985 | Swift et al. ................... 165/167 |

(Continued)

FOREIGN PATENT DOCUMENTS

| CA | 2247662 | 3/1999 |
| DE | 199 35 691 A1 | 7/1999 |

(Continued)

OTHER PUBLICATIONS

Kestenbaum; "Synthesis of ethylene oxide in a microreaction system"; *Microreaction Technology: Industrial Prospects*; IMRET 3: Proceedings of the Third International Converence on Microreaction Technology. (2000).

(Continued)

*Primary Examiner* — Randy Boyer
(74) *Attorney, Agent, or Firm* — Renner, Otto, Boisselle & Sklar, LLP

(57) ABSTRACT

The disclosed invention relates to a process, comprising: flowing a first reactant feed stream comprising a reactant substrate and a second reactant feed stream comprising an alkylating agent, an acylating agent or a mixture thereof, in a process microchannel in contact with each other to form a product comprising at least one alkylation product, at least one acylation product, or a mixture thereof; transferring heat from the process microchannel to a heat sink; and removing the product from the process microchannel.

105 Claims, 19 Drawing Sheets

(51) Int. Cl.
*B01F 5/04* (2006.01)
*B01F 13/00* (2006.01)
*B01J 19/00* (2006.01)
*C07C 2/66* (2006.01)
*C07C 2/70* (2006.01)
*C07C 37/14* (2006.01)
*B01J 29/40* (2006.01)
*B01J 37/02* (2006.01)
*B01J 38/10* (2006.01)

(52) U.S. Cl.
CPC ............ *B01J19/0093* (2013.01); *C07C 2/66* (2013.01); *C07C 2/70* (2013.01); *C07C 37/14* (2013.01); *B01J 29/40* (2013.01); *B01J 37/0225* (2013.01); *B01J 38/10* (2013.01); *B01J 2219/0086* (2013.01); *B01J 2219/00783* (2013.01); *B01J 2219/00822* (2013.01); *B01J 2219/00826* (2013.01); *B01J 2219/00828* (2013.01); *B01J 2219/00831* (2013.01); *B01J 2219/00833* (2013.01); *B01J 2219/00835* (2013.01); *B01J 2219/00837* (2013.01); *B01J 2219/00844* (2013.01); *B01J 2219/00873* (2013.01); *B01J 2219/00889* (2013.01); *B01J 2219/00891* (2013.01); *B01J 2219/00905* (2013.01); *C07C 2529/40* (2013.01)

(56) References Cited

U.S. PATENT DOCUMENTS

| | | | | |
|---|---|---|---|---|
| 4,708,753 | A | 11/1987 | Forsberg | |
| 5,185,469 | A * | 2/1993 | Lindley et al. | 568/319 |
| 5,309,637 | A | 5/1994 | Moriarty | 29/890.054 |
| 5,317,805 | A | 6/1994 | Hoopman et al. | 29/890.03 |
| 5,430,211 | A | 7/1995 | Pogue et al. | 585/323 |
| 5,597,773 | A | 1/1997 | Evans et al. | 502/348 |
| 5,611,214 | A | 3/1997 | Wegeng et al. | 62/498 |
| 5,689,966 | A | 11/1997 | Zess et al. | 62/238.6 |
| 5,727,618 | A | 3/1998 | Mundinger et al. | 165/80.4 |
| 5,811,062 | A | 9/1998 | Wegeng et al. | 422/129 |
| 5,858,314 | A | 1/1999 | Hsu et al. | 422/211 |
| 5,997,826 | A | 12/1999 | Lodeng et al. | 422/190 |
| 6,056,932 | A | 5/2000 | von Hippel et al. | 423/376 |
| 6,096,939 | A * | 8/2000 | Benazzi et al. | 585/730 |
| 6,126,723 | A | 10/2000 | Drost et al. | 96/4 |
| 6,129,973 | A | 10/2000 | Martin et al. | 428/166 |
| 6,159,358 | A | 12/2000 | Mulvaney, III et al. | 423/376 |
| 6,174,972 | B1 | 1/2001 | Daire | 526/144 |
| 6,192,596 | B1 * | 2/2001 | Bennett et al. | 422/129 |
| 6,200,536 | B1 | 3/2001 | Tonkovich et al. | 422/177 |
| 6,216,343 | B1 | 4/2001 | Leland et al. | 29/890.032 |
| 6,220,497 | B1 | 4/2001 | Benz et al. | 228/118 |
| 6,230,408 | B1 | 5/2001 | Ehrfeld et al. | 29/890.039 |
| 6,235,959 | B1 | 5/2001 | Hirschauer et al. | 585/709 |
| 6,255,538 | B1 | 7/2001 | Dougherty et al. | 568/766 |
| 6,284,217 | B1 | 9/2001 | Wang et al. | 423/651 |
| 6,303,840 | B1 | 10/2001 | Poliakoff et al. | 585/459 |
| 6,313,393 | B1 | 11/2001 | Drost | 136/201 |
| 6,352,577 | B1 | 3/2002 | Martin et al. | 96/4 |
| 6,381,846 | B2 | 5/2002 | Insley et al. | 29/890.039 |
| 6,395,945 | B1 | 5/2002 | Randolph | 585/332 |
| 6,409,072 | B1 | 6/2002 | Breuer et al. | 228/111.5 |
| 6,415,860 | B1 | 7/2002 | Kelly et al. | 165/748 |
| 6,440,895 | B1 | 8/2002 | Tonkovich et al. | 502/439 |
| 6,451,864 | B1 | 9/2002 | Wang et al. | 518/715 |
| 6,479,428 | B1 | 11/2002 | Tonkovich et al. | 502/302 |
| 6,479,721 | B1 | 11/2002 | Gajda et al. | 585/467 |
| 6,488,838 | B1 | 12/2002 | Tonkovich et al. | 208/108 |
| 6,490,812 | B1 | 12/2002 | Bennett et al. | 34/433 |
| 6,491,880 | B1 | 12/2002 | Wang et al. | 422/211 |
| 6,492,571 | B1 | 12/2002 | He et al. | 585/710 |
| 6,500,309 | B1 | 12/2002 | Tung | 202/153 |
| 6,503,298 | B1 | 1/2003 | Monzyk et al. | 95/96 |
| 6,508,862 | B1 | 1/2003 | Tonkovich et al. | 95/106 |
| 6,533,840 | B2 | 3/2003 | Martin et al. | 95/45 |
| 6,540,975 | B2 | 4/2003 | Tonkovich et al. | 423/659 |
| 6,558,634 | B1 | 5/2003 | Wang et al. | 422/173 |
| 6,607,678 | B2 | 8/2003 | Wang et al. | 252/373 |
| 6,616,909 | B1 | 9/2003 | Tonkovich et al. | 423/648.1 |
| 6,622,519 | B1 | 9/2003 | Mathias et al. | 62/611 |
| 6,642,425 | B2 | 11/2003 | Winder et al. | 585/323 |
| 6,652,627 | B1 | 11/2003 | Tonkovich et al. | 95/104 |
| 6,660,237 | B2 | 12/2003 | Wang et al. | 422/222 |
| 6,666,909 | B1 | 12/2003 | TeGrotenhuis et al. | 95/273 |
| 6,675,875 | B1 | 1/2004 | Vafai et al. | 165/80.4 |
| 6,680,044 | B1 | 1/2004 | Tonkovich et al. | 423/652 |
| 6,713,036 | B1 | 3/2004 | Vanden Bussche et al. | 423/584 |
| 6,723,877 | B1 | 4/2004 | Maliszewskyj et al. | 564/215 |
| 6,734,137 | B2 | 5/2004 | Wang et al. | 502/328 |
| 6,746,651 | B1 | 6/2004 | Ponzo et al. | 422/220 |
| 6,746,819 | B1 | 6/2004 | Schmitz et al. | 430/272.1 |
| 6,747,178 | B1 | 6/2004 | Harston et al. | 570/175 |
| 6,749,814 | B1 | 6/2004 | Bergh et al. | 422/130 |
| 6,749,817 | B1 | 6/2004 | Mulvaney, III | 422/200 |
| 6,755,211 | B1 | 6/2004 | O'Connor et al. | 137/554 |
| 6,762,149 | B2 | 7/2004 | Tonkovich et al. | 502/439 |
| 6,769,444 | B2 | 8/2004 | Guzman et al. | 137/15.01 |
| 6,773,684 | B2 | 8/2004 | Lesieur et al. | 422/198 |
| 6,814,781 | B2 | 11/2004 | Tonkovich et al. | 95/90 |
| 6,851,171 | B2 | 2/2005 | Schmitt | 29/469 |
| 6,955,738 | B2 | 10/2005 | Derand et al. | 156/272.6 |
| 6,969,746 | B2 | 11/2005 | Krull et al. | 526/64 |
| 7,304,198 | B2 | 12/2007 | Wang et al. | |
| 7,307,104 | B2 * | 12/2007 | Qiu et al. | 516/54 |
| 2001/0018140 | A1 | 8/2001 | Hermann et al. | 429/20 |
| 2002/0028164 | A1 | 3/2002 | Schutte et al. | 422/198 |
| 2002/0144600 | A1 | 10/2002 | TeGrotenhuis et al. | 95/273 |
| 2002/0192118 | A1 | 12/2002 | Zech et al. | 422/99 |
| 2002/0198383 | A1 | 12/2002 | Trost et al. | 546/5 |
| 2002/0198422 | A1 | 12/2002 | Broekhoven et al. | 585/446 |
| 2003/0007904 | A1 | 1/2003 | Tonkovich et al. | 422/180 |
| 2003/0023124 | A1 | 1/2003 | De Stefanis et al. | 585/446 |
| 2003/0045747 | A1 | 3/2003 | Wurziger et al. | 562/418 |
| 2003/0069420 | A1 | 4/2003 | Koch et al. | 544/69 |
| 2003/0100792 | A1 | 5/2003 | Koch et al. | 562/7 |
| 2003/0116503 | A1 | 6/2003 | Wang et al. | 210/660 |
| 2003/0124038 | A1 | 7/2003 | Moritz et al. | 422/211 |
| 2003/0180216 | A1 * | 9/2003 | TeGrotenhuis et al. | 422/211 |
| 2003/0219903 | A1 | 11/2003 | Wang et al. | 436/37 |
| 2004/0034111 | A1 | 2/2004 | Tonkovich et al. | 518/726 |
| 2004/0055329 | A1 | 3/2004 | Mathias et al. | 62/611 |
| 2004/0104010 | A1 | 6/2004 | Kenny et al. | 165/80.4 |
| 2004/0123626 | A1 | 7/2004 | Caze et al. | 65/17.2 |
| 2004/0125689 | A1 | 7/2004 | Ehrfeld et al. | 366/165.1 |
| 2004/0130057 | A1 | 7/2004 | Mehrabi et al. | 264/171.13 |
| 2004/0131345 | A1 | 7/2004 | Kylberg et al. | 392/465 |
| 2004/0131829 | A1 | 7/2004 | Joseph et al. | 428/166 |
| 2004/0136902 | A1 | 7/2004 | Plath et al. | 423/651 |
| 2004/0141893 | A1 | 7/2004 | Martin | 422/198 |
| 2004/0143059 | A1 | 7/2004 | Cabrera | 524/800 |
| 2004/0144421 | A1 | 7/2004 | Parce et al. | 137/14 |
| 2004/0156762 | A1 | 8/2004 | Schuppich et al. | 422/191 |
| 2004/0188326 | A1 | 9/2004 | Tonkovich et al. | 208/139 |
| 2004/0220434 | A1 | 11/2004 | Brophy et al. | 568/959 |
| 2004/0228781 | A1 | 11/2004 | Tonkovich et al. | 422/222 |
| 2004/0228882 | A1 | 11/2004 | Qiu et al. | 424/400 |
| 2004/0229752 | A1 | 11/2004 | Long et al. | 502/303 |
| 2004/0234566 | A1 | 11/2004 | Qiu et al. | 424/401 |
| 2005/0045030 | A1 | 3/2005 | Tonkovich et al. | 95/90 |
| 2005/0163701 | A1 | 7/2005 | Tonkovich et al. | 423/584 |
| 2005/0165121 | A1 | 7/2005 | Wang et al. | 518/726 |
| 2005/0176832 | A1 | 8/2005 | Tonkovich et al. | 518/726 |
| 2005/0232076 | A1 | 10/2005 | Yang et al. | 366/336 |
| 2005/0256358 | A1 | 11/2005 | Wang et al. | 585/709 |

FOREIGN PATENT DOCUMENTS

| DE | 102004007561 B3 | 10/2005 |
|---|---|---|
| EP | 0 885 086 B1 | 8/2001 |
| EP | 1 311 341 B1 | 8/2001 |
| EP | 0 904 608 B1 | 12/2001 |
| EP | 1 232 790 A1 | 8/2002 |

(56) References Cited

FOREIGN PATENT DOCUMENTS

| | | |
|---|---|---|
| EP | 1 382 382 A1 | 7/2003 |
| EP | 1 362 634 A1 | 11/2003 |
| EP | 1 056 694 B1 | 7/2004 |
| WO | 97/32687 | 9/1997 |
| WO | 98/55812 | 12/1998 |
| WO | 99/48805 | 9/1999 |
| WO | 00/06295 | 10/2000 |
| WO | 01/10773 A1 | 2/2001 |
| WO | 01/12312 A2 | 2/2001 |
| WO | 01/09064 A1 | 8/2001 |
| WO | 01/54807 A1 | 8/2001 |
| WO | 01/95237 A2 | 12/2001 |
| WO | 02/14854 A1 | 2/2002 |
| WO | 02/064248 A2 | 8/2002 |
| WO | 03/078052 A1 | 9/2003 |
| WO | 03/106386 A2 | 12/2003 |
| WO | 2004/016347 A2 | 2/2004 |
| WO | 2004/103539 A2 | 2/2004 |
| WO | 2004/101138 A1 | 5/2004 |
| WO | 2004/037399 A2 | 6/2004 |
| WO | 2004/037418 A1 | 6/2004 |
| WO | 2004/037418 A2 | 6/2004 |
| WO | 2004/045760 | 6/2004 |
| WO | 2004/050799 | 6/2004 |
| WO | 2004/052518 | 6/2004 |
| WO | 2004/052530 | 6/2004 |
| WO | 2004/052941 | 6/2004 |
| WO | 2004/054013 | 6/2004 |
| WO | 2004/054696 | 7/2004 |
| WO | 2004/062790 | 7/2004 |
| WO | 2004/062791 | 7/2004 |
| WO | 2004/062792 | 7/2004 |
| WO | 2004/067160 | 8/2004 |
| WO | 2004/067444 | 8/2004 |
| WO | 2004/067492 | 8/2004 |
| WO | 2004/067708 | 8/2004 |
| WO | 2004/091771 A1 | 10/2004 |
| WO | 2004/099113 A1 | 11/2004 |
| WO | 2005/003025 A2 | 1/2005 |
| WO | 2005/104323 A2 | 3/2005 |
| WO | 2005/060658 A1 | 7/2005 |

OTHER PUBLICATIONS

Besser, Ronald S. "New Directions in Reactor Design Through Miniaturization". Sep. 13, 2002, Tulane Engineering Forum.

Gohring et al.; "Gas Phase Reactions in Ceramic Microreactors"; IMERT 6, Mar. 10-14, 2002, New Orleans, USA, AIChE Conference Proceedings 55-60.

Hsing et al.; "Simulation of Microchannel Chemical Reactors for Heterogeneous Partial Oxidation Reactions"; Chemical Engineering Science 55 (2000) 3-13.

Matlosz et al.; "Microreactors as Tools in Chemical Research"; Microreaction Technology; IMRET 5: Proceedings of the Fifth International Conference on Microreaction Technology. (May 27-30, 2001).

Srinivasn et al.; "Micromachined Reactors for Catalytic Partial Oxidation Reactions"; AIChE Journal; Nov. 1997; vol. 43, No. 11; pp. 3059-3069.

TeGrotenhuis et al.; Optimizing Microchannel Reactors by Trading-Off Equilibrium and Reaction Kinetics through Temperature Management; Prepared for presentation at IMRET 6—6$^{th}$ International Conference on Microreaction Technology; Mar. 10-14, 2002.

Wegeng et al.; "Compact Fuel Processors for Fuel Cell Powered Automobiles Based on Microchannel Technology"; Fuel Cells Bulletin No. 28; pp. 8-13.

Rostami et al.; "Flow and Heat Transfer for Gas Flowing in Microchannels: a Review"; Heat and Mass Transfer 38 (2002) 359-367.

Matlosz et al.; "Selective Oxidation of 1-Butene to Maleic Anhydride—Comparison of the Performance between Microchannel Reactors and a Fixed Bed Reactor"; Microreaction Technology; IMRET 5: Proceedings of the Fifth International Conference on Microreaction Technology. (2001).

Steinfeldt et al.; "Comparative Studies of the Oxidative Dehydrogenation of Propane in Micro-Channels Reactor Module and Fixed-Bed Reactor"; Studies in Surface Science and Catalysis; 2001 Elsevier Science B.V.; pp. 185-190.

Beretta et al.; "Production of Olefins via Oxidative Dehydrogenation of Light Paraffins at Short Contact Times"; Catalysis Today; 2001 Elsevier Science B.V.; pp. 103-111.

Waku et al.; "Effects of $O_2$ Concentration on the Rate and Selectivity in Oxidative Dehydrogenation of Ethane Catalyzed by Vanadium Oxide: Implications for $O_2$ Staging and Membrane Reactors"; Ind. Eng. Chem. Res. 2003, 41, 5462-5466.

International Search Report and Written Opinion; Application No. PCT/US2005/042143; mailed Mar. 27, 2006.

Chen et al.; "Performance analysis of a folding flow micromixer"; Microfluid Nanofluid (2009) 6:763-774.

MacInnes et al.; "Investigation of alternating-flow mixing in microchannels"; Chemical Engineering Science 60; 2005; pp. 3453-3467.

MacInnes et al.; "Numerial characterization of floding flow microchannel mixers"; Chemical Engineering Science 62; 2007; pp. 2718-2727.

MacInnes et al.; "Mixing Strategies for Flow in Microchannel Devices"; Chemical and Process Engineering, University of Sheffield, Nov. 24, 2004.

Canadian Office Action, Application No. 2,586,971, dated Aug. 2, 2010.

Chinese Office Action, Application No. 200580043686.1, issued Jun. 26, 2009.

Canadian Office Action, Application No. 2,586,971, dated Apr. 13, 2012.

EP Office Action, Application No. 05 846 987.5, dated Nov. 8, 2011.

\* cited by examiner

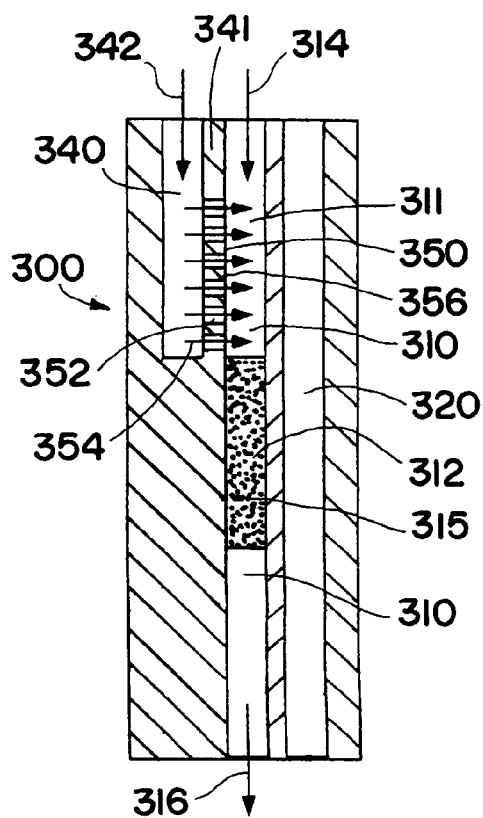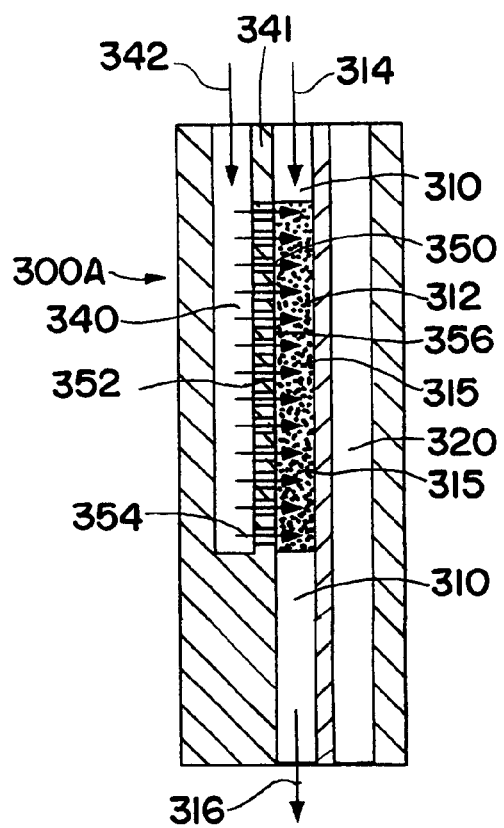
FIG. 4    FIG. 5
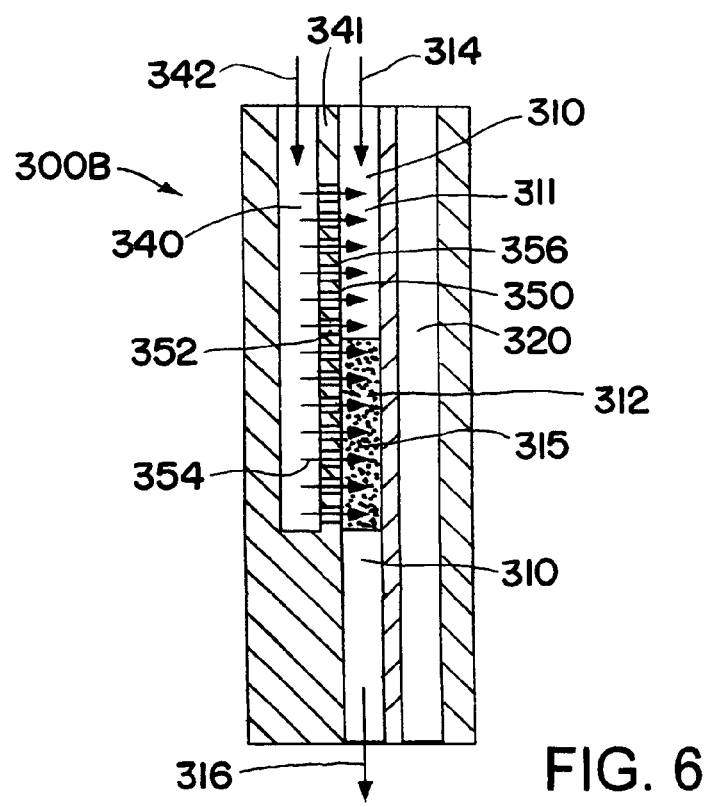
FIG. 6

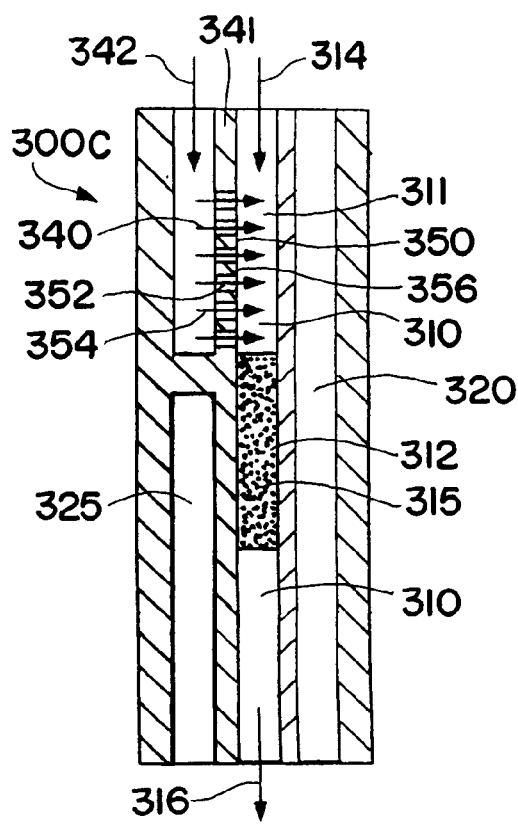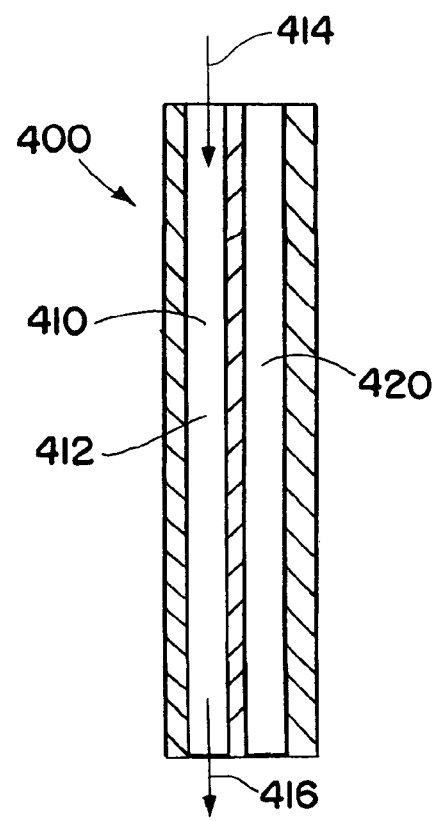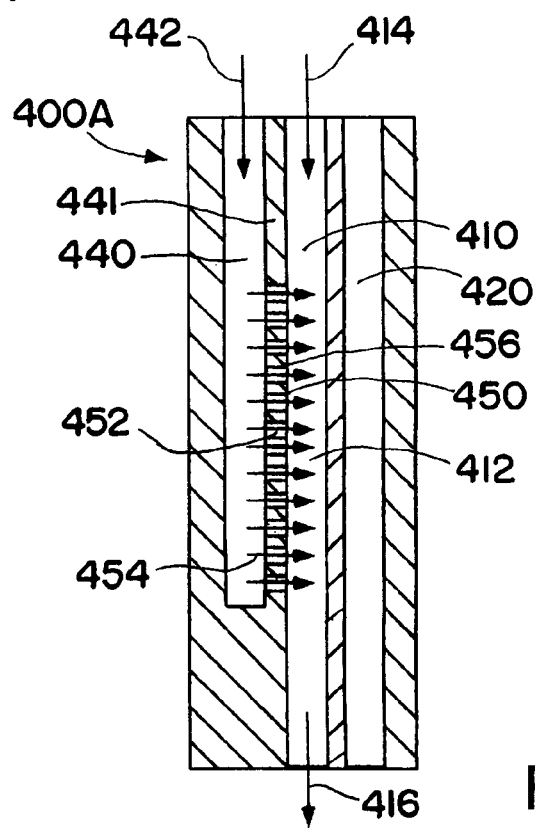
FIG. 7
FIG. 8
FIG. 9

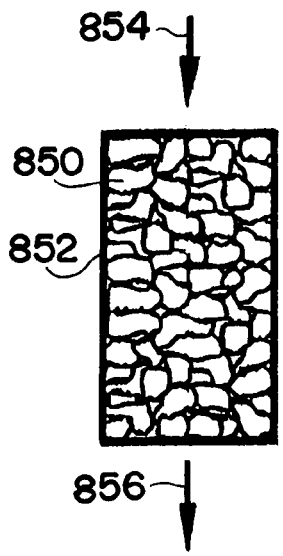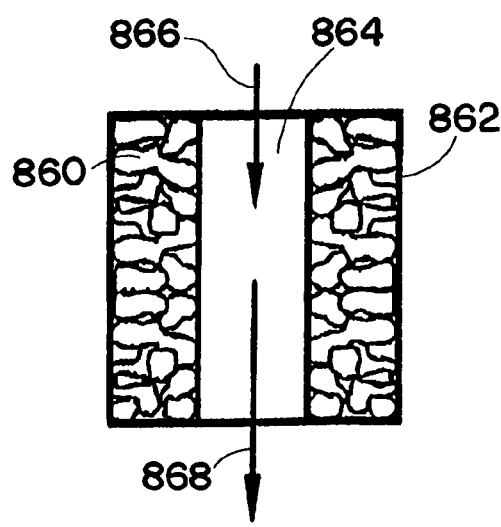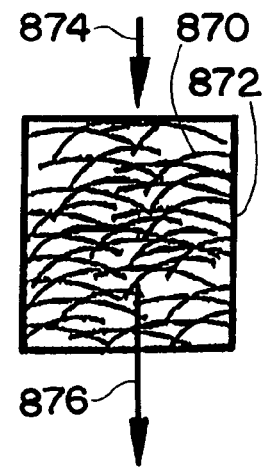
FIG. 22   FIG. 23   FIG. 24
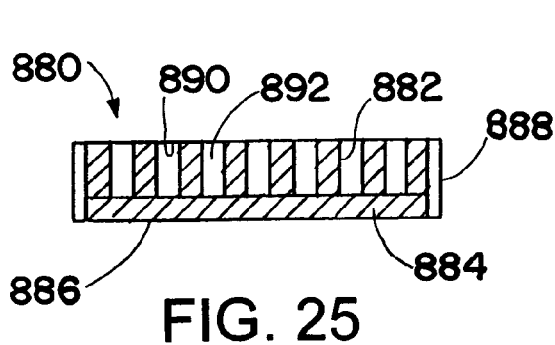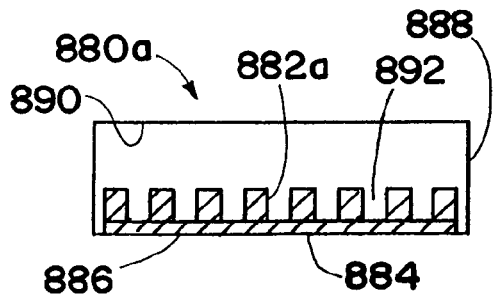
FIG. 25   FIG. 26
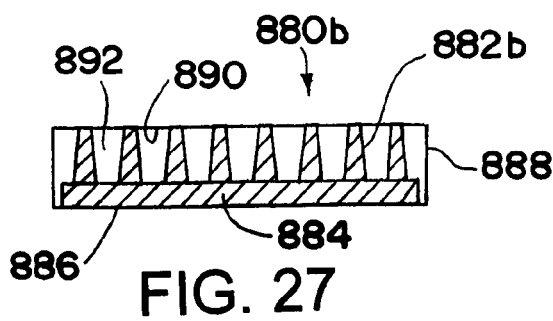
FIG. 27

PROCESS USING MICROCHANNEL TECHNOLOGY FOR CONDUCTING ALKYLATION OR ACYLATION REACTION

This application claims priority under 35 U.S.C. §119(e) to U.S. Provisional Application Ser. No. 60/627,269, filed Nov. 12, 2004, U.S. Provisional Application Ser. No. 60/697,900, filed Jul. 8, 2005, U.S. Provisional Application Ser. No. 60/727,126, filed Oct. 13, 2005, and U.S. Provisional Application Ser. No. 60/731,596, filed Oct. 27, 2005. The disclosures in these prior applications are incorporated herein by reference in their entirety.

TECHNICAL FIELD

This invention relates to a process for conducting an alkylation or acylation reaction in a microchannel reactor.

BACKGROUND

Alkylation is the reaction of adding an alkyl or an alkenyl group to a compound. Acylation is the reaction of adding an acyl group to a compound. Although alkylations are often referred to as acid-catalyzed Friedel-Crafts-type reactions, they can also refer to the preparation of alkylates in refinery conditions. These processes are useful for synthesizing fine chemicals for pharmaceutical and agricultural chemicals, as well as large volume chemicals. The large volume chemicals include: ethyl benzene from benzene and ethylene (in excess of about 23 million metric tons/year); cummene from benzene and propylene (in excess of about 9.5 million metric tons/year); bisphenol A from phenol and acetone (about 1.1 million metric tons/year); and alkylbenzenes from benzene and $C_{10}$-$C_{18}$ olefins to (about 900,000 metric tons/year). Other chemicals include: alkylbenzenes from propylenes, isobutene, butylenes and amylenes; detergent alkylates from benzene and linear aliphatic olefins; xylene; polynuclear aromatics alkylated with olefins and olefin-producing reagents; alkylated phenol derivatives (2,6-xylenol, o-cresol); alkylated aromatic amines (e.g., 5-tert-butyl-2,4-toluenediamine); and alkylated pyridines.

A problem with many of these processes is that selectivity to the desired product is often less than desired. As a result, costly downstream purification procedures are often required. For example, in the production of ethyl benzene from ethylene and benzene, undesired by-products such as polyethyl benzenes, xylene, $C_3^+$ alkenes and other undesirable by-products are typically produced.

SUMMARY

The inventive process may provide a solution to this problem. In one embodiment, the inventive process provides for relatively high selectivities for the desired products as a result of more precise temperature control and more efficient reactant mixing when compared to the prior art. Because of the more efficient mixing that may be realized with the inventive process, reductions in the amount of the alkylating or acylating agent that is required can be realized. In one embodiment, undesired coking can be reduced as a result of the more precise temperature control that is possible with the inventive process. As a result of process intensification that may be provided with the inventive process, lower heat exchange costs can be realized.

This invention relates to a process comprising: flowing a first reactant feed stream comprising a reactant substrate and a second reactant feed stream comprising an alkylating agent, an acylating agent or a mixture thereof, in a process microchannel in contact with each other to form a product comprising at least one alkylation product, at least one acylation product, or a mixture thereof; transferring heat from the process microchannel to a heat sink; and removing the product from the process microchannel.

In one embodiment, the first reactant feed stream and the second reactant feed stream are mixed prior to entering the process microchannel.

In one embodiment, the first reactant feed stream flows through a staged addition microchannel, the staged addition microchannel being adjacent to the process microchannel, the process microchannel having an entrance for the second reactant feed stream, the second reactant feed stream entering the entrance for the second reactant feed stream, the first reactant feed stream flowing through the staged addition microchannel and entering the process microchannel downstream of the entrance for the second reactant feed stream.

In one embodiment, the second reactant feed stream flows through a staged addition microchannel, the staged addition microchannel being adjacent to the process microchannel, the process microchannel having an entrance for the first reactant feed stream, the first reactant feed stream entering the process microchannel through the entrance for the first reactant feed stream, the second reactant feed stream flowing through the staged addition microchannel and entering the process microchannel downstream of the entrance for the first reactant feed stream.

In one embodiment, a reaction zone is positioned within the process microchannel, the second reactant feed stream contacting the first reactant feed stream in the reaction zone.

In one embodiment, a mixing zone and a reaction zone are positioned within the process microchannel, the mixing zone being upstream of the reaction zone, the second reactant feed stream contacting the first reactant feed stream in the mixing zone.

In one embodiment, a mixing zone and a reaction zone are positioned within the process microchannel, the mixing zone being upstream of the reaction zone, part of the second reactant feed stream contacting the first reactant feed stream in the mixing zone, and part of the second reactant feed stream contacting the first reactant feed stream in the reaction zone.

In one embodiment, the reactants may flow through a region in the reaction zone and/or mixing zone that contains surface features. The surface features may have a catalyst positioned on and/or within the surface features. The surface features may modify flow to provide intimate mixing between the reactants as the reaction proceeds. In one embodiment, an apertured section may be positioned in a common wall separating the process microchannel and the staged addition microchannel, and one of the reactant feed streams (i.e., the first or second reactant feed stream) flows through the apertured section into the reaction zone and/or mixing zone. Surface features on or in the apertured section may be used to enhance mixing of the reactants.

In one embodiment, the product is formed in the presence of a catalyst, the catalyst being in the form of a liquid. In one embodiment, the catalyst is mixed with the first reactant feed stream prior to flowing the first reactant feed stream in the process microchannel. In one embodiment, the catalyst is mixed with the second reactant feed stream prior to flowing the second reactant feed stream in the process microchannel. In one embodiment, the first reactant feed stream, the second reactant feed stream and the catalyst are mixed prior to entering the process microchannel.

In one embodiment, the first reactant feed stream is in the form of a liquid and flows through the process microchannel in a first direction, the second reactant feed stream is in the form of a vapor and flows through the process microchannel in a second direction, the first reactant feed stream and the second reactant feed stream contacting each other in a reaction zone and reacting to form the product, the product flowing in the first direction out of the process microchannel.

In one embodiment, the second reactant feed stream is in the form of a liquid and flows through the process microchannel in a first direction, the first reactant feed stream is in the form of a vapor and flows through the process microchannel in a second direction, the first reactant feed stream and the second reactant feed stream contacting each other in a reaction zone and reacting to form the product, the product flowing in the first direction out of the process microchannel.

In one embodiment, the process microchannel is adjacent to a liquid channel; the process microchannel comprising a plurality of reactive distillation stages; each reactive distillation stage comprising a liquid entrance for permitting liquid to flow from the liquid channel to the process microchannel, a liquid exit for permitting liquid to flow from the process microchannel to the liquid channel, a capture structure, and a catalyst-containing wall; the liquid channel comprising a wicking region; the process comprising: flowing a liquid phase comprising the first reactant feed stream from the liquid channel through the liquid entrance into the process microchannel, and in the process microchannel in contact with the catalyst-containing wall; flowing a vapor phase comprising the second reactant feed stream through the process microchannel in contact with the liquid phase, at least part of the alkylating and/or acylating agent in the vapor phase transferring from the vapor phase to the liquid phase and reacting with the reactant substrate in the liquid phase to form the product, the liquid phase becoming a product rich liquid phase, the vapor phase becoming an alkylating and/or acylating agent lean vapor phase; separating the product rich liquid phase from the alkylating and/or acylating agent lean vapor phase; flowing the product rich liquid phase through the liquid exit into the liquid channel; and flowing the alkylating and/or acylating agent lean vapor phase through the capture structure.

In one embodiment, the process microchannel is adjacent to a liquid channel; the process microchannel comprising a plurality of reactive distillation stages; each reactive distillation stage comprising a liquid entrance for permitting liquid to flow from the liquid channel to the process microchannel, a liquid exit for permitting liquid to flow from the process microchannel to the liquid channel, a capture structure, and a catalyst-containing wall; the liquid channel comprising a wicking region; the process comprising: flowing a liquid phase comprising the second reactant feed stream from the liquid channel through the liquid entrance into the process microchannel, and in the process microchannel in contact with the catalyst-containing wall; flowing a vapor phase comprising the first reactant feed stream through the process microchannel in contact with the liquid phase, at least part of the reactant substrate in the vapor phase transferring from the vapor phase to the liquid phase and reacting with the alkylating and/or acylating agent in the liquid phase to form the product, the liquid phase becoming a product rich liquid phase, the vapor phase becoming a reactant substrate lean vapor phase; separating the product rich liquid phase from the reactant substrate lean vapor phase; flowing the product rich liquid phase through the liquid exit into the liquid channel; and flowing the reactant substrate lean vapor phase through the capture structure.

BRIEF DESCRIPTION OF THE DRAWINGS

In the annexed drawings, like parts and features have like designations.

FIG. 4 is a schematic illustration of an alternate embodiment of a repeating unit comprising a process microchannel, a staged addition microchannel and a heat exchange channel that may be used in the microchannel reactor core of the microchannel reactor illustrated in FIG. 2.

FIG. 5 is a schematic illustration of another alternate embodiment of a repeating unit comprising a process microchannel, a staged addition microchannel and heat exchange channel that may be used in the microchannel reactor core of the microchannel reactor illustrated in FIG. 2.

FIG. 6 is a schematic illustration of another alternate embodiment of a repeating unit comprising a process microchannel, a staged addition microchannel and heat exchange channel that may be used in the microchannel reactor core of the microchannel reactor illustrated in FIG. 2.

FIG. 7 is a schematic illustration of another alternate embodiment of a repeating unit comprising a process microchannel, a staged addition microchannel and two heat exchange channels that may be used in the microchannel reactor core of the microchannel reactor illustrated in FIG. 2.

FIG. 8 is a schematic illustration of another alternate embodiment of a repeating unit comprising a process microchannel and a heat exchange channel that may be used in the microchannel reactor core of the microchannel reactor illustrated in FIG. 2.

FIG. 9 is a schematic illustration of another alternate embodiment of a repeating unit comprising a process microchannel, a staged addition microchannel and heat exchange channel that may be used in the microchannel reactor core of the microchannel reactor illustrated in FIG. 2.

FIG. 22 is a schematic illustration of a process microchannel that may be used with the inventive process, the process microchannel containing a catalyst having a packed bed configuration.

FIG. 23 is a schematic illustration of a process microchannel that may be used with the inventive process, the process microchannel containing a catalyst having a flow-by configuration.

FIG. 24 is a schematic illustration of a process microchannel that may be used with the inventive process, the process microchannel containing a catalyst having a flow-through configuration.

FIG. 25 is a schematic illustration of a process microchannel that may be used in the inventive process, the process microchannel containing a fin assembly comprising a plurality of fins, a catalyst being supported by the fins.

FIG. 26 illustrates an alternate embodiment of the process microchannel and fin assembly illustrated in FIG. 25.

FIG. 27 illustrates another alternate embodiment of the process microchannel and fin assembly illustrated in FIG. 25.

DETAILED DESCRIPTION

The term "alkylation" is used to designate the reaction in which an alkyl group is added to a compound. The term "alkenylation" refers to a reaction in which an alkenyl group is added to a compound. For reasons of simplicity, in the following description and in the claims the term alkylation is used to refer to both reactions.

The term "acylation" is used to designate a reaction in which an acyl group is added to a compound.

The term "reactant substrate" refers to a compound which when reacted with an alkylating agent forms a compound with an added alkyl and/or an alkenyl group, and/or to a compound which when reacted with an acylating agent forms a compound with an added acyl group.

The term "alkylating agent" refers to a compound which when reacted with a reactant substrate forms a compound with an added alkyl and/or alkenyl group.

The term "acylating agent" refers to a compound which when reacted with a reactant substrate forms a compound with an added acyl group.

The term "alkylating and/or acylating agent" refers to an akylating agent, an acylating agent, or a mixture thereof.

The term "alkylation product" refers to a compound having an added alkyl and/or alkenyl group formed by the reaction of a reactant substrate with an alkylating agent.

The term "acylation product" refers to a compound having an added acyl group formed by the reaction of a reactant substrate with an acylating agent.

The term "alkylation and/or acylation product" refers to an alkylation product, an acylation product, or a mixture thereof.

Figure 1:
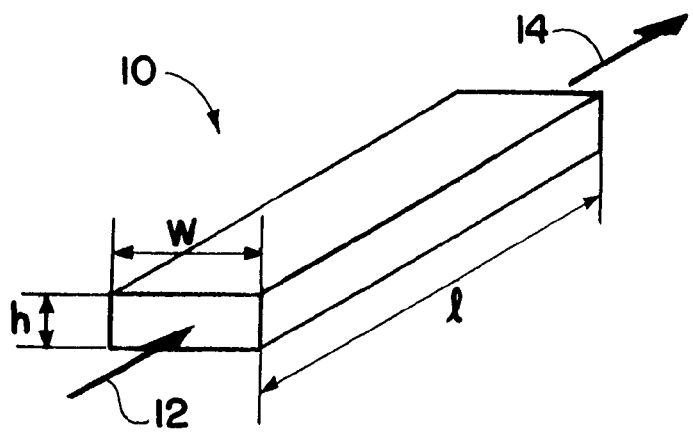
FIG. 1 is a schematic illustration of a microchannel that may be used with the inventive process.

The term "microchannel" refers to a channel having at least one internal dimension of height or width of up to about 10 millimeters (mm), and in one embodiment up to about 5 mm, and in one embodiment up to about 2 mm, and in one embodiment up to about 1 mm. An example of a microchannel that may be used with the inventive process as a process microchannel and/or a heat exchange microchannel is illustrated in FIG. 1. The microchannel 10 illustrated in FIG. 1 has a height (h), width (w) and axial length (l). Fluid flows through the microchannel 10 in a direction that is perpendicular to both the height and width as indicated by directional arrows 12 and 14. The height (h) or width (w) of the microchannel may be in the range of about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.75 mm, and in one embodiment about 0.05 to about 0.5 mm. In one embodiment the height or width may range from about 0.15 to about 10 mm, and in one embodiment from about 0.2 to about 10 mm, and in one embodiment from about 0.3 to about 10 mm. The other dimension of height or width may be of any dimension, for example, up to about 3 meters, and in one embodiment about 0.01 to about 3 meters, and in one embodiment about 0.1 to about 3 meters. The axial length (l) of the microchannel may be of any dimension, for example, up to about 10 meters, and in one embodiment in the range from about 0.05 to about 10 meters, and in one embodiment in the range from about 0.1 to about 10 meters, and in one embodiment from about 0.2 to about 10 meters, and in one embodiment from about 1 to about 10 meters, and in one embodiment from about 0.2 to about 6 meters, and in one embodiment from 0.2 to about 3 meters. Although the microchannel 10 illustrated in FIG. 1 has a cross section that is rectangular, it is to be understood that the microchannel may have a cross section having any shape, for example, a square, circle, semi-circle, trapezoid, etc. The shape and/or size of the cross section of the microchannel may vary over its length. For example, the height or width may taper from a relatively large dimension to a relatively small dimension, or vice versa, over the axial length of the microchannel.

The term "microchannel reactor" refers to a reactor wherein a chemical reaction is conducted in a microchannel.

The term "adjacent" when referring to the position of one channel relative to the position of another channel means directly adjacent such that a wall separates the two channels. This wall may vary in thickness. However, "adjacent" channels are not separated by an intervening channel that would interfere with heat transfer between the channels.

The term "surface feature" refers to a depression in a microchannel wall and/or a projection from a microchannel wall that modifies flow and/or enhances mixing within the microchannel. The surface features may be in the form of circles, oblongs, squares, rectangles, checks, chevrons, wavy shapes, and the like. The surface features may contain sub features where the major walls of the surface features further contain smaller surface features that may take the form of notches, waves, indents, holes, burrs, checks, scallops, and the like. The surface features have a depth, a width, and for non-circular surface features a length. Examples are illustrated in FIGS. 30-34. The surface features may be formed on or in one or more of the interior side walls of the process microchannels used in the inventive process. The surface features may be formed on or in one or more of the interior side walls of the staged addition microchannels and/or heat exchange channels used in the inventive process. The surface features may be referred to as passive surface features or passive mixing features. The surface features may be used to disrupt laminar flow streamlines and create advective flow at an angle to the bulk flow direction. This may enhance contact between the reactants and catalyst, especially when the catalyst is positioned on the process microchannel sidewalls or on the surface features.

The term "fluid" refers to a gas, a liquid, or a gas or a liquid containing dispersed solids, or a mixture thereof. The fluid may be in the form of a gas containing dispersed liquid droplets. The fluid may be in the form of a liquid containing dispersed liquid or gas droplets.

The term "contact time" refers to the volume of the reaction zone within the microchannel reactor divided by the volumetric feed flow rate of a fluid flowing through the reaction zone at a temperature of 0° C. and a pressure of one atmosphere.

The term "reaction zone" refers to volume within a channel wherein a catalyst is positioned and/or a reaction takes place.

The term "residence time" refers to the internal volume of a space (e.g., a mixing zone within a process microchannel) occupied by a fluid flowing through the space divided by the volumetric flowrate for the fluid flowing through the space at the temperature and pressure within the space.

The term "superficial" velocity" for the velocity of a fluid flowing in a channel refers to the volumetric flow rate at standard pressure and temperature divided by the open cross sectional area of the channel.

The terms "upstream" and "downstream" refer to positions within a channel (e.g., a process microchannel) used in the inventive process that is relative to the direction of flow of a fluid stream in the channel. For example, a position within the channel not yet reached by a portion of a fluid stream flowing toward that position would be downstream of that portion of the fluid stream. A position within the channel already passed by a portion of a fluid stream flowing away from that position would be upstream of that portion of the fluid stream. In the embodiments illustrated in FIGS. 11-13, the upstream and downstream positions are relative to the direction of flow of the vapor phase through the process microchannels. The terms "upstream" and "downstream" do not necessarily refer to a vertical position since the channels used in the inventive process may be oriented horizontally, vertically or at an inclined angle.

The term "heat sink" refers to a substance or device that absorbs heat and may be used to cool another substance or device. The heat sink may be in the form of a heat exchange channel having a heat exchange fluid in it that receives heat transferred from another substance or device; the another substance or device being, for example, a channel that is adjacent to or sufficiently near the heat exchange channel to transfer heat to the heat exchange channel. The heat exchange fluid may be contained in the heat exchange channel and/or flow through the heat exchange channel. The heat sink may be in the form of a cooling element, for example, a non-fluid cooling element.

The term "heat exchange channel" refers to a channel having a heat exchange fluid in it that may absorb heat.

The term "heat exchange fluid" refers to a fluid that may absorb heat.

The term "capture structure" refers to a structure positioned within a process microchannel that enhances the movement of liquid into an adjacent wicking region through the use of capillary forces.

The term "wicking region" refers to a volume occupied by a wick or a wicking surface such as a grooved microchannel surface. A liquid may be preferentially retained within and flow through the wick or the wicking surface as a result of capillary forces.

The term "fluid" refers to a gas, a liquid, or a mixture thereof. The fluid may be a gas and/or liquid containing dispersed solids. The fluid may be a liquid containing dispersed liquid droplets. The fluid may be a gas containing dispersed liquid droplets.

The term "conversion of reactant substrate" refers to the reactant substrate mole change between a fluid entering a microchannel reactor and a fluid exiting the microchannel reactor divided by the moles of reactant substrate in the fluid entering the microchannel reactor.

The term "conversion of alkylating and/or acylating agent" refers to the alkylating and/or acylating agent mole change between a fluid entering the microchannel reactor and a fluid exiting the microchannel reactor divided by the moles of alkylating and/or acylating agent in the fluid entering the microchannel reactor.

The term "yield" is used herein to refer to (i) the number of moles of alkylation and/or acylation product divided by the product stoichiometric coefficient exiting a microchannel reactor, divided by (ii) the number of moles of alkylating and/or acylating agent entering the microchannel reactor divided by the reactant stoichiometric coefficient. For example, if one mole of alkylating agent is used in a reaction that produces one mole of alkylation product, then both stoichiometric coefficients are one. If two moles of an alkylating agent are used in a reaction to produce one mole of alkylation product, then the reactant stoichiometric coefficient is two, and the product stoichiometric coefficient is one.

The term "cycle" is used herein to refer to a single pass of the reactants through a microchannel reactor.

The term "hydrocarbyl" refers to a group having a carbon atom directly attached to the remainder of the molecule and having a hydrocarbon or predominantly hydrocarbon character. These groups include the following:

(1) Purely hydrocarbon groups; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic groups, and the like, as well as cyclic groups wherein the ring is completed through another portion of the molecule (that is, any two indicated substituents may together form an alicyclic group). Examples include methyl, ethyl, octyl, decyl, octadecyl, cyclohexyl, phenyl, etc.

(2) Substituted hydrocarbon groups; that is, groups containing non-hydrocarbon substituents which do not alter the predominantly hydrocarbon character of the group. Examples of these substituents include hydroxy, nitro, cyano, halo, alkoxy, acyl, etc.

(3) Hetero groups; that is, groups which, while predominantly hydrocarbon in character, contain atoms other than carbon in a chain or ring otherwise composed of carbon atoms. These hetero atoms include, for example, nitrogen, oxygen and sulfur.

The hydrocarbyl groups with a predominantly hydrocarbon character may contain up to about three substituents and/or hetero atoms, and in one embodiment not more than one substituent and/or heteroatom, for each 10 carbon atoms in the hydrocarbyl group.

The reactant substrate may comprise any compound capable of reacting with an alkylating and/or an acylating agent to form an alkylation and/or acylation product. The reactant substrate may comprise an aliphatic, aromatic, aliphatic-substituted aromatic, or aromatic-substituted aliphatic compound. The reactant substrate may comprise a substituted hydrocarbon compound, that is, a hydrocarbon compound containing one or more non-hydrocarbon groups such as hydroxyl, halo, nitro, amino, cyano, alkoxy, acyl, etc. The reactant substrate may comprise a hetero substituted hydrocarbon compound, that is, a hydrocarbon compound containing one or more atoms other than carbon in a chain or ring otherwise comprising carbon atoms; examples of such hetero atoms including nitrogen, oxygen and sulfur.

The reactant substrate may comprise an aliphatic compound. These include straight chain aliphatic compounds, branched chain aliphatic compounds, and mixtures thereof. These compounds may contain from 1 to about 40 carbon atoms, and in one embodiment from 1 to about 30 carbon atoms, and in one embodiment from 1 to about 20 carbon atoms, and in one embodiment from about 2 to about 12 carbon atoms. The reactant substrate may comprise an alkane and/or an isoalkane. The alkane and/or isoalkane may contain from 1 to about 40 carbon atoms, and in one embodiment 1 to about 30 carbon atoms, and in one embodiment from 1 to about 20 carbon atoms, and in one embodiment from about 2 to about 12 carbon atoms, and in one embodiment from about 4 to about 6 carbon atoms. Examples of these reactant substrates include: isobutane; pentane; isopentane; isohexane; 2-methyl butane; 2-methyl pentane; and 3-methyl pentane.

The reactant substrate may comprise an aromatic compound. These include benzene, naphthalene, alkylated derivatives thereof, and the like. The aromatic compound may contain from 6 to about 40 carbon atoms, and in one embodiment from 6 to about 30 carbon atoms, and in one embodiment from 6 to about 20 carbon atoms, and in one embodiment from 6 to about 15 carbon atoms, and in one embodiment from 6 to about 12 carbon atoms. Examples include benzene, toluene, ethylbenzene, propylbenzene, xylene, mesitylene, methylethylbenzene, naphthalene, anthracene, phenanthrene, methylnaphthalene, dimethylnaphthalene, tetralin, and the like. The reactant substrate may comprise phenol, benzene diol, naphthol and/or naphthalene diol. The reactant substrate may comprise an aromatic amine and/or a pyridine. The reactant substrate may comprise aniline, toluidine, phenylenediamine and/or toluene diamine.

The reactant substrate may comprise an alkylbenzene with a multi-substituted benzene ring. Examples include o-, m- and p-xylene, toluene, tolyl aldehyde, aminotoluene, o-, m- and p-cresol, phenyl aldehyde, and the like.

The reactant substrate may comprise one or more polymers. These polymers may be homopolymers or interpolymers (e.g., copolymers, terepolymers, etc.). The polymers may be aliphatic, aromatic, or a combination thereof. The polymers include straight chain polymers and branched chain polymers. The polymers include random copolymers and block copolymers. The polymers may be derived from monomers containing 2 to about 12 carbon atoms, and in one embodiment 2 to about 8 carbon atoms, and in one embodiment 2 to about 4 carbon atoms. The monomers may be mono-olefins or di-olefins. The mono-olefins include 1-olefins. Examples of the monomers that may be used include ethylene, propylene, 1-butene, isobutene, butadiene, isoprene, 1-hexene, 1-octene, styrene, etc. The polymers include polyethylene, polypropylene, polyisobutylene, polybutadiene, polyisoprene, polystyrene, copolymers of ethylene and propylene, etc.

The alkylating agent may comprise one or more olefins containing 2 to about 30 carbon atoms, and in one embodiment 2 to about 20 carbon atoms, and in one embodiment 2 to about 12 carbon atoms, and in one embodiment 2 to about 6 carbon atoms. In one embodiment, the alkylating agent may comprise one or more olefins containing about 10 to about 18 carbon atoms. The alkylating agent may comprise a monoolefin, a diolefin, or a mixture thereof. The alkylating agent may comprise one or more alpha-olefins. Examples include ethylene, propylene, butene-1, cis-butene-2, trans-butene-2, isobutylene, 1,3-butadiene, amylene, isoamylene, 2-pentene, 2-methyl-butene-2, 1-pentene, 3-methyl-butene-1,2-methyl-butene-1, isoprene, piperylene, cyclopentene, 1-hexene, 2-methyl-1-pentene, 2-methyl-2-pentene, 1-octene, diisobutylene, 1-decene, 1-dodecene, 2-dodecene, 1-tetradecene, 2-tetradecene, 1-hexadecene, 1-eicosene, α-pinene, camphene, limonene, styrene and mixtures of two or more thereof. Olefin precursors which dehydrate or in some other way eliminate or rearrange under the reaction conditions to form an olefin may be employed as the alkylating agent.

The acylating agent may comprise one or more carboxylic acids and/or derivatives thereof. The derivative may be anhydrides, esters and/or acyl halides. The carboxylic acid or derivative may comprise one or more monobasic and/or polybasic alpha-beta olefinically unsaturated carboxylic acids, and/or one or more anhydride, ester or acyl halide derivatives thereof. The acylating agent may comprise at least one compound represented by the formula

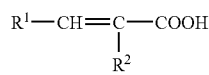

wherein $R^1$ and $R^2$ are independently hydrogen or hydrocarbyl groups. $R^1$ and $R^2$ independently may be hydrocarbyl groups containing 1 to about 20 carbon atoms, and in one embodiment 1 to about 12 carbon atoms, and in one embodiment 1 to about 4 carbon atoms. The acylating agent may comprise one or more of: acrylic acid; methacrylic acid; cinnamic acid; crotonic acid; 3-phenyl propenoic acid; alpha,beta-decanoic acid; maleic acid; fumaric acid; mesaconic acid; itaconic acid; citraconic acid; maleic anhydride; and acetone.

The molar ratio of the reactant substrate to the alkylating and/or acylating agent may be in the range from about 10 to about 1, and in one embodiment about 8 to about 1, and in one embodiment about 5 to about 1, and in one embodiment about 2 to about 1, and in one embodiment about 1 to about 1.

The alkylation and/or acylation product may comprise one or more of ethyl benzene, cumene, cymene, ($C_{10}$-$C_{18}$)alkylbenzene, refinery alkylates, detergent alkylates, xylene, alkylated phenols, alkylated phenol derivatives (e.g., 2,6-xylenol, o-cresol). The product may comprise an alkylated aromatic amine (e.g., 5-tert-butyl-2,4-toluene diamine) or an alkylated pyridine. The product may comprise dimethyl pentane and/or trimethyl pentane. The product may comprise bisphenol A. The product may comprise a hydrocarbyl substituted carboxylic acid or anhydride, such as a polyethylene or polyisobutylene substituted carboxylic acid or anhydride.

Figure 2:
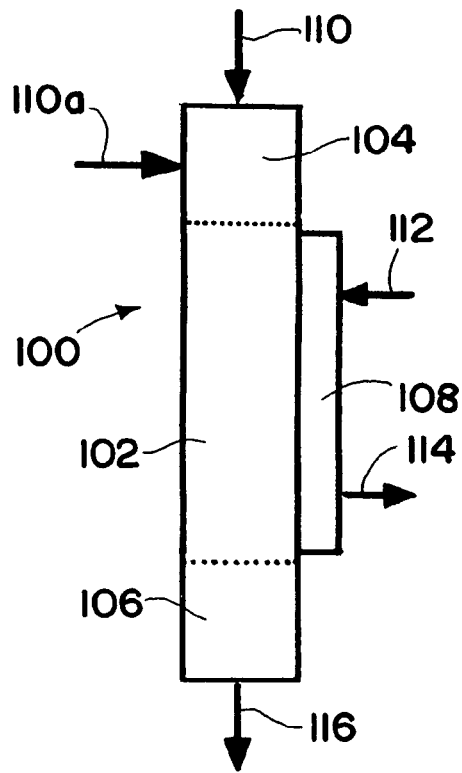
FIG. 2 is a schematic drawing illustrating the inventive process in a particular form wherein a first reactant feed stream comprising a reactant substrate and a second reactant feed stream comprising an alkylating and/or acylating agent flow in a microchannel reactor in contact with each other and react to form an alkylation and/or acylation product.

The inventive process, in one embodiment, may be conducted as illustrated in FIGS. 2-10. Referring to FIG. 2, the process may be operated using microchannel reactor 100 which includes microchannel reactor core 102, feed stream header 104, product footer 106, and heat exchange manifold 108. The reactor core 102 contains one or more process microchannels. Each of the process microchannels contains one or more reaction zones wherein the reactants contact each other and react to form the desired product. In one embodiment, a catalyst in solid form may be present in one or more of these reaction zones. In one embodiment, a catalyst in liquid form may flow into the reaction zone with one or more of the reactants and/or in a separate feed stream. The feed stream header 104 may comprise one or more manifolds for distributing the feed streams to the process microchannels. The product footer 106 may comprise one or more manifolds for collecting product from the process microchannels.

In one embodiment, a first reactant feed stream comprising a reactant substrate and a second reactant feed stream comprising an alkylating agent, an acylating agent, or a mixture thereof, may be premixed and then flow into the microchannel reactor 100 through the feed stream header 104, as indicated by arrow 110. Alternatively, the first reactant feed stream may flow into feed stream header 104, as indicated by arrow 110, and the second reactant feed stream may flow separately into feed stream header 104, as indicated by arrow 110a. The first reactant feed stream and the second reactant feed stream (premixed or flowing separately) may flow through the header 104 and from the header 104 into the one or more process microchannels in reactor core 102. In the process microchannels the reactant feed streams flow into the reaction zones, contact each other and the catalyst, and react to form the desired product. The product may flow from the process microchannels through product footer 106, and from product footer 106 out of the reactor, as indicated by arrow 116. Although an advantage of the inventive process is that a high level of conversion to the desired product may be obtained with one pass through the microchannel reactor, in one embodiment, one or more unreacted reactants may be separated from the product using conventional techniques and recycled back through the microchannel reactor. The unreacted reactants may be recycled through the microchannel reactor any number of times, for example, one, two, three, four times, etc.

The alkylation and/or acylation reactions that may be conducted in accordance with this process are exothermic and thus in order to control the reaction, heat may be transferred from the process microchannels to a heat sink. That is, during the inventive process heat may be transferred from at least one or more of the process microchannels in the microchannel reactor 100 and/or from at least part of one or more of such process microchannels to a heat sink. The heat sink may be adjacent to one or more of the process microchannels, or remote from the one or more process microchannels but sufficiently close to the one or more process microchannels to absorb heat from the one or more process microchannels. The heat sink may comprise one or more heat exchange channels containing a heat exchange fluid, and/or one or more non-fluid cooling elements. The heat sink may provide active cooling to the process microchannels.

In one embodiment, a heat exchange fluid flows into heat exchange manifold 108, as indicated by arrow 112, then from heat exchange manifold 108 through heat exchange channels in the reactor core 102 then back to the heat exchange manifold 108, and then out of heat exchange manifold 108, as indicated by arrow 114. The heat exchange manifold 108 may comprise one or more heat exchange headers and one or more heat exchange footers to separate the heat exchange inlet stream 112 from the heat exchange outlet stream 114.

Heat exchange between the reactant feed streams and product, and the heat sink may be effected using convective heat transfer. In one embodiment, heat exchange may be enhanced by the use of a heat exchange fluid which undergoes an endothermic reaction and/or a full or partial phase change. Multiple heat exchange zones may be employed along the length of one or more of the process microchannels in the reactor core 102 to provide for different temperatures and/or different heat fluxes at different locations along the lengths of the process microchannels.

The microchannel reactor 100 may be used in combination with one or more storage vessels, pumps, valves, manifolds, microprocessors, flow control devices, and the like, which are not shown in the drawings, but would be apparent to those skilled in the art.

The first reactant feed stream and the second reactant feed stream may be premixed prior to entering the microchannel reactor 100 or they may be mixed in the microchannel reactor 100. Both feed streams may be fluids. The first reactant feed stream and the second reactant feed stream may be mixed with each other in the process microchannels in the microchannel reactor core 102. In one embodiment, the first reactant feed stream may be mixed with the second reactant feed stream in one or more of the reaction zones in the process microchannels. In one embodiment, one or more of the process microchannels contain mixing zones upstream of the reaction zones, and the first reactant feed stream may be mixed with the second reactant feed stream in the mixing zones. In one embodiment, one or more of the process microchannels contains mixing zones upstream of the reaction zones, and the first reactant stream and the second reactant feed stream may be partially mixed in the mixing zones and partially mixed in the reaction zones. The volume of the second reactant feed stream mixed with the first reactant feed stream in the mixing zones may be in the range from about 1% to about 99% by volume of the second reactant feed stream, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume, with the remainder of the second reactant feed stream being mixed with the first reactant feed stream in the reaction zones.

Figure 3:
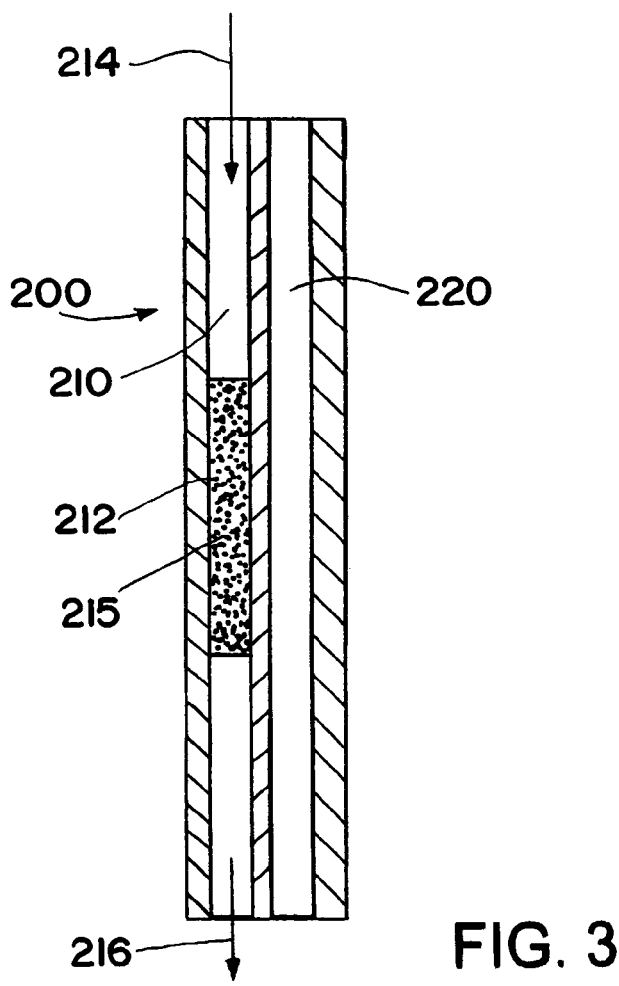
FIG. 3 is a schematic illustration of a repeating unit comprising a process microchannel and a heat exchange channel that may be used in the microchannel reactor core of the microchannel reactor illustrated in FIG. 2.

FIG. 3 illustrates repeating unit 200 which may be used in the reactor core 102 of the microchannel reactor 100. Repeating unit 200 comprises process microchannel 210 and heat exchange channel 220. Process microchannel 210 has a reaction zone 212 wherein the catalyst 215 is present. The catalyst 215 may fill the process microchannel cross section of the reaction zone 212 as shown in FIG. 3 or, alternatively, the catalyst may be coated on the process microchannel walls and/or fill only part of the process microchannel cross section. This is discussed below in greater detail. Thus, in FIG. 3, as well as FIGS. 4-7 and 11A, the catalyst as shown in the drawings may represent either a complete or partial filling of a process microchannel cross section and/or a coating on the walls of the process microchannel. In operation, the first reactant feed stream and second reactant feed stream are premixed using conventional techniques prior to entering the process microchannel 210. The mixture of the first reactant feed stream and the second reactant feed stream flows through feed stream header 104 into process microchannel 210, as indicated by arrow 214, contacts the catalyst 215, and reacts to form the desired alkylation product and/or acylation product. The product exits the process microchannel 210, as indicated by arrow 216. The product exiting the process microchannel 210 flows through product footer 106 and out of the reactor 100, as indicated by arrow 116. Heat exchange fluid flows from heat exchange manifold 108 through heat exchange channel 220, and then back to heat exchange manifold 108. The flow of heat exchange fluid through the heat exchange channel 220 may be co-current or counter-current to the flow of fluid flowing through process microchannel 210. Alternatively, the heat exchange channel 220 could be oriented to provide for the flow of the heat exchange fluid in a direction that would be cross-current to the flow of fluid through the process microchannel 210. The repeating unit 200 illustrated in FIG. 3 may occur once within the microchannel reactor core 102 or it may be repeated any number of times, for example, two, three, four, five, ten, twenty, fifty, one hundred, hundreds, one thousand, thousands, ten thousand, tens of thousands, one hundred thousand, hundreds of thousands, millions of times, etc.

FIG. 4 illustrates repeating unit 300 which may be used in the reactor core 102 of the microchannel reactor 100. Repeating unit 300 comprises process microchannel 310, heat exchange channel 320, staged addition microchannel 340, and apertured section 350. A common wall 341 separates process microchannel 310 and staged addition microchannel 340. The apertured section 350, which in one embodiment contains apertures 352 formed in sheet or plate 356, is positioned in common wall 341. The process microchannel 310 has a mixing zone 311, and a reaction zone 312. A catalyst 315 is positioned in the reaction zone 312. The mixing zone 311 is upstream from the reaction zone 312. The first reactant feed stream flows into process microchannel 310, as indicated by the arrow 314, and into the mixing zone 311. The second reactant feed stream flows into staged addition microchannel 340, as indicated by arrow 342, and from the staged addition microchannel 340 through apertures 352 into mixing zone 311, as indicated by arrows 354. The first reactant feed stream and the second reactant feed stream contact each other in the mixing zone 311 and form a reactant mixture. The direction of flow of the second reactant feed stream in the staged addition microchannel 340, as indicated by arrow 342, is concurrent with the direction of flow of the first reactant feed stream in the process microchannel 310, as indicated by arrow 314; alternatively, the flow of the second reactant feed stream in the staged addition microchannel 340 may be counter-current or cross-current relative to the flow of the first reactant feed stream in the process microchannel 310. The reactant mixture flows from the mixing zone 311 into the reaction zone 312, contacts the catalyst 315, and reacts to form the desired alkylation product and/or acylation product. The product exits the process microchannel 310, as indicated by arrow 316. The product exiting the process microchannel 310 flows through the product footer 106 and out of the reactor, as indicated by arrow 116. Heat exchange fluid flows from heat exchange manifold 108 through heat exchange channel 320 and then back to heat exchange manifold 108. The flow of heat exchange fluid through the heat exchange channel 320 may be co-current or counter-current to the flow of fluid flowing through process microchannel 310. Alternatively, the heat exchange channel 320 could be oriented to provide for the flow of the heat exchange fluid in a direction that would be cross-current to the flow of fluid through the process microchannel 310. The repeating unit 300 illustrated in FIG. 4 may occur once within the microchannel reactor core 102 or it may be repeated any number of times, for example, two, three, four, five, ten, twenty, fifty, one hundred, hundreds, one thousand, thousands, ten thousand, tens of thousands, one hundred thousand, hundreds of thousands or millions of times.

In an alternate embodiment of the repeating unit 300 illustrated in FIG. 4, a supplemental mixing zone may be provided in the process microchannel 310 between the mixing zone 311 and reaction zone 312. The residence time for mixing in the supplemental mixing zone may be defined using the sum of the total of the flow through the apertured section 350 and the flow of the first reactant feed stream in process microchannel 310, at standard conditions of temperature (i.e., 0° C.) and pressure (i.e., atmospheric pressure), and the volume defined by the process microchannel 310 between the end of the mixing zone 311 and the beginning of the reaction zone 312. This residence time for mixing in the supplemental mixing zone may be in the range up to about 500 milliseconds (ms), and in one embodiment from about 0.25 ms to about 500 ms, and in one embodiment from about 0.25 ms to about 250 ms, and in one embodiment from about 0.25 to about 50 ms, and in one embodiment from about 0.25 to about 2.5 ms.

The repeating unit 300A illustrated in FIG. 5 is identical to the repeating unit 300 illustrated in FIG. 4 with the exception that the repeating unit 300A does not contain the separate mixing zone 311. With repeating unit 300A, the second reactant feed stream flows through the apertured section 350 into the reaction zone 312 where it contacts the first reactant feed stream and reacts to form the desired product. The product then flows out of the process microchannel 310, as indicated by arrow 316.

The repeating unit 300B illustrated in FIG. 6 is identical to the repeating unit 300 illustrated in FIG. 4 with the exception that part of the second reactant feed stream mixes with the first reactant feed stream in the mixing zone 311, and the remainder of the second reactant feed stream mixes with the first reactant feed stream in the reaction zone 312. The amount of the second reactant feed stream that mixes with the first reactant feed stream in the mixing zone 311 can be from about 1% to about 99% by volume of the second reactant feed stream, and in one embodiment from about 5% to about 95% by volume, and in one embodiment from about 10% to about 90% by volume, and in one embodiment from about 20% to about 80% by volume, and in one embodiment from about 30% to about 70% by volume, and in one embodiment from about 40% to about 60% by volume of the second reactant feed stream. The remainder of the second reactant feed stream mixes with the first reactant feed stream in the reaction zone 312.

The repeating unit 300C illustrated in FIG. 7 is identical to the repeating unit 300 illustrated in FIG. 4 with the exception that the repeating unit 300C includes heat exchange channel 325. The flow of heat exchange fluid through the heat exchange channel 325 may be co-current or countercurrent to the flow of fluid through the process microchannel 310. Alternatively, the heat exchange channel 325 could be oriented to provide for the flow of heat exchange fluid in a direction that would be cross-current to the flow of fluid through the process microchannel 310.

The repeating unit 400 illustrated in FIG. 8 is suitable for conducting the inventive process using a liquid catalyst. The reaction that is conducted in this embodiment may be referred to as a homogeneous reaction. Repeating unit 400 comprises microchannel 410 and heat exchange channel 420. The process microchannel 410 includes reaction zone 412 wherein the homogeneous reaction takes place. The reaction zone 412 may extend over the entire length of the process microchannel 410, or its length may be less than the length of the process microchannel. In operation, the first reactant feed stream, second reactant feed stream and liquid catalyst are premixed using conventional techniques and the resulting mixture flows into the process microchannel 410, as indicated by arrow 414, and undergoes reaction in the reaction zone 412 to form the desired alkylation product and/or acylation product. The product exits the process microchannel 410 as indicated by arrow 416. The flow of heat exchange fluid through the heat exchange channel 420 may be co-current or counter-current to the flow of fluid through the process microchannel 410. Alternatively, the heat exchange channel 420 could be oriented to provide for the flow of heat exchange fluid in a direction that would be cross-current to the flow of fluid through the process microchannel 410. The repeating unit 400 illustrated in FIG. 8 may occur once within the microchannel reactor core 102 or it may be repeated any number of times, for example, two, three, four, five, ten, twenty, fifty, one hundred, hundreds, one thousand, thousands, ten thousand, tens of thousands, one hundred thousand, hundreds of thousands or millions of times.

The repeating unit 400A illustrated in FIG. 9 is similar to the repeating unit 400 illustrated in FIG. 8 with the exception that the repeating unit 400A further comprises staged addition microchannel 440 and apertured section 450. A common wall 441 separates process microchannel 410 and staged addition microchannel 440. The apertured section 450, which in one embodiment contains apertures 452 formed in sheet or plate 456, is positioned in common wall 441. The process microchannel 410 includes reaction zone 412, which is adjacent to apertured section 450. The first reactant feed stream flows into process microchannel 410, as indicated by the arrow 414, and into the reaction zone 412. The second reactant feed stream flows into staged addition microchannel 440, as indicated by arrow 442, and from the staged addition microchannel 440 through apertures 452 into reaction zone 412, as indicated by arrows 454. The liquid catalyst may be premixed with the first reactant feed stream and/or the second reactant feed stream. The direction of flow of the second reactant feed stream in the staged addition microchannel 440, as indicated by arrow 442, is concurrent with the direction of flow of the first reactant feed stream in the process microchannel 410, as indicated by arrow 414; alternatively, the flow of the second reactant feed stream in the staged addition microchannel 440 may be counter-current or cross-current relative to the flow of the first reactant feed stream in the process microchannel 410. The first reactant feed stream and the second reactant feed stream contact each other in the reaction zone 412 and react to form the desired alkylation product and/or acylation product. The product exits the process microchannel 410, as indicated by arrow 416. The product exiting the process microchannel 410 flows through the product footer 106 and out of the reactor, as indicated by arrow 116. Heat exchange fluid flows from heat exchange manifold 108 through heat exchange channel 420 and then back to heat exchange manifold 108. The flow of heat exchange fluid through the heat exchange channel 420 may be co-current or counter-current to the flow of fluid flowing through the process microchannel 410. Alternatively, the heat exchange channel 420 could be oriented to provide for the flow of the heat exchange fluid in a direction that would be cross-current to the flow of fluid through the process microchannel 410.

Figure 10:
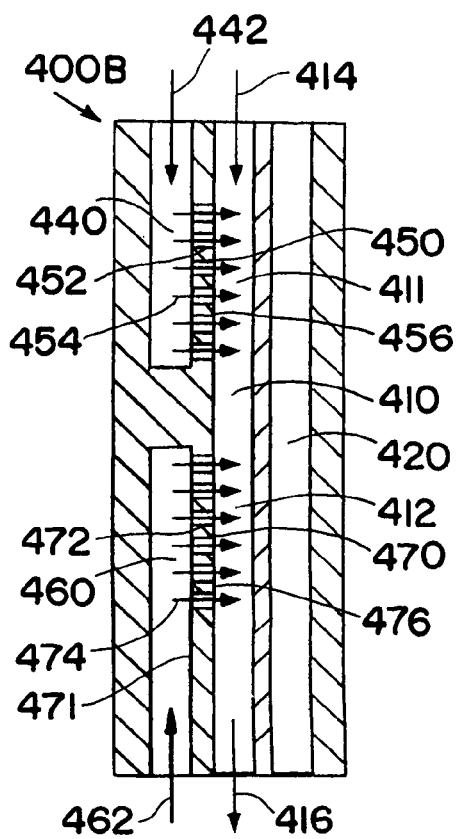
FIG. 10 is a schematic illustration of another alternate embodiment of a repeating unit comprising a process microchannel, staged addition microchannel, a staged addition liquid catalyst microchannel, and a heat exchange channel that may be used in the microchannel reactor core of the microchannel reactor illustrated in FIG. 2.

The repeating unit 400B illustrated in FIG. 10 is similar to the repeating unit 400A illustrated in FIG. 9 with the exception that the repeating unit 400B further comprises staged addition liquid catalyst microchannel 460 and apertured section 470. A common wall 471 separates process microchannel 410 and staged addition liquid catalyst microchannel 460. The apertured section 470, which in one embodiment contains apertures 472 formed in sheet or plate 476, is positioned in common wall 471. The process microchannel 410 has a mixing zone 411 adjacent to apertured section 450, and a reaction zone 412 adjacent to apertured section 470. The mixing zone 411 is upstream from the reaction zone 412. The first reactant feed stream flows into the process microchannel 410, as indicated by arrow 414, and into the mixing zone 411. The second reactant feed stream flows into staged addition microchannel 440, as indicated by arrow 442, and from the staged addition microchannel 440 through apertures 452 into mixing zone 411, as indicated by arrows 454. The direction of the flow of the second reactant feed stream in the staged addition microchannel 440, as indicated by arrow 442, is concurrent with the direction of the flow of the first reactant feed stream in the process microchannel 410, as indicated by arrow 414; alternatively, the flow of the second reactant feed stream in the staged addition microchannel 440 may be counter-current or cross-current relative to the flow of the first reactant feed stream in the process microchannel 410. The first reactant feed stream and the second reactant feed stream contact each other in the mixing zone 411 and form a reactant mixture. The reactant mixture flows from the mixing zone 411 to the reaction zone 412. The liquid catalyst flows into the staged addition liquid catalyst microchannel 460, as indicated by arrow 462, and from the staged addition liquid catalyst channel 460 through apertures 472 into reaction zone 412, as indicated by arrows 474. The direction of flow of the liquid catalyst in the staged addition liquid catalyst microchannel 460, as indicated by arrow 462, is counter-current to the direction of flow of the first reactant feed stream in the process microchannel 410, as indicated by arrow 414; alternatively, the flow of the liquid catalyst in the staged addition liquid channel 460 may be co-current or cross-current relative to the flow of the first reactant feed stream in the process microchannel 410. The liquid catalyst contacts the reactant mixture in the reaction zone 412. The reactant mixture reacts to form the desired alkylation product and/or acylation product. The product exits the process microchannel 410, as indicated by arrow 416. The product exiting the process microchannel 410 flows through the product footer 106 and out of the reactor, as indicated by arrow 116. Heat exchange fluid flows from the heat exchange manifold 108 through heat exchange channel 420 and then back to heat exchange manifold 108. The flow of heat exchange fluid through the heat exchange channel 420 may be co-current or counter-current to the flow of fluid flowing through the process microchannel 410. Alternatively, the heat exchange channel 420 could be oriented to provide for the flow of the heat exchange fluid in a direction that would be cross-current to the flow of fluid through the process microchannel 410.

Figure 35:
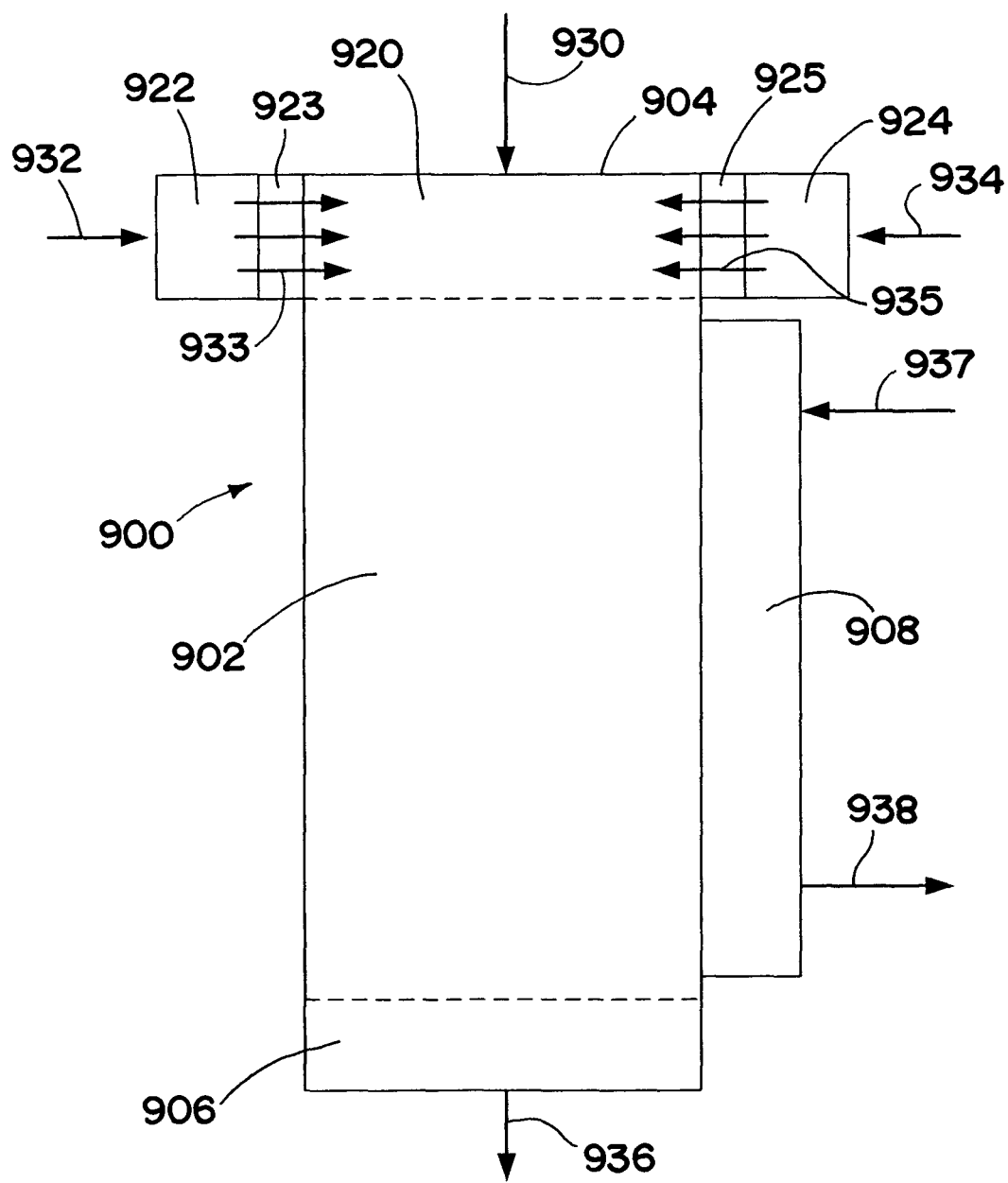
FIG. 35 is a schematic illustration of an alternate embodiment of the inventive process in a particular form wherein the first reactant feed streams and the second reactant feed streams flow into a microchannel reactor, contact each other in a feed streams header and form a reaction mixture, the reaction mixture then flows from the feed stream header through process microchannels in a microchannel reactor core in contact with a catalyst to form the desired alkylation and/or acylation product.
Figure 36:
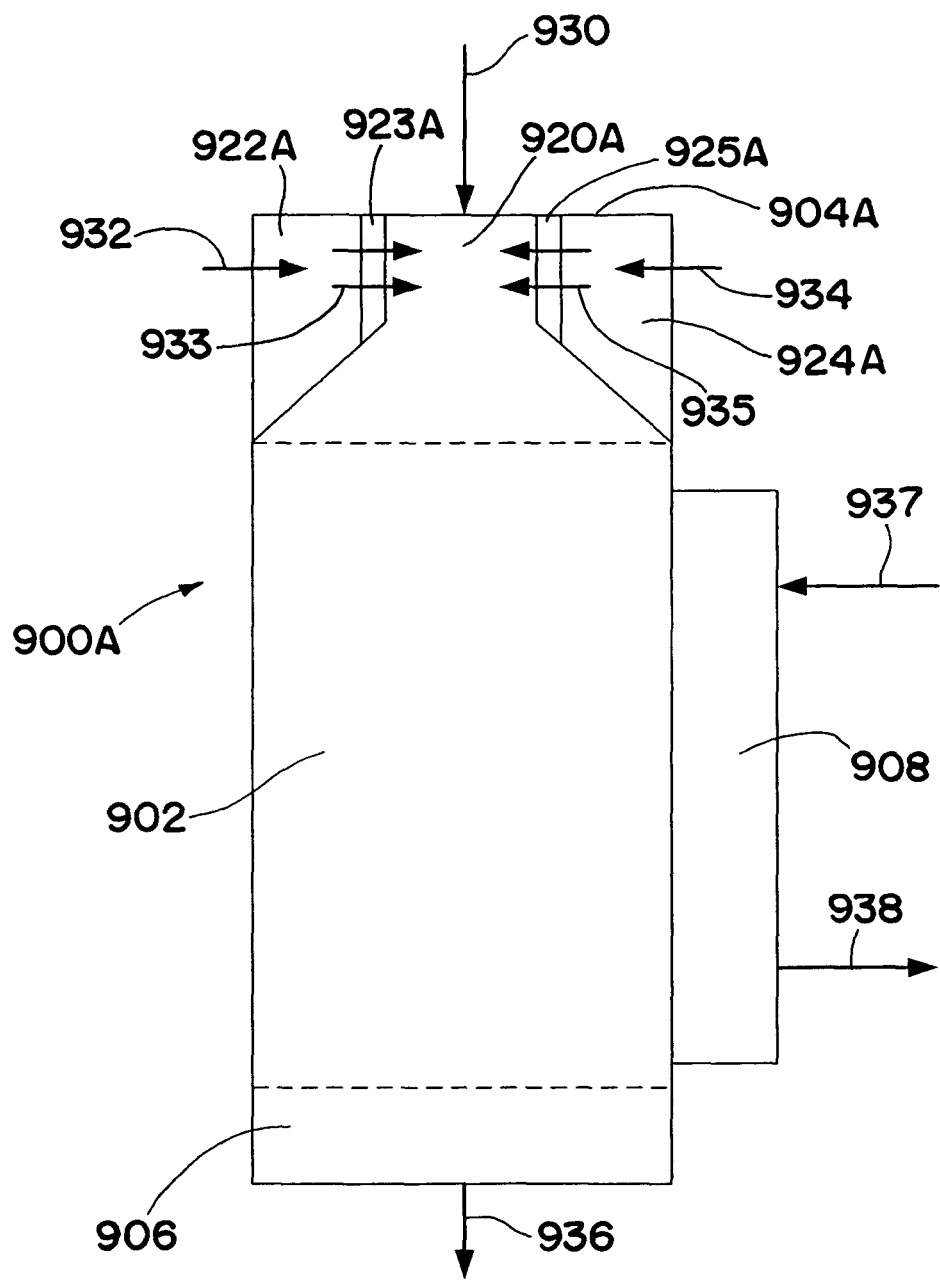
FIG. 36 is a schematic illustration of another alternate embodiment of the inventive process in a particular form wherein the first reactant feed streams and the second reactant feed streams flow into a microchannel reactor, contact each other in a feed streams header and form a reaction mixture, the reaction mixture then flows through process microchannels in a microchannel reactor core in contact with a catalyst to form the desired alkylation and/or acylation product.

In one embodiment, the inventive process may be conducted in a microchannel reactor as illustrated, for example, in FIGS. 35-41. Referring to FIG. 35, the process may be conducted using microchannel reactor 900, which includes microchannel reactor core 902, feed stream header 904, product footer 906 and heat exchange manifold 908. The microchannel reactor 900A illustrated in FIG. 36 is the same as the microchannel reactor 900 illustrated in FIG. 32 with the exception that the microchannel reactor 900A employs feed stream header 904A rather than feed streams header 904. Feed streams headers 904 and 904A are similar in design and operation. The design and operation of these headers is described in more detail below. The reactor core 902 in microchannel reactors 900 and 900A may contain one or more of the repeating units 910, 912 and/or 914 illustrated in FIGS. 37-39, respectively.

Feed streams header 904 includes first reactant zone 920, second reactant zones 922 and 924, and apertured sections 923 and 925. Apertured section 923 is positioned between first reactant zone 920 and second reactant zone 922. Apertured section 925 is positioned between first reactant zone 920 and second reactant zone 924. Feed streams header 904A is similarly constructed and includes first reactant zone 920A, second reactant zones 922A and 924A, and apertured sections 923A and 925A.

In operation, the first reactant feed streams flows into the first reactant zone 920 as indicated by arrow 930. The second reactant feed streams flows into second reactant zones 922 and 924 as indicated by arrows 932 and 934, respectively. The second reactant feed streams flows from second reactant zone 922 through apertured section 923 into first reactant zone 920 as indicated by arrows 933. The second reactant feed streams also flows from second reactant zone 924 through apertured section 925 into first reactant zone 920 as indicated by arrows 935. In the first reactant zone 920, the second reactant feed streams disperses into the first reactant feed streams to form a reaction mixture. The reaction mixture that is formed in the first reactant zone 920 may have a continuous phase with the first reactant feed streams forming the continuous phase, and a dispersed phase with the second reactant feed streams forming the dispersed phase. The dispersed phase may be in the form of gas bubbles and/or liquid droplets dispersed in the continuous phase. The second reactant feed streams may dissolve in the second reactant feed streams to form a homogeneous mixture or a solution. Alternatively, the first reactant feed stream may flow from the second reactant zones 922 and 924 through the apertures 923 and 925, respectively, into the first reactant zone 920 and contact the second reactant feed streams in the first reactant zone 920 to form the reaction mixture. The reaction mixture flows through the reaction zone 902, and reacts to form the desired alkylation and/or acylation product. The product flows into product footer 906 and out of the microchannel reactor 900 as indicated by arrow 936. Heat exchange fluid enters the heat exchange manifold 908, as indicated by arrow 937, circulates through the reactor core 902, returns to the heat exchange manifold 908, and exits the heat exchange manifold 908 as indicated by arrow 938.

The operation of microchannel reactor 900A is similar to that of microchannel 900. The first reactant feed streams flows into the first reactant zone 920A as indicated by arrow 930. The second reactant feed streams flows into second reactant zones 922A and 924A as indicated by arrows 932 and 934, respectively. The second reactant feed streams flows from second reactant zone 922A through apertured section 923A into first reactant zone 920A as indicated by arrows 933. The second reactant feed streams also flows from second reactant zone 924A through apertured section 925A into first reactant zone 920A as indicated by arrows 935. In the first reactant zone 920, the second reactant feed streams disperses into the first reactant to form a reaction mixture. The reaction mixture that is formed in the first reactant zone 920 may have a continuous phase with the first reactant forming the continuous phase, and a dispersed phase with the second reactant forming the dispersed phase. The dispersed phase may be in the form of gas bubbles and/or liquid droplets dispersed in the continuous phase. The reaction mixture may be in the form of a homogeneous mixture or a solution. Alternatively, the first reactant feed stream may flow from the second reactant zones 922A and 924A through the apertures 923A and 925A, respectively, into the first reactant zone 920A and contact the second reactant feed streams in the first reactant zone 920A to form the reaction mixture. The reaction mixture flows through the reaction zone 902, and reacts to form the desired alkylation and/or acylation product. The product flows into product footer 906 and out of the microchannel reactor 900 as indicated by arrow 936. Heat exchange fluid enters the heat exchange manifold 908, as indicated by arrow 937, circulates through the reactor core 902, returns to the heat exchange manifold 908, and exits the heat exchange manifold 908 as indicated by arrow 938.

The microchannel reactors 900 and 900A may be used in combination with one or more storage vessels, pumps, valves, manifolds, microprocessors, flow control devices, and the like, which are not shown in the drawings, but would be apparent to those skilled in the art.

Figure 39:
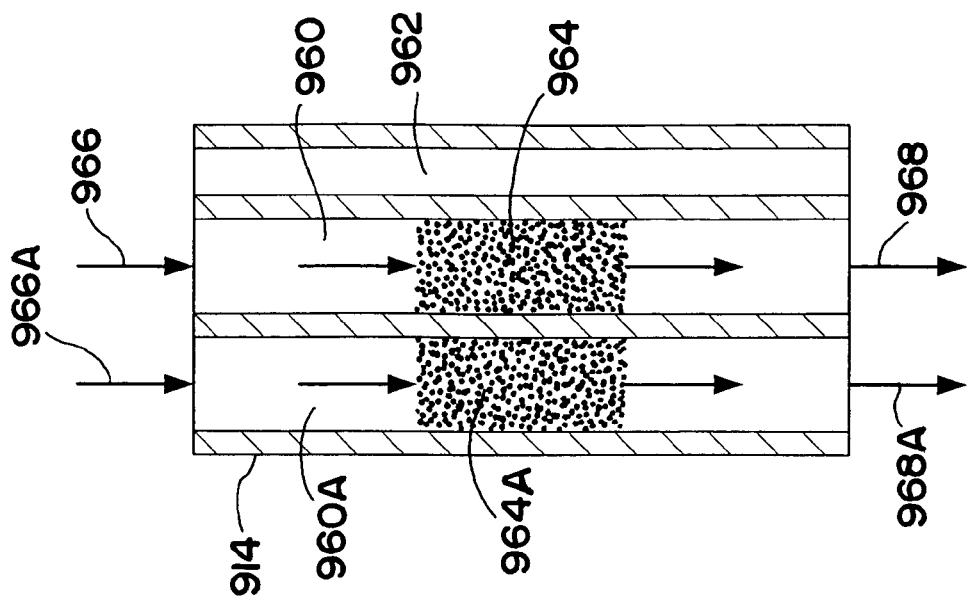
FIG. 39 is a schematic illustration of a repeating unit comprising adjacent process microchannels and a heat exchange channel which may be used in the microchannel reactor illustrated in FIG. 35 or FIG. 36.
Figure 38:
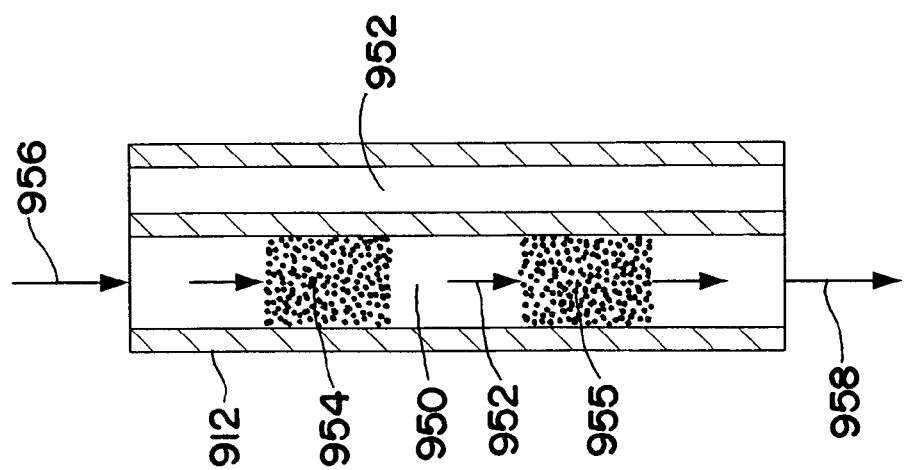
FIG. 38 is a schematic illustration of a repeating unit comprising a process microchannel and a heat exchange channel that may be used in the microchannel reactor illustrated in FIG. 35 or FIG. 36, the process microchannel containing two reaction zones.
Figure 37:
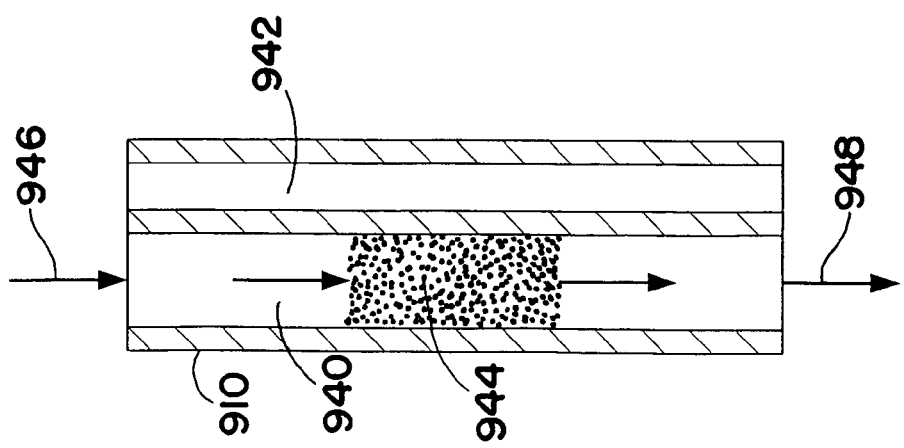
FIG. 37 is a schematic illustration of a repeating unit comprising a process microchannel and a heat exchange channel that may be used in the microchannel reactor illustrated in FIG. 35 or FIG. 36, the process microchannel containing a reaction zone.

Repeating units that may be used in the reactor core 902 are illustrated in FIGS. 37-39. Referring to FIG. 37, repeating unit 910 comprises process microchannel 940, heat exchange channel 942, and reaction zone 944. The reaction zone 944 contains a catalyst. The reaction mixture flows from the feed streams header 904 or 904A into the process microchannel 940 as indicated by arrow 946. The reaction mixture contacts the catalyst in the reaction zone 944 and reacts to form the desired alkylation and/or acylation product. The product flows from the reaction zone 944 out of the process microchannel 940 as indicated by arrow 948. Heat exchange fluid flows in heat exchange channel 942 and exchanges heat with the process microchannel 940. The exchange of heat between the heat exchange channel 942 and process microchannel 940 may result in a cooling of the process microchannel 940 or a heating of the process microchannel 940. The heat exchange fluid may flow in the heat exchange channel 942 in a direction that is concurrent, countercurrent or cross-current relative to the direction of flow of fluid in the process microchannel 940.

The repeating unit 912 illustrated in FIG. 38 is similar to the repeating unit 910 illustrated in FIG. 37 with the exception that the repeating unit 912 includes two reaction zones 954 and 955 in the process microchannel rather than one reaction zone. Repeating unit 912 comprises process microchannel 950 and heat exchange channel 952. The catalyst that may be employed in the reaction zones 954 and 955 may be the same, or it may be different. For example, a first reaction may be conducted in the reaction zone 954, and a different reaction may be conducted in the reaction zone 955. In operation, the reaction mixture flows into process microchannel 950 from feed streams header 904 or 904A as indicated by arrow 956. The multiphase reaction mixture flows through reaction zone 954 and reacts to form an intermediate product. The intermediate product then flows into reaction zone 955 as indicated by arrow 952. The final alkylation and/or acylation product is formed in reaction zone 955 and exits the repeating unit 912 as indicated by arrow 958. The product flows from the repeating unit 912 to and through the product footer 906 and out of the microchannel reactor 900 or 900A as indicated by arrow 936.

Figure 34:
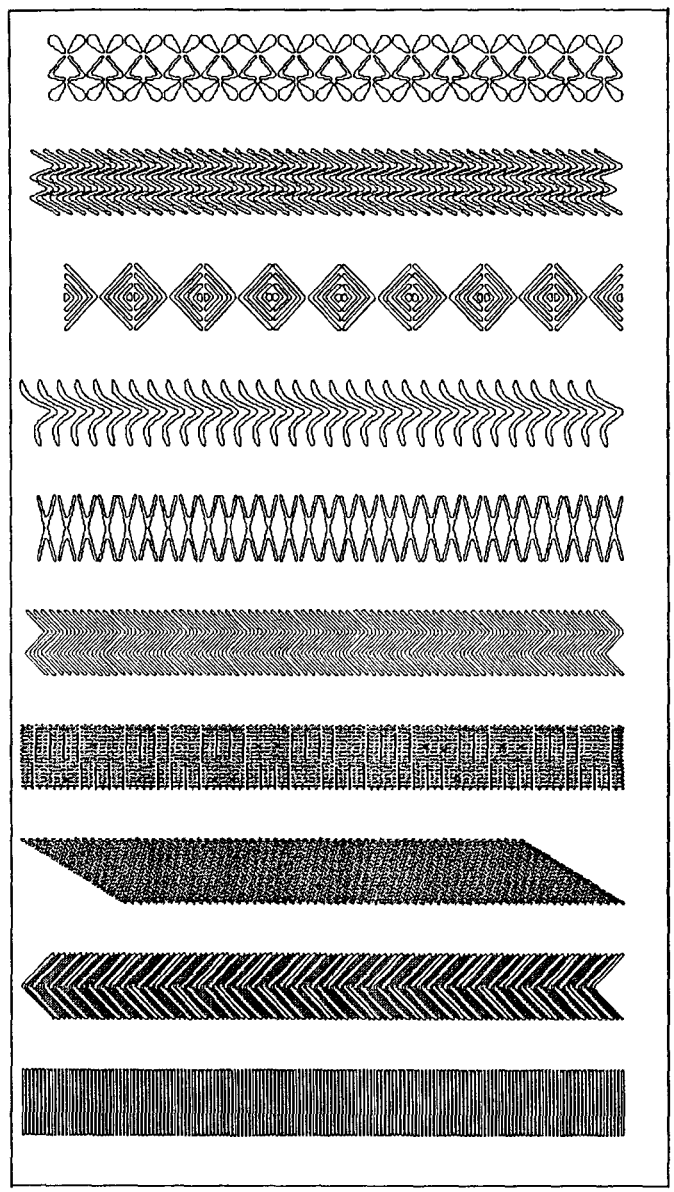

The repeating unit 914 illustrated in FIG. 36 is similar to the repeating unit 910 illustrated in FIG. 34 with the exception that the repeating unit 914 includes two process microchannels 960 and 960A rather than one process microchannel. Repeating unit 914 comprises process microchannels 960 and 960A and heat exchange channel 962. The process microchannels 960 and 960A contain reaction zones 964 and 964A, respectively. In operation, the reaction mixture flows into process microchannels 960 and 960A from feed streams header 904 or 904A as indicated by arrows 966 and 966A, respectively. The reaction mixture flows through reaction zones 964 and 964A and reacts to form the desired alkylation and/or acylation product. The product exits the repeating unit 914 as indicated by arrows 968 and 968A. The product flows from the repeating unit 914 to and through the product footer 906 and out of the microchannel reactor 900 or 900A as indicated by arrow 936.

Figure 40:
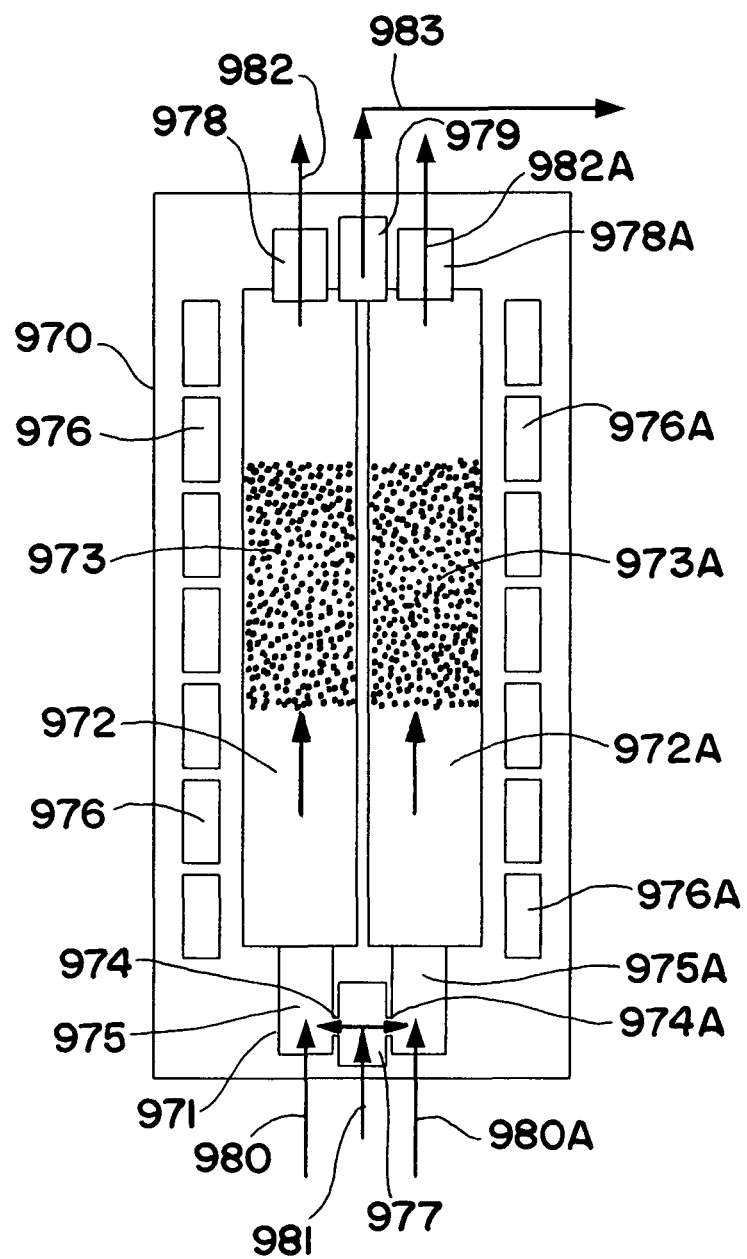
FIG. 40 is a schematic illustration of a repeating unit comprising adjacent process microchannels, heat exchange zones adjacent to the process microchannels, and a manifold for dispersing the second reactant feed streams into the first reactant feed streams to form a reaction mixture, the reaction mixture flowing through reaction zones in the process microchannels to form the desired alkylation and/or acylation product.
Figure 41:
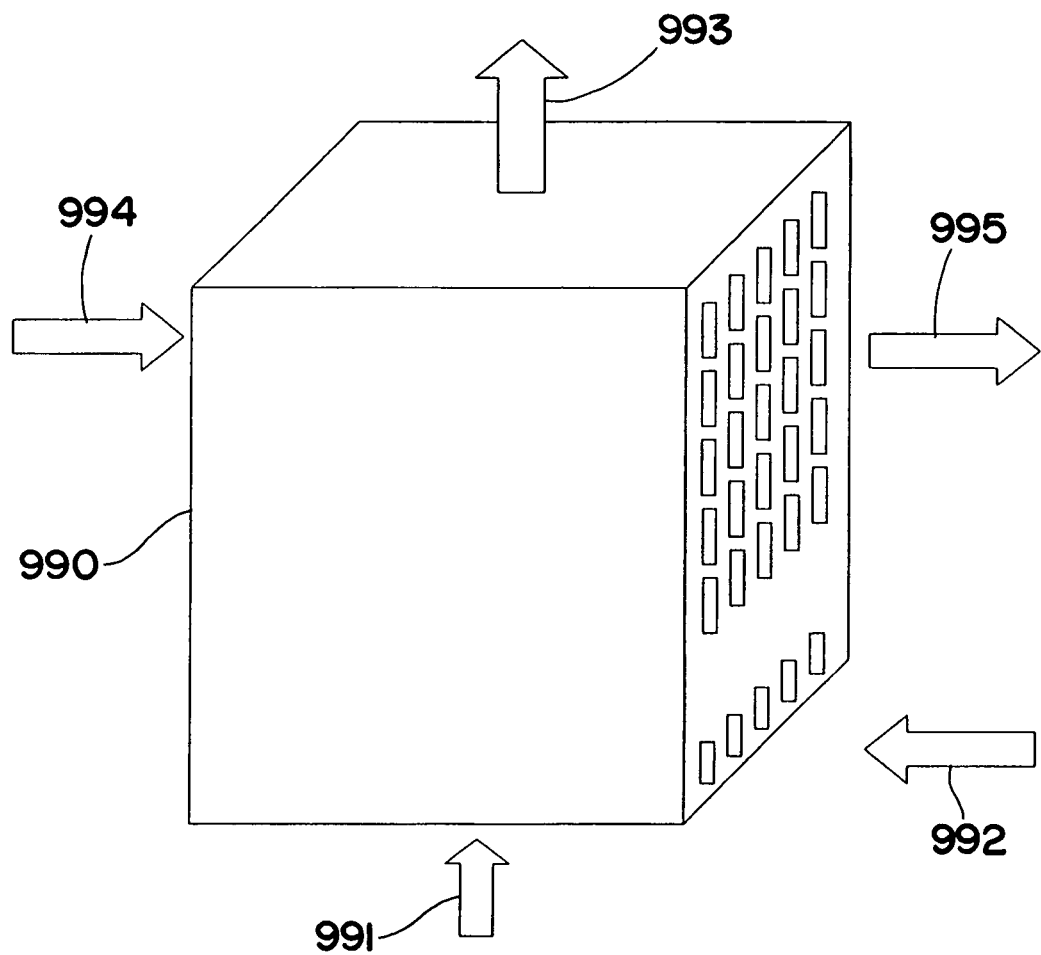
FIG. 41 is a schematic illustration of a microchannel reactor for housing one or more of the repeating units illustrated in FIG. 40.

In one embodiment, the inventive process may be conducted in a microchannel reactor as illustrated, for example, in FIGS. 40 and 41. Referring to FIG. 40, the process may be conducted using repeating unit 970 which includes process microchannels 972 and 972A, and heat exchange channels 976 and 976A. The repeating unit 970 also includes an inlet manifold 971 which includes first reactant zones 975 and 975A and second reactant zone 977. Apertured sections 974 and 974A are positioned between second reactant zone 977 and first reactant zones 975 and 975A, respectively. The repeating unit 970 also includes product footers 978 and 978A, and an optional gas disengagement footer 979. In operation, the first reactant feed streams flows into the first reactant zones 975 and 975A as indicated by arrows 980 and 980A. The second reactant feed streams flows into second reactant zone 977 as indicated by arrow 981 and from there through apertured sections 974 and 974A into first reactant zones 975 and 975A, respectively. The reaction mixture is formed in first reactant zones 975 and 975A. The reaction mixture may contain the first reactant in the form of a continuous phase and the second reactant in the form of a dispersed phase. The dispersed phase may be in the form of gas bubbles and/or liquid droplets. The reaction mixture may be in the form of a homogeneous mixture or a solution. Alternatively, the first reactant feed streams may flow from the second reactant zone 977 through the apertured sections 974 and 974A into the first reactant zones 975 and 975A, respectively, and contact the second reactant feed streams in the first reactant zones 975 and 975A to form the reaction mixture. The reaction mixture flows into the reaction zones 973 and 973A, reacts to form the desired alkylation and/or acylation product and flows to and through the product footers 978 and 978A and out of the microchannel repeating unit 970 as indicated by arrows 982 and 982A. Optionally, gases may be disengaged from the product. The disengaged gases may exit the microchannel repeating unit 970 through the gas disengagement footer 979 as indicated by arrow 983. Surface features positioned within the process microchannels 972 and 972A downstream of the reaction zones 973 and 973A may be used to facilitate separation of gases from the product. Surface features that may be used are discussed in greater detail below. In one embodiment, the disengagement sections within the process microchannels may take the form of a pore throats, where liquid wets and fills small pores or structures such that capillary forces hold the liquid in the pores or structures. The capillary force of the liquid may exceed the breakthrough pressure of the gas, such that gas cannot be pulled into the pores or structures. Examples of pore throat structures that may be used are disclosed in U.S. patent application Ser. No. 11/177,941 filed Jul. 8, 2005, which is incorporated herein by reference.

FIG. 41 illustrates microchannel reactor 990 which may be used to house one or more of the microchannel repeating units 970 illustrated in FIG. 40. With the microchannel reactor 990, the first reactant feed streams enters the microchannel reactor as indicated by arrow 991, and the second reactant feed streams enters as indicated by arrow 992. The alkylation and/or acylation product exits the microchannel reactor 990 as indicated by arrow 993. Heat exchange fluid flows into the microchannel reactor 990 as indicated by arrow 994 and exits the microchannel reactor 990 as indicated by arrow 995.

In one embodiment, the apertured section (350, 450, 470) may be positioned in one or more sidewalls of the process microchannel (310, 410). The apertured section may extend along part of or the entire axial length of the process microchannel. In one embodiment, the apertured section may extend along at least about 10% of the axial length of the process microchannel, and in one embodiment at least about 20% of the axial length of the process microchannel, and in one embodiment at least about 35% of the axial length of the process microchannel, and in one embodiment at least about 50% of the axial length of the process microchannel, and in one embodiment at least about 65% of the axial length of the process microchannel, and in one embodiment at least about 80% of the axial length of the process microchannel, and in one embodiment at least about 95% of the axial length of the process microchannel, and in one embodiment from about 5% to about 100% of the axial length of the process microchannel, and in one embodiment from about 10% to about 95% of the axial length of the process microchannel, and in one embodiment from about 25% to about 75% of the axial length of the process microchannel, and in one embodiment from about 40% to about 60% of the axial length of the process microchannel.

Figure 14:
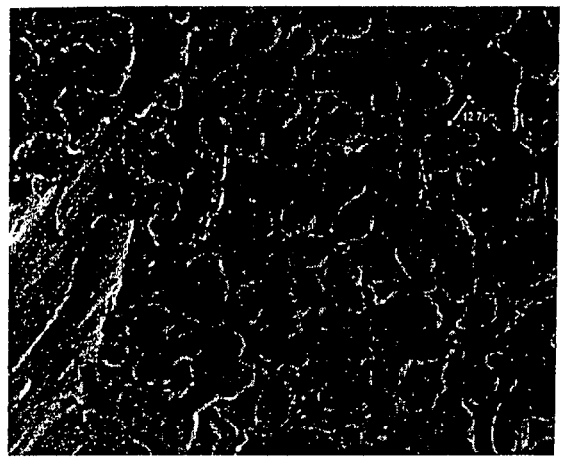
FIG. 14 is a scanning electron microscopic (SEM) image of a porous stainless steel substrate before being heat treated; this substrate may be useful for making an apertured section for a process microchannel used with the inventive process.
Figure 15:
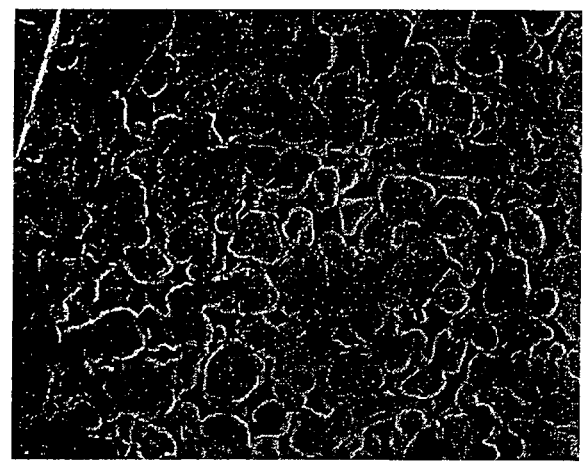
FIG. 15 is an SEM image of the substrate illustrated in FIG. 14 after being heat treated; this substrate may be useful for making an apertured section for a process microchannel used with the inventive process.

The apertures (352, 452, 472) in the apertured sections (350, 450, 470, 923, 925, 923A, 925A, 974, 974A) may be of sufficient size to permit the flow of the indicated fluids through the apertured sections. The apertures may be referred to as pores or jets. The apertured sections (350, 450, 470, 923, 925, 923A, 925, 974, 974A) may have thicknesses in the range from about 0.01 to about 50 mm, and in one embodiment about 0.05 to about 10 mm, and in one embodiment about 0.1 to about 2 mm. The apertures (352, 452, 472) in the apertured sections (350, 450, 470, 923, 925, 923A, 925A, 974, 974A) may have average diameters in the range up to about 5000 microns, and in one embodiment in the range from about 0.001 to about 500 microns, and in one embodiment from about 0.05 to about 50 microns, and in one embodiment from about 0.1 to about 50 microns. In one embodiment, the apertures may have average diameters in the range from about 0.5 to about 10 nanometers (nm), and in one embodiment about 1 to about 10 nm, and in one embodiment about 5 to about 10 nm. The number of apertures in the apertured sections may be in the range from about 10 to about $5\times10^8$ apertures per square centimeter, and in one embodiment about 1 to about $1\times10^6$ apertures per square centimeter. The apertures may or may not be isolated from each other. A portion or all of the apertures may be in fluid communication with other apertures within the apertured section; that is, a fluid may flow from one aperture to another aperture. The ratio of the thickness of the apertured sections (350, 450, 470) to the length of the apertured sections along the flow path of the fluids flowing through the process microchannels (310, 410) may be in the range from about 0.001 to about 1, and in one embodiment about 0.01 to about 1, and in one embodiment about 0.03 to about 1, and in one embodiment about 0.05 to about 1, and in one embodiment about 0.08 to about 1, and in one embodiment about 0.1 to about 1. The apertured sections (350, 450, 470, 923, 925, 923A, 925, 974, 974A) may be constructed of any material that provides sufficient strength and dimensional stability to permit the operation of the inventive process. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; microporous carbon, including carbon nanotubes or carbon molecular sieves; zeolites; or a combination of two or more thereof. The apertures may be formed using known techniques such as laser drilling, microelectro machining system (MEMS), lithography electrodeposition and molding (LIGA), electrical sparkling or electrochemical etching. The apertures may be formed using techniques used for making structured plastics, such as extrusion, or membranes, such as aligned carbon nanotube (CNT) membranes. The apertures may be formed using techniques such as sintering or compressing metallic powder or particles to form tortuous interconnected capillary channels and the techniques of membrane fabrication. The apertures may be reduced in size from the size provided by any of these methods by the application of coatings over the apertures internal side walls to partially fill the apertures. The selective coatings may also form a thin layer exterior to the porous body that provides the smallest pore size adjacent to the continuous flow path. The smallest average pore opening may be in the range from about one nanometer to about several hundred microns depending upon the desired droplet size for the emulsion. The apertures may be reduced in size by heat treating as well as by methods that form an oxide scale or coating on the internal side walls of the apertures. These techniques may be used to partially occlude the apertures to reduce the size of the openings for flow. FIGS. 14 and 15 show a comparison of SEM surface structures of a stainless steel porous substrate before and after heat treatment at the same magnification and the same location. FIG. 14 shows the surface before heat treating and FIG. 15 shows the surface after heat treating. The surface of the porous material after the heat treatment has a significantly smaller gap and opening size. The average distance between the openings is correspondingly increased.

Figure 16:
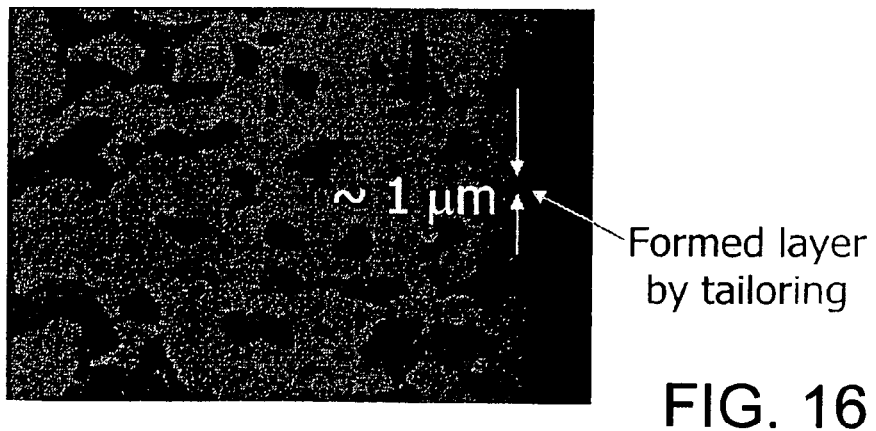
FIG. 16 is an SEM image of a tailored porous substrate which may be useful for making an apertured section for a process microchannel used with the inventive process.

The apertured sections (350, 450, 470, 923, 925, 923A, 925A, 974, 974A) may be made from a metallic or nonmetallic porous material having interconnected channels or pores of an average pore size in the range from about 0.01 to about 200 microns. These pores may function as the apertures (352, 452, 472). The porous material may be made from powder or particulates so that the average inter-pore distance is similar to the average pore size. When very small pore sizes are used, the inter-pore distance may also be very small and droplets or bubbles may merge at the surface of the side of the process microchannels (310, 410) to form larger droplets or bubbles that are not desired due to the fact that they interfere with proper mixing. The porous material may be tailored by oxidization at a high temperature in the range from about 300° C. to about 1000° C. for a duration of about 1 hour to about 20 days, or by coating a thin layer of another material such as alumina by SOL coating or nickel using chemical vapor deposition over the surface and the inside of pores to block the smaller pores, decrease pore size of larger pores, and in turn increase the interpore distance. As such, the merger of droplets may be reduced or eliminated and the formation of smaller droplets may be permitted. An SEM image of a tailored substrate or apertured section is shown in FIG. 16.

The making of substrates for use as apertured sections (350, 450, 470, 923, 925, 923A, 925A, 974, 974A) with sufficiently small micro-scale apertures or pores (352, 452, 472) to provide reactant mixtures having droplet sizes smaller than about one micron can be problematic. One of the reasons for this lies in the fact that relatively high surface roughness occurs with untreated regular porous materials such as a metallic porous substrates made from powder/particles by compression and/or sintering. These metallic porous substrates typically do not have the required pore size in the surface region when a given nominal pore size is lower than a certain value. While the bulk of the porous material may have the specified nominal pore size, the surface region is often characterized by merged pores and cavities of much larger sizes. This problem can be overcome by tailoring these substrates to provide for the desired pore size and inter-pore distance in the surface region. This may be done by removing a surface layer from the porous substrate and adding a smooth new surface with smaller openings. The droplet size in the reactant mixture that may be formed using these tailored substrates may be reduced without increasing the pressure drop across the substrate. Since direct grinding or machining of the porous surface may cause smearing of the surface structure and blockage of the pores, the porous structure may be filled with a liquid filler, followed by solidification and mechanical grinding/polishing. The filler is then removed to regain the porous structure of the material. The filler may be a metal with a low melting point such as zinc or tin or the precursor of a polymer such as an epoxy. The liquid filling and removing steps may be assisted by the use of a vacuum.

Grinding/polishing may be effected using a grinding machine and a grinding powder. Metal filler removal may be effected by melting and vacuum suction, or by acid etching. Epoxies or other polymers may be removed by solvent dissolution or by burn-off in air.

In one embodiment, the apertured sections (350, 450, 470, 923, 925, 923A, 925A, 974, 974A) may have a nominal aperture or pore size of about 0.1 micron and the dimensions of about 0.010×1×1.5 inches (0.254×25.4×38.1 mm). These apertured sections may be constructed of stainless steel 316L and supplied by Mott Corporation of Farmington, Conn. under Catalogue No. 1110-12-12-018-01-A.

Figure 17:
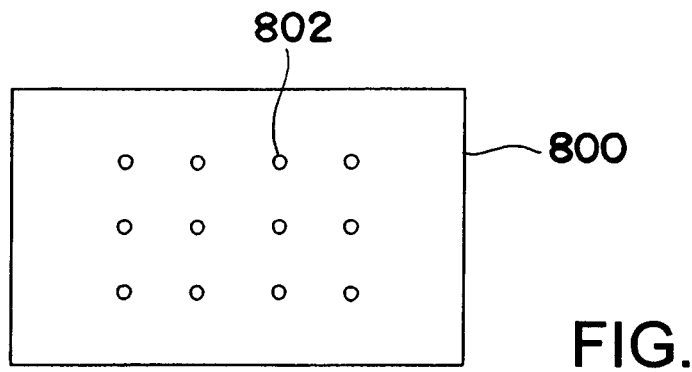
FIG. 17 is a plan view of an apertured sheet which may be useful in making an apertured section for a process microchannel used with the inventive process.
Figure 18:
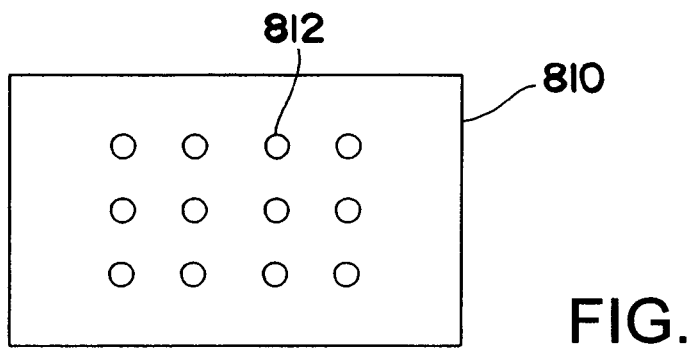
FIG. 18 is a plan view of an apertured sheet or plate which may be useful in making an apertured section for a process microchannel used with the inventive process.
Figure 19:
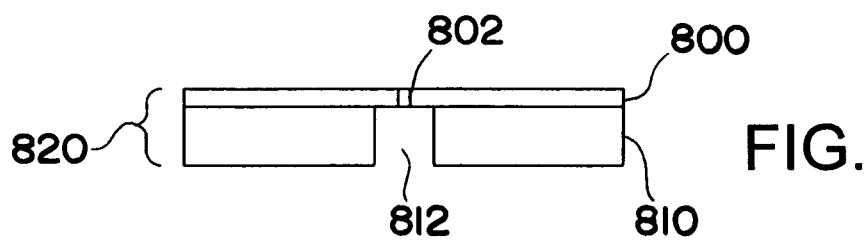
FIG. 19 is an illustration of a relatively thin apertured sheet overlying a relatively thick apertured sheet or plate which may be useful in making an apertured section for a process microchannel used with the inventive process.

Referring to FIGS. 17-19, the apertured sections (350, 450, 470, 923, 925, 923A, 925A, 974, 974A), in one embodiment, may comprise a relatively thin sheet 800 containing relatively small apertures 802, and a relatively thick sheet or plate 810 containing relatively large apertures 812. The apertures 812 may be aligned with or connected to the apertures 802. The relatively thin sheet 800 overlies and is bonded to the relatively thick sheet or plate 810, the relatively thin sheet 800 facing the interior of process microchannel (310, 410) and the relatively thick sheet 810 facing the interior of the staged addition microchannels (340, 440) or staged addition liquid catalyst channel (460). The relatively thin sheet 800 may be bonded to the relatively thick sheet 810 using any suitable procedure (e.g., diffusion bonding) to provide a composite construction 820 with enhanced mechanical strength. The relatively thin sheet 800 may have a thickness in the range from about 0.001 to about 0.5 mm, and in one embodiment about 0.05 to about 0.2 mm. The relatively small apertures 802 may have any shape, for example, circular, triangular or rectangular. The relatively small apertures 802 may have an average diameter in the range from about 0.05 to about 500 microns, and in one embodiment from about 0.05 to about 200 microns. The relatively thick sheet or plate 810 may have a thickness in the range from about 0.1 to about 5 mm, and in one embodiment about 0.1 to about 2 mm. The relatively large apertures 812 may have any shape, for example, circular, triangular or rectangular. The relatively large apertures 812 may have an average diameter in the range from about 0.1 to about 4000 microns, and in one embodiment about 1 to about 2000 microns, and in one embodiment about 10 to about 1000 micron. The total number of apertures 802 in sheet 800 and the total number of apertures 812 in sheet or plate 810 may be in the range from about 2 to about 10000 apertures per square centimeter, and in one embodiment from about 2 to about 1000 apertures per square centimeter. The sheet 800 and the sheet or plate 810 may be constructed of any of the materials described above as being useful for constructing the apertured sections (350, 450, 470, 923, 925, 923A, 925A, 974, 974A). The apertures 802 and 812 may be aligned or connected in such a manner that fluid flowing through the apertured sections (350, 450, 470, 923, 925, 923A, 925A, 974, 974A) flows initially through the apertures 812 then through the apertures 802. The relatively short passageway for the fluid to flow through the relatively small apertures 802 enables the fluid to flow through the apertures 802 with a relatively low pressure drop as compared to the pressure drop that would occur if the passageway in the apertures had a length equal to the combined length of apertures 802 and 812.

Figure 20:
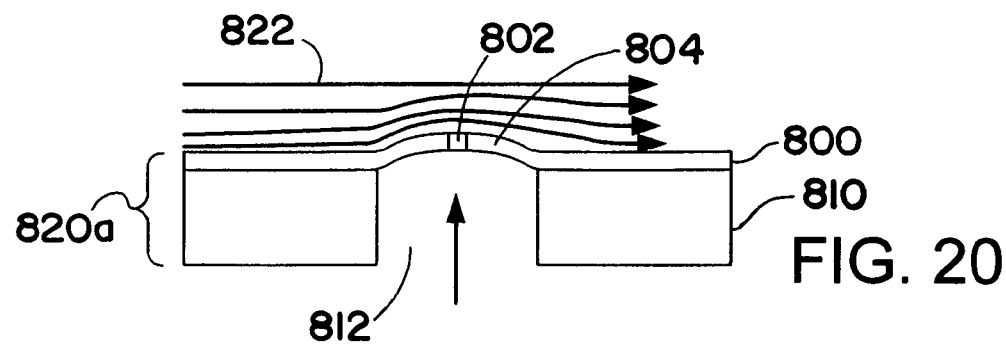
FIG. 20 is an illustration of a relatively thin apertured sheet overlying a relatively thick apertured sheet or plate which may be useful in making an apertured section for a process microchannel used with the inventive process.

In the embodiment illustrated in FIG. 20, the composite construction 820a may have the same design as illustrated in FIG. 19 with the exception that convex portion 804 of the relatively thin sheet 800 covering the aperture 812 is provided. Convex portion 804 provides increased local shear force in the adjacent channel. The directional arrows 822 in FIG. 20 show the flow of liquid in the channel adjacent to the aperture 802. The increased local shear force leads to a smaller droplet size for the fluid flowing through the aperture 802.

Figure 21:
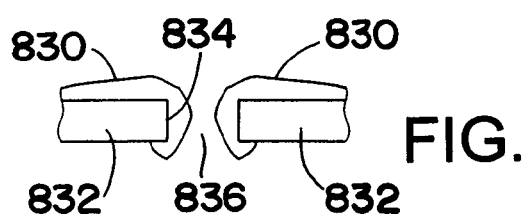
FIG. 21 is an illustration of an alternate embodiment of an aperture that may be used in the apertured section of a process microchannel used with the inventive process, the aperture having a coating partially filling it and overlying its sidewalls.

In the embodiment illustrated in FIG. 21, a surface coating 830 may be deposited on the surface of sheet or plate 832 and on the internal sidewalls 834 of aperture 836. This coating may provide a facilitated way of reducing the diameter of the apertures (352, 452, 472). The coating material used to form coating 830 may be alumina, nickel, gold, or a polymeric material (e.g., Teflon). The coating 830 may be applied to the sheet or plate 832 using known techniques including chemical vapor deposition, metal sputtering, metal plating, sintering, sol coating, and the like. The effective diameter of the apertures (352, 452, 472) may be controlled by controlling the thickness of the coating 830.

In one embodiment, the apertured sections (350, 450, 470, 923, 925, 923A, 925A, 974, 974A) may be formed from an asymmetric porous material, for example, a porous material having multiple layers of sintered particles. The number of layers may be two, three, or more. An advantage of these multilayered substrates is that they provide enhanced durability and adhesion. Examples include sintered ceramics that have relatively large pores on one side and relatively small pores on the other side. The relatively small pores may have diameters in the range of about 2 to about 10 nm. The relatively small pores may be positioned in a relatively thin layer of the multilayered substrate. The relatively thin layer may have a thickness in the range of about 1 to about 10 microns. The side with the relatively small pores may be placed facing the interior of the process microchannel (310, 410) to take advantage of relatively high shear forces to remove the relatively small droplets of reactants and/or catalyst as they are formed.

The process microchannels (210, 310, 410, 940, 950, 960, 960A), staged addition microchannels (340, 440) and staged addition liquid catalyst microchannels (460) may have at least one internal dimension of height or width of up to about 10 mm, and in one embodiment from about 0.05 to about 10 mm, and in one embodiment about 0.05 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The height or width may range from about 0.15 to about 10 mm, and in one embodiment from about 0.2 to about 10 mm, and in one embodiment from about 0.3 to about 10 mm. The height or width may range from about 0.2 to about 5 mm, and in one embodiment from about 0.2 to about 3 mm, and in one embodiment from about 0.3 to about 2 mm. The other internal dimension of height or width may be of any value, for example, it may range up to about 100 cm, and in one embodiment from about 0.01 to about 100 cm, and in one embodiment from about 0.1 cm to about 100 cm, and in one embodiment from about 0.1 to about 75 cm, and in one embodiment from about 0.1 to about 50 cm, and in one embodiment about 0.2 cm to about 25 cm. The length of the process microchannels, staged addition microchannels and staged addition liquid catalyst microchannels may be of any value, although, as suggested by the drawings, the length of the staged addition microchannels and staged addition liquid catalyst microchannels may be less than the length of the next adjacent process microchannels. The lengths of each of these channels may be in the range up to about 10 m, and in one embodiment from about about 1 cm to about 10 m, and in one embodiment from about 1 cm to about 5 m, and in one embodiment 1 cm to about 2.5 m, and in one embodiment from about 1 cm to about 1 m, and in one embodiment from about 2 cm to about 50 cm, and in one embodiment about 2 to about 25 cm.

In one embodiment, flow and/or mixing within the process microchannels (210, 310, 410, 940, 950, 960, 960A), staged addition microchannels (340, 440), and/or staged addition liquid catalyst microchannels (460) may be enhanced by the use of surface features formed on one, two or more interior walls of such microchannels. The surface features may be in the form of depressions in and/or projections from one or more of the microchannel walls. These surface features may be oriented at angles relative to the direction of flow through the microchannels. The surface features may be aligned at an angle from about 1° to about 89°, and in one embodiment from about 30° to about 75°, relative to the direction of flow. The angle of orientation may be an oblique angle. The angled surface features may be aligned toward the direction of flow or against the direction of flow. The flow of the fluids in contact with the surface features may force one or more of the fluids into depressions in the surface features, while other fluids may flow above the surface features. Flow within the surface features may conform with the surface feature and be at an angle to the direction of the bulk flow in the microchannel. As the fluids exit the surface features they may exert momentum in the x and y direction for an x, y, z coordinate system wherein the bulk flow is in the z direction. This may result in a churning or rotation in the flow of the fluids. This pattern may be helpful for mixing a two-phase flow as the imparted velocity gradients may create fluid shear that breaks up one of the phases into small and well dispersed bubbles or droplets.

In one embodiment, two or more surface feature regions within the process microchannels (210, 310, 410, 940, 950, 960, 960A) may be placed in series such that mixing of the reactants and reaction to form a product may be accomplished using a first surface feature region, followed by at least one second surface feature region where a different flow pattern is used. The second flow pattern may be used to separate one or more unreacted reactants or the product from the reaction mixture. The second surface feature region may be used to assist gas or liquid recovery. This may be helpful for gas-liquid reactions, where a gas may be introduced into a liquid to form a reaction mixture which flows through the first surface feature region and undergoes reaction, followed by flow through the second surface feature region where the product and/or one or more unreacted reactants are separated from the reaction mixture. In the second surface feature region, a flow pattern may be used that creates a centrifugal force that drives liquid toward the interior walls of the process microchannels while the gas remains in the fluid core. One pattern of surface features that may create a strong central vortex in the fluid may comprise a pair of angled slots on the top and bottom of the process microchannel. This pattern of surface features may be used to create a central swirling flow pattern.

In one embodiment, the apertured section (350, 450, 470) may comprise an interior portion that forms part of one or more of the interior walls of each process microchannel. A surface feature sheet may overlie this interior portion of the apertured section. Surface features may be formed in and/or on the surface feature sheet. One of the reactant feed streams may flow through the apertured section and the surface feature sheet into the process microchannel. Part of this reactant feed stream may be detached from the surface of the surface feature sheet while part may flow within the surface features of the surface feature sheet. The surface feature sheet may contain angled surface features that have relatively small widths or spans relative to the overall flow length. The surface feature sheet may provide mechanical support for the apertured section. The surface features may impart a vertical flow pattern to this feed stream reactant. The vertical flow pattern may impart shear to the reactant feed stream flowing through the apertured section and thus reduce the size of reactant bubbles or droplets in the bulk flow path.

Examples of the surface features are illustrated in FIGS. 30-34. The surface features may have two or more layers stacked on top of each other or intertwined in a three-dimensional pattern. The pattern in each discrete layer may be the same or different. Flow may rotate or advect in each layer or only in one layer. Sub-layers, which may not be adjacent to the bulk flow path of the channel, may be used to create additional surface area. For example, these may be used to deposit a catalyst. The flow may rotate in the first level of surface features and diffuse molecularly into the second or more sublayers to promote reaction. Three-dimensional surface features may be made via metal casting or other processes where varying patterns may be broken into discrete planes as if stacked on top of one another. Three-dimensional surface features may be provided adjacent to the bulk flow path within the microchannel where the surface features have different depths, shapes, and/or locations accompanied by sub-features with patterns of varying depths, shapes and/or locations. The surface features may be advantageous for chemical reactions requiring additional surface area for catalyst deposition or for separation steps.

Figure 31:
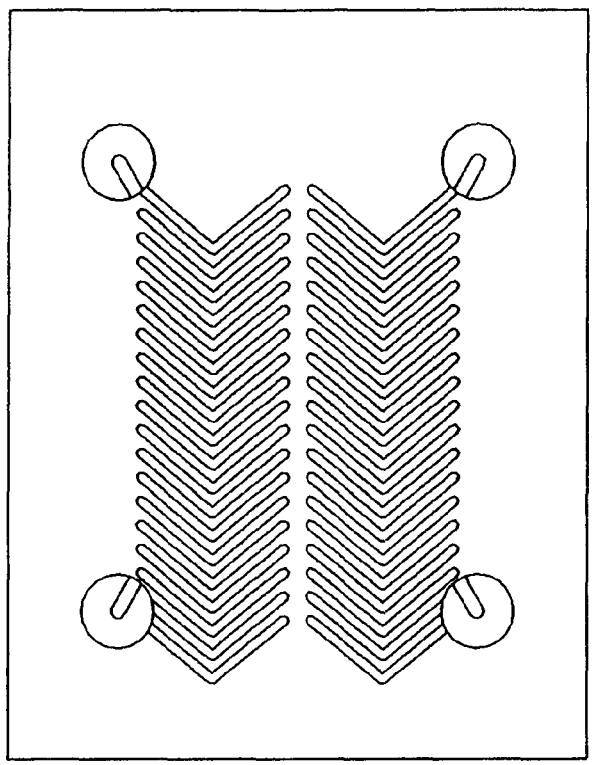
Figure 32:
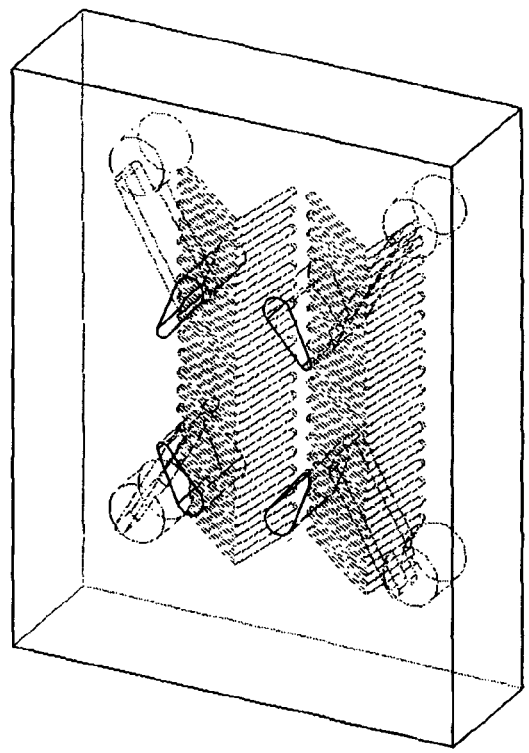

FIG. 31 is a schematic illustration of a top view of a three-dimensional surface feature structure. An example of a back view of a three-dimensional surface feature structure is illustrated in FIG. 32 where recessed chevrons are provided at the interface adjacent the bulk flow path of the microchannel. Beneath the chevrons are a series of three-dimensional structures that connect to the surface features adjacent to the bulk flow path but are made from structures of assorted shapes, depths, and/or locations. It may be further advantageous to provide sublayer passages that do not directly fall beneath an open surface feature that is adjacent to the bulk flow path within the microchannel but rather connect through one or more tortuous two-dimensional or three-dimensional passages. This approach may be advantageous for creating tailored residence time distributions in the microchannels, where it may be desirable to have a wider versus more narrow residence time distribution.

Figure 33:
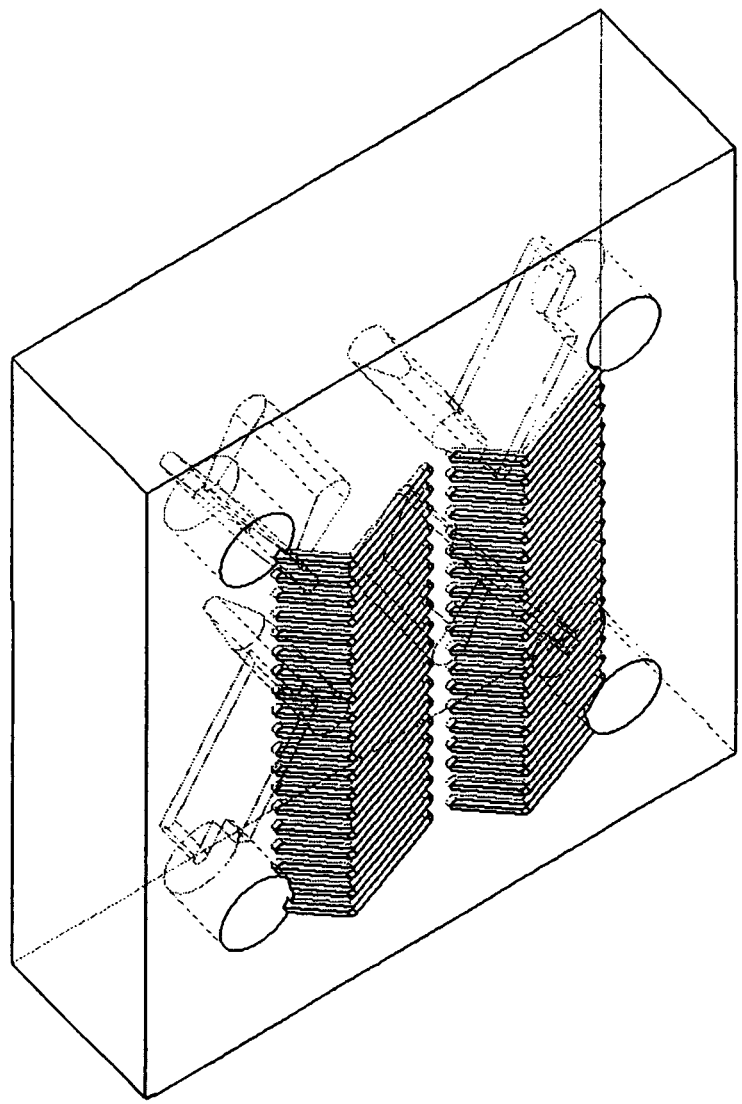

FIG. 33 is a front view of a three-dimensional surface feature where recessed chevrons abut the bulk flow path within the microchannel and have additional surface features of different shapes behind them at varying depths and locations.

The length and width of a surface feature may be defined in the same way as the length and width of a microchannel. The depth may be the distance which the surface feature sinks into or rises above the microchannel surface. The depth of the surface features may correspond to the direction of stacking a stacked and bonded microchannel device with surface features formed on or in the sheet surfaces. The dimensions for the surface features may refer the maximum dimension of a surface feature; for example the depth of a rounded groove may refer to the maximum depth, that is, the depth at the bottom of the groove.

The surface features may have depths that are less than about 2 mm, and in one embodiment less than about 1 mm, and in one embodiment in the range from about 0.01 to about 2 mm, and in one embodiment in the range from about 0.01 to about 1 mm, and in one embodiment in the range from about 0.01 mm to about 0.5 mm. The width of the surface features may be sufficient to nearly span the microchannel width (as shown in the herringbone designs), but in one embodiment (such as the fill features) can span about 60% or less of the width of the microchannel, and in one embodiment about 50% or less, and in one embodiment about 40% or less, and in one embodiment from about 0.1% to about 60% of the microchannel width, and in one embodiment from about 0.1% to about 50% of the microchannel width, and in one embodiment from about 0.1% to about 40% of the microchannel width. The width of the surface features may be in the range from about 0.05 mm to about 100 cm, and in one embodiment in the range from about 0.5 mm to about 5 cm, and in one embodiment in the range from about 1 to about 2 cm.

Multiple surface features or regions of surface features may be included within a microchannel, including surface features that recess at different depths into one or more microchannel walls. The spacing between recesses may be in the range from about 0.01 mm to about 10 mm, and in one embodiment in the range from about 0.1 to about 1 mm. The surface features may be present throughout the entire length of a microchannel or in portions or regions of the microchannel. The portion or region having surface features may be intermittent so as to promote a desired reaction or unit operation (for example, separation, cooling, etc.) in tailored zones. For example, a one-centimeter section of a microchannel may have a tightly spaced array of surface features, followed by four centimeters of a flat channel without surface features, followed by a two-centimeter section of loosely spaced surface features. The term "loosely spaced surface features" may be used to refer to surface features with a pitch or feature to feature distance that is more than about five times the width of the surface feature.

In one embodiment, the surface features may be in one or more surface feature regions that extend substantially over the entire axial length of a microchannel. In one embodiment, a microchannel may have surface features extending over about 50% or less of its axial length, and in one embodiment over about 20% or less of its axial length. In one embodiment, the surface features may extend over about 10% to about 100% of the axial length of the microchannel, and in one embodiment from about 20% to about 90%, and in one embodiment from about 30% to about 80%, and in one embodiment from about 40% to about 60% of the axial length of a microchannel.

FIGS. 27 and 31 show a number of different patterns that may be used for surface features. These patterns are not intended to limit the invention, only to illustrate a number of possibilities. As with any surface feature, the patterns may be used in different axial or lateral sections of a microchannel.

The heat sink may be used for cooling the fluids in the process microchannels. The heat sink may be used to preheat the reactants. The heat sink may be adjacent to the process microchannels (210, 310, 410, 940, 950, 960, 960A), the staged addition microchannels (340, 440), and/or the staged addition liquid catalyst microchannels (460). In one embodiment, the heat sink may not be in contact with or adjacent to the process microchannels, staged addition microchannels and/or staged addition liquid catalyst microchannels, but rather can be remote from the process microchannels, staged addition microchannels and/or staged addition liquid catalyst microchannels, but sufficiently close to receive heat from the same. The heat sink may comprise one or more heat exchange channels (220, 320, 420, 942, 952, 962) and/or one or more non-fluid cooling elements. The non-fluid cooling elements may be used to form one or more walls of the process microchannels (210, 310, 410, 940, 950, 960, 960A), staged addition microchannels (344, 440), and/or staged addition liquid catalyst microchannels (460). The non-fluid cooling element may be built into one or more walls of the process microchannels, staged addition microchannels and/or staged addition liquid catalyst microchannels. Cooling may be effected using Peltier-type thermoelectric cooling elements. Multiple cooling zones may be employed along the length of the process microchannels, staged addition microchannels and/or staged addition liquid catalyst microchannels. Similarly, multiple heat exchange fluids at different temperatures may be employed along the length of the process microchannels, staged addition microchannels and/or staged addition liquid catalyst microchannels. Cooling can be used to quench the product in the process microchannels after formation. The heat sink may be used to provide precise temperature controls within the process microchannels, staged addition microchannels and/or staged addition liquid catalyst microchannels. The cooling of the process microchannels during the inventive process, in one embodiment, is advantageous for reducing the formation of undesired by-products.

The heat exchange channels (220, 320, 420, 942, 952, 962) may have at least one internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The length or width may range from about 0.15 to about 10 mm, and in one embodiment from about 0.2 to about 10 mm, and in one embodiment from about 0.3 to about 10 mm. The height or width may range from about 0.2 to about 5 mm, and in one embodiment from about 0.2 to about 3 mm, and in one embodiment from about 0.3 to about 2 mm. The other internal dimension or height or width may range up to about 100 cm, and in one embodiment from about 0.01 to about 100 cm, and in one embodiment from about 0.1 cm to about 100 cm, and in one embodiment about 0.1 cm to about 50 cm, and in one embodiment about 0.2 cm to about 10 cm. The lengths of the heat exchange channels may be of any value, for example, the lengths may range up to about 10 m, and in one embodiment from about 1 cm to about 10 m, and in one embodiment from about 1 cm to about 5 m, and in one embodiment about 1 cm to about 2.5 m, and in one embodiment from about 1 cm to about 1 m, and in one embodiment from about 1 to about 50 cm, and in one embodiment from about 1 to about 25 cm. These heat exchange channels may be microchannels. The separation between the process microchannels (210, 310, 410, 940, 950, 960, 960A), staged addition microchannels (340, 440) and/or staged addition liquid catalyst microchannels (460), and the next adjacent heat exchange channels (220, 320, 420, 942, 952, 962) may be in the range from about 0.05 mm to about 5 mm, and in one embodiment about 0.2 mm to about 2 mm. The heat exchange channels may contain surface features as discussed above for modifying the flow or enhancing the mixing of heat exchange fluid within the heat exchange channels.

The heat exchange fluid may comprise any fluid. The heat exchange fluid may comprise air, steam, liquid water, gaseous nitrogen, liquid nitrogen, other gases including inert gases, carbon monoxide, carbon dioxide, oils such as mineral oil, gaseous hydrocarbons, liquid hydrocarbons, and heat exchange fluids such as Dowtherm A and Therminol which are available from Dow-Union Carbide.

The heat exchange fluid may comprise the first reactant feed stream and/or second reactant feed stream. This can provide process pre-heat and/or an increase in overall thermal efficiency of the process.

In one embodiment, an endothermic process may be conducted in the heat exchange channels. Examples of endothermic processes that may be conducted in the heat exchange channels include steam reforming and dehydrogenation reactions. In one embodiment, the incorporation of a simultaneous endothermic reaction to provide an improved heat sink may enable a typical heat flux of roughly an order of magnitude or more above the convective cooling heat flux.

In one embodiment, the heat exchange fluid may undergo a phase change as it flows through the heat exchange channels. This phase change may provide additional heat removal from the process microchannels beyond that provided by convective cooling. For example, a liquid heat exchange fluid may be vaporized and the additional heat being transferred from the process microchannels to the heat exchange channels would result from the latent heat of vaporization required by the heat exchange fluid. An example of such a phase change would be an oil or water that undergoes partial or complete boiling. In one embodiment, the percent boiling of the phase change fluid may be up to about 100% by weight, and in one embodiment up to about 75% by weight, and in one embodiment up to about 50% by weight.

The heat flux for convective heat exchange in the microchannel reactor may be in the range from about 0.01 to about 125 watts per square centimeter of surface area of the one or more process microchannels ($W/cm^2$) in the microchannel reactor, and in one embodiment about 0.1 to about 50 $W/cm^2$, and in one embodiment from about 1 to about 10 $W/cm^2$. The heat flux for phase change and/or an endothermic reaction of the heat exchange fluid may be in the range from about 0.01 to about 250 $W/cm^2$, and in one embodiment from about 1 to about 250 $W/cm^2$, and in one embodiment, from about 1 to about 100 $W/cm^2$, and in one embodiment from about 1 to about 50 $W/cm^2$, and in one embodiment from about 1 to about 25 $W/cm^2$, and in one embodiment from about 1 to about $W/cm^2$.

In one embodiment, the temperature of the feed streams entering the process microchannels may be within about 200° C., and in one embodiment within about 100° C., and in one embodiment within about 50° C., and in one embodiment within about 20° C., and in one embodiment within about 10° C., of the temperature of the product exiting the process microchannels.

The use of controlled heat exchange between heat exchange channels and/or non-fluid cooling elements in close proximity to or adjacent to the process microchannels may allow for uniform temperature profiles between the process microchannels. This provides for the possibility of a more uniform heat exchange at more rapid rates than can be obtained with conventional processing equipment such as mixing tanks. In a microchannel reactor employing multiple process microchannels, in one embodiment, the temperature difference between the process microchannels at at least one common position along the lengths of the process microchannels may be less than about 5° C., and in one embodiment less than about 2° C., and in one embodiment less than about 1° C.

The heat exchange channels and/or non-fluid cooling elements adjacent to or near either the process microchannels, staged addition microchannels or both, may employ separate temperature zones along the length of such channels. For example, in one embodiment, the temperature in a first zone near the entrance to the process microchannel may be maintained at a temperature above or below a second temperature in a second zone near the end of the process microchannel. A cool down or quench zone may be incorporated into the process microchannels to cool the product. Numerous combinations of thermal profiles may be possible, allowing for a tailored thermal profile along the length of the process microchannels and/or staged addition microchannels, including the possibility of heating or cooling zones before and/or after the reaction zone in the process microchannel to heat or cool the feed stream and/or product.

The heat exchange fluid entering the heat exchange channels may be at a temperature in the range from about 0° C. to about 500° C., and in one embodiment from about 100° C. to about 400° C. The heat exchange fluid exiting the heat exchange channels may be at a temperature in the range from about 0° C. to about 500° C., and in one embodiment about 100° C. to about 400° C. The residence time of the heat exchange fluid in the heat exchange channels may be in the range from about 5 ms to about 1 minute, and in one embodiment from about 20 ms to about 1 minute, and in one embodiment from about 50 ms to about 1 minute, and in one embodiment about 100 ms to about 1 minute. The pressure drop for the heat exchange fluid as it flows through the heat exchange channels may be in the range up to about 5 atm/m, and in one embodiment up to about 1 atm/m, and in one embodiment up to about 0.5 atm/m, and in one embodiment from about 0.01 to about 0.5 atm/m. The heat exchange fluid may be in the form of a vapor, a liquid, or a mixture of vapor and liquid. The Reynolds Number for the flow of vapor through the heat exchange channels may be in the range from about 10 to about 5000, and in one embodiment from about 100 to about 3000. The Reynolds Number for the flow of liquid through heat exchange channels may be in the range from about 10 to about 20000, and in one embodiment from about 100 to about 5000.

Figure 28:
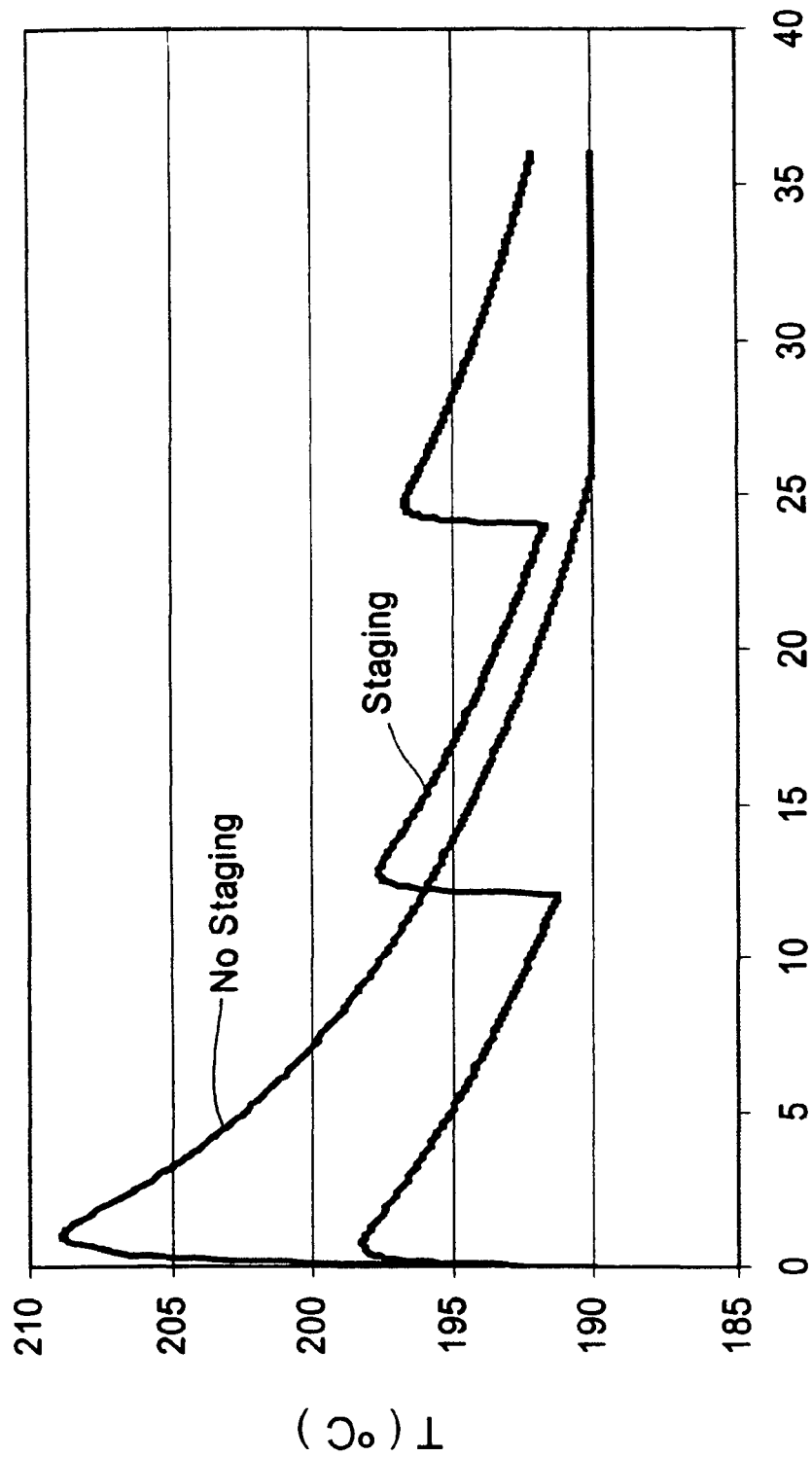
FIG. 28 is a plot of temperature vs. process microchannel length for an exothermic reaction wherein staged addition of one of the reactants is employed and is compared to a similar process wherein staged addition is not used.
Figure 29:
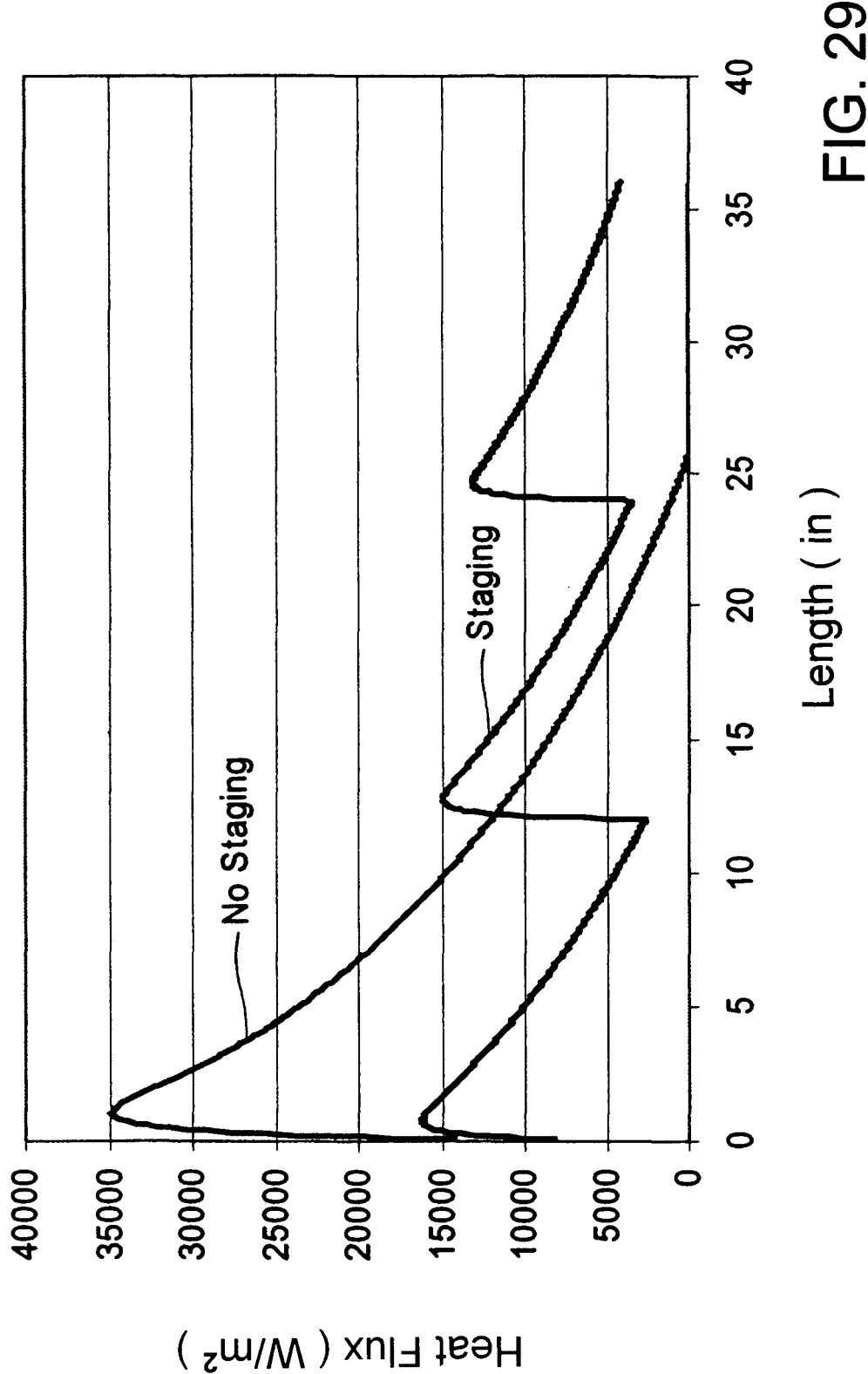
FIG. 29 is a plot of heat flux vs. process microchannel length for an exothermic reaction wherein staged addition of one of the reactants is employed and is compared to a similar process wherein staged addition is not used.
Figure 30:
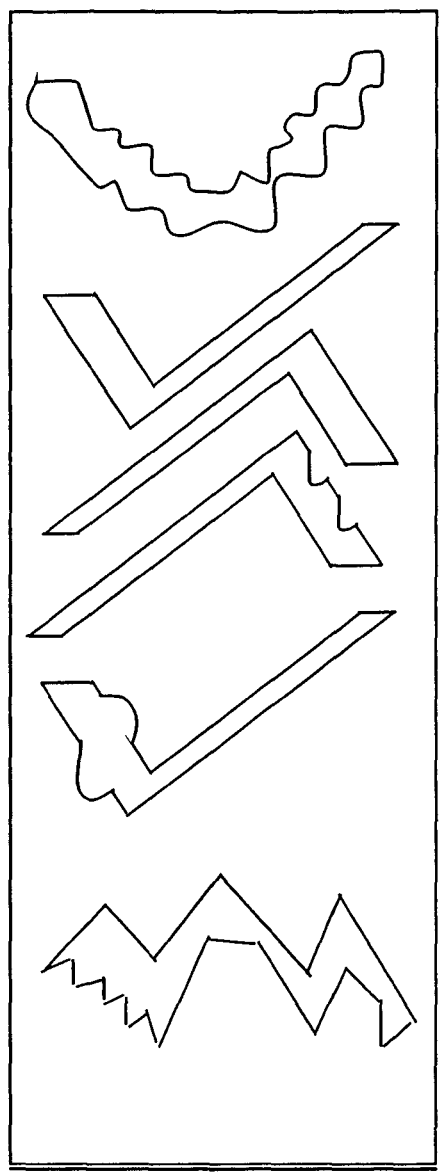
FIGS. 30-34 are schematic illustrations of surface features that may be provided in microchannels used with the inventive process.

In one embodiment, temperature rise in the microchannel reactor may be an important design and operation concern since the alkylation and acylation reactions are exothermic. The concern relates to avoiding reductions in product selectivity and/or shortened catalyst life. The staged addition of one of the reactant feed streams along at least part of the length of the process microchannels, which is employed with various embodiments of the inventive process (see, FIGS. 4-7, 9 and 10), provides the advantage of limiting or controlling temperature rise within the process microchannels. This also provides the advantage of lowering the local partial pressure of the staged addition reactant. This may lead to increased selectivity for lower order reactions. The use of staged addition to limit or control temperature rise within the process microchannels is illustrated in FIG. 28 where temperature profiles are plotted for an exothermic reaction. Referring to FIG. 28, for a process in which staged addition of one of the reactants is not used, the maximum temperature is observed at a location close to the inlet of the process microchannel corresponding to the maximum feed concentration; see, the curve marked "No Staging" in FIG. 28. The curve marked "Staging" is for the temperature profile of a process employing an equal bed size, overall feed rate and temperature but with three distinct feed locations within the process microchannel. The maximum temperature rise is reduced significantly. The staged addition feed design also gives rise to a more uniform or tailored heat flux profile along the length of the process microchannels; see, FIG. 29. This may significantly stabilize heat transfer in the inventive process.

The microchannel reactor 100 may be constructed of any material that provides sufficient strength, dimensional stability and heat transfer characteristics for carrying out the inventive process. Examples of suitable materials include steel (e.g., stainless steel, carbon steel, and the like), aluminum, titanium, nickel, and alloys of any of the foregoing metals, plastics (e.g., epoxy resins, UV cured resins, thermosetting resins, and the like), monel, inconel, ceramics, glass, composites, quartz, silicon, or a combination of two or more thereof. The microchannel reactor may be fabricated using known techniques including wire electrodischarge machining, conventional machining, laser cutting, photochemical machining, electrochemical machining, molding, water jet, stamping, etching (for example, chemical, photochemical or plasma etching) and combinations thereof. The microchannel reactor may be constructed by forming layers or sheets with portions removed that allow flow passage. A stack of sheets or strips attached to sheets may be assembled via diffusion bonding, laser welding, diffusion brazing, and similar methods to form an integrated device. Stacks of sheets may be gasketed together to form an integral device.

The microchannel reactor may be employed in conjunction with appropriate manifolds, valves, conduit lines, etc. to control flow of the reactants, product, and heatexchange fluid. These are not shown in the drawings, but can be readily provided by those skilled in the art. The microchannel reactor may be employed in conjunction with one or more downstream separation units, for example, one or more distillation, absorption, adsorption or membrane separation units. A higher conversion per pass, higher selectivity per pass, and/or a lower recycle ratio that may be achieved with the inventive process may eliminate the requirement for such downstream separation units or reduce the size or number of such downstream separation units.

The catalyst may comprise any alkylation and/or acylation catalyst. The catalyst may be in the form of a solid, a liquid, or a mixture thereof. The catalyst may be a protonic acid, such as sulfuric acid, hydrofluoric acid or phosphoric acid. The catalyst may be a Friedel-Crafts catalyst such as aluminum trichloride or boron fluoride. The catalyst may be a solid acid catalyst such as amorphous or crystalline alumino-silicate, clay, ion-exchange resin, mixed oxide, or supported acid. The solid acid catalysts may be a ZSM-5 or Y-type zeolite.

The catalyst may comprise a hydrogenating metal component and a solid acid constituent. Examples of suitable hydrogenating metal components include transition metals, such as metals of Group VIII of the Periodic Table. Among these, noble metals of Group VIII of the Periodic Table are useful. Platinum, palladium, and mixtures thereof are useful. Examples of solid acid constituents include zeolites such as zeolite beta, MCM-22, MCM-36, mordenite, X-zeolites and Y-zeolites, including H-Y-zeolites and USY-zeolites, non-zeolitic solid acids such as silica-alumina, sulphated oxides such as sulphated oxides of zirconium, titanium or tin, sulphated mixed oxides of zirconium, molybdenum, tungsten, etc., and chlorinated aluminum oxides. Mixtures of solid acid constituents can be employed.

The liquid catalyst may be in the form of droplets dispersed in the first reactant stream, the second reactant stream, or a mixture of the two streams. These mixtures may be in the form of emulsions. The droplets may have an average diameter in the range from about 0.001 to about 100 microns, and in one embodiment from about 0.01 to about 100 microns, and in one embodiment from about 0.05 to about 10 microns, and in one embodiment from about 0.1 to about 10 microns. The span for the distribution of droplets may range from about 0.001 to about 5, and in one embodiment from about 0.001 to about 2, and in one embodiment from about 0.001 to about 1, and in one embodiment from about 0.001 to about 0.1, and in one embodiment from about 0.001 to about 0.01.

The solid catalyst may have any size and geometric configuration that fits within the process microchannels. As indicated above, the catalyst may fill or partially fill the cross sections of the process microchannels and/or be coated on the interior walls of the process microchannels. The catalyst may be in the form of particulate solids (e.g., pellets, powder, fibers, and the like) having a median particle diameter of about 1 to about 1000 µm, and in one embodiment about 10 to about 500 µm, and in one embodiment about 25 to about 250 µm. In one embodiment, the catalyst may be in the form of a fixed bed of particulate solids such as illustrated in FIG. 22. Referring to FIG. 22, the catalyst 850 is contained within process microchannel 852. The reactants flow through the catalyst bed as indicated by arrows 854 and 856.

The catalyst may be supported on a porous support structure such as a foam, felt, wad or a combination thereof. The term "foam" is used herein to refer to a structure with continuous walls defining pores throughout the structure. The term "felt" is used herein to refer to a structure of fibers with interstitial spaces therebetween. The term "wad" is used herein to refer to a support having a structure of tangled strands, like steel wool. The catalyst may be supported on a support having a honeycomb structure or a serpentine configuration.

The catalyst may be supported on a flow-by support structure such as a felt with an adjacent gap, a foam with an adjacent gap, a fin structure with gaps, a washcoat on any inserted substrate, or a gauze that is parallel to the flow direction with a corresponding gap for flow. An example of a flow-by structure is illustrated in FIG. 23. In FIG. 23 the catalyst 860 is contained within process microchannel 862. An open passage way 864 permits the flow of the reactants through the process microchannel 862 in contact with the catalyst 860 as indicated by arrows 866 and 868.

The catalyst may be supported on a flow-through support structure such as a foam, wad, pellet, powder, or gauze. An example of a flow-through structure is illustrated in FIG. 24. In FIG. 24, the flow-through catalyst 870 is contained within process microchannel 872 and the reactants flow through the catalyst 870 as indicated by arrows 874 and 876.

The support may be formed from a material comprising silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof. In one embodiment, the support structure may be made of a heat conducting material, such as a metal, to enhance the transfer of heat away from the catalyst.

The catalyst may be directly washcoated on the interior walls of the process microchannels, grown on the walls from solution, or coated in situ on a fin structure. The catalyst may be in the form of a single piece of porous contiguous material, or many pieces in physical contact. In one embodiment, the catalyst may comprise a contiguous material and have a contiguous porosity such that molecules can diffuse through the catalyst. In this embodiment, the fluids may flow through the catalyst rather than around it. In one embodiment, the cross-sectional area of the catalyst may occupy from about 1 to about 99%, and in one embodiment from about 10 to about 95% of the cross-sectional area of the process microchannels. The catalyst may have a surface area, as measured by BET, of greater than about 0.5 $m^2/g$, and in one embodiment greater than about 2 $m^2/g$, and in one embodiment greater than about 5 $m^2/g$, and in one embodiment greater than about 10 $m^2/g$, and in one embodiment greater than about 25 $m^2/g$, and in one embodiment greater than about 50 $m^2/g$.

The catalyst may comprise a porous support, an interfacial layer overlying the porous support, and a catalyst material dispersed or deposited on the interfacial layer. The interfacial layer may be solution deposited on the support or it may be deposited by chemical vapor deposition or physical vapor deposition. In one embodiment the catalyst comprises a porous support, optionally a buffer layer overlying the support, an interfacial layer overlying the support or the optional buffer layer, and a catalyst material dispersed or deposited on the interfacial layer. Any of the foregoing layers may be continuous or discontinuous as in the form of spots or dots, or in the form of a layer with gaps or holes.

The porous support may have a porosity of at least about 5% as measured by mercury porosimetry and an average pore size (sum of pore diameters divided by number of pores) of about 1 to about 1000 μm. The porous support may be made of any of the above indicated materials identified as being useful in making a support structure. The porous support may comprise a porous ceramic support or a metal foam. Other porous supports that may be used include carbides, nitrides, and composite materials. The porous support may have a porosity of about 30% to about 99%, and in one embodiment about 60% to about 98%. The porous support may be in the form of a foam, felt, wad, or a combination thereof. The open cells of the metal foam may range from about 20 pores per inch (ppi) to about 3000 ppi, and in one embodiment about 20 to about 1000 ppi, and in one embodiment about 40 to about 120 ppi. The term "ppi" refers to the largest number of pores per inch (in isotropic materials the direction of the measurement is irrelevant; however, in anisotropic materials, the measurement is done in the direction that maximizes pore number).

The buffer layer, when present, may have a different composition and/or density than both the porous support and the interfacial layers, and in one embodiment has a coefficient of thermal expansion that is intermediate the thermal expansion coefficients of the porous support and the interfacial layer. The buffer layer may be a metal oxide or metal carbide. The buffer layer may be comprised of $Al_2O_3$, $TiO_2$, $SiO_2$, $ZrO_2$, or combination thereof. The $Al_2O_3$ may be $\alpha$-$Al_2O_3$, $\gamma$-$Al_2O_3$ or a combination thereof. $\alpha$-$Al_2O_3$ provides the advantage of excellent resistance to oxygen diffusion. The buffer layer may be formed of two or more compositionally different sublayers. For example, when the porous support is metal, for example a stainless steel foam, a buffer layer formed of two compositionally different sub-layers may be used. The first sublayer (in contact with the porous support) may be $TiO_2$. The second sublayer may be $\alpha$-$Al_2O_3$ which is placed upon the $TiO_2$. In one embodiment, the $\alpha$-$Al_2O_3$ sublayer is a dense layer that provides protection of the underlying metal surface. A less dense, high surface area interfacial layer such as alumina may then be deposited as support for a catalytically active layer.

The porous support may have a thermal coefficient of expansion different from that of the interfacial layer. In such a case a buffer layer may be needed to transition between the two coefficients of thermal expansion. The thermal expansion coefficient of the buffer layer can be tailored by controlling its composition to obtain an expansion coefficient that is compatible with the expansion coefficients of the porous support and interfacial layers. The buffer layer should be free of openings and pin holes to provide superior protection of the underlying support. The buffer layer may be nonporous. The buffer layer may have a thickness that is less than one half of the average pore size of the porous support. The buffer layer may have a thickness of about 0.05 to about 10 μm, and in one embodiment about 0.05 to about 5 μm.

In one embodiment of the invention, adequate adhesion and chemical stability may be obtained without a buffer layer. In this embodiment the buffer layer may be omitted.

The interfacial layer may comprise nitrides, carbides, sulfides, halides, metal oxides, carbon, or a combination thereof. The interfacial layer provides high surface area and/or provides a desirable catalyst-support interaction for supported catalysts. The interfacial layer may be comprised of any material that is conventionally used as a catalyst support. The interfacial layer may be comprised of a metal oxide. Examples of metal oxides that may be used include $\gamma$-$Al_2O_3$, $SiO_2$, $ZrO_2$, $TiO_2$, tungsten oxide, magnesium oxide, vanadium oxide, chromium oxide, manganese oxide, iron oxide, nickel oxide, cobalt oxide, copper oxide, zinc oxide, molybdenum oxide, tin oxide, calcium oxide, aluminum oxide, lanthanum series oxide(s), zeolite(s) and combinations thereof. The interfacial layer may serve as a catalytically active layer without any further catalytically active material deposited thereon. Usually, however, the interfacial layer is used in combination with a catalytically active layer. The interfacial layer may also be formed of two or more compositionally different sublayers. The interfacial layer may have a thickness that is less than one half of the average pore size of the porous support. The interfacial layer thickness may range from about 0.5 to about 100 μm, and in one embodiment from about 1 to about 50 μm. The interfacial layer may be either crystalline or amorphous. The interfacial layer may have a BET surface area of at least about 1 $m^2/g$.

The catalyst may be deposited on the interfacial layer. Alternatively, the catalyst material may be simultaneously deposited with the interfacial layer. The catalyst layer may be intimately dispersed on the interfacial layer. That the catalyst layer is "dispersed on" or "deposited on" the interfacial layer includes the conventional understanding that microscopic catalyst particles are dispersed: on the support layer (i.e., interfacial layer) surface, in crevices in the support layer, and in open pores in the support layer.

The catalyst may be supported on an assembly of one or more fins positioned within the process microchannels. Examples are illustrated in FIGS. 25-27. Referring to FIG. 25, fin assembly 880 includes fins 882 which are mounted on fin support 884 which overlies base wall 886 of process microchannel 888. The fins 882 project from the fin support 884 into the interior of the process microchannel 888. The fins 882 extend to the interior surface of upper wall 890 of process microchannel 888. Fin channels 892 between the fins 882 provide passage ways for fluid to flow through the process microchannel 888 parallel to its length. Each of the fins 882 has an exterior surface on each of its sides, this exterior surface provides a support base for the catalyst. With the inventive process, the reactants flow through the fin channels 892, contact the catalyst supported on the exterior surface of the fins 882, and react to form the product. The fin assembly 880a illustrated in FIG. 26 is similar to the fin assembly 880 illustrated in FIG. 25 except that the fins 882a do not extend all the way to the interior surface of the upper wall 890 of the microchannel 888. The fin assembly 880b illustrated in FIG. 27 is similar to the fin assembly 880 illustrated in FIG. 25 except that the fins 882b in the fin assembly 880b have cross sectional shapes in the form of trapezoids. Each of the fins (882, 882a, 882b) may have a height ranging from about 0.02 mm up to the height of the process microchannel 888, and in one embodiment from about 0.02 to about 10 mm, and in one embodiment from about 0.02 to about 5 mm, and in one embodiment from about 0.02 to about 2 mm. The width of each fin (882, 882a, 882b) may range from about 0.02 to about 5 mm, and in one embodiment from about 0.02 to about 2 mm and in one embodiment about 0.02 to about 1 mm. The length of each fin (882, 882a, 882b) may be of any length up to the length of the process microchannel 888, and in one embodiment up to about 10 m, and in one embodiment about 0.5 to about 10 m, and in one embodiment about 0.5 to about 6 m, and in one embodiment about 0.5 to about 3 m. The gap between each of the fins (882, 882a, 882b) may be of any value and may range from about 0.02 to about 5 mm, and in one embodiment from about 0.02 to about 2 mm, and in one embodiment from about 0.02 to about 1 mm. The number of fins (882, 882a, 882b) in the process microchannel 888 may range from about 1 to about 50 fins per centimeter of width of the process microchannel 888, and in one embodiment from about 1 to about 30 fins per centimeter, and in one embodiment from about 1 to about 10 fins per centimeter, and in one embodiment from about 1 to about 5 fins per centimeter, and in one embodiment from about 1 to about 3 fins per centimeter. As indicated above, each of the fins may have a cross-section in the form of a rectangle or square as illustrated in FIG. 25 or 26, or a trapezoid as illustrated in FIG. 27. When viewed along its length, each fin (882, 882a, 882b) may be straight, tapered or have a serpentine configuration. The fin assembly (880, 880a, 880b) may be made of any material that provides sufficient strength, dimensional stability and heat transfer characteristics to permit operation for which the process microchannel is intended. These materials include: steel (e.g., stainless steel, carbon steel, and the like); monel; inconel; aluminum; titanium; nickel; platinum; rhodium; copper; chromium; brass; alloys of any of the foregoing metals; polymers (e.g., thermoset resins); ceramics; glass; composites comprising one or more polymers (e.g., thermoset resins) and fiberglass; quartz; silicon; or a combination of two or more thereof. The fin assembly (880, 880a, 880b) may be made of an $Al_2O_3$ forming material such as an alloy comprising Fe, Cr, Al and Y, or a $Cr_2O_3$ forming material such as an alloy of Ni, Cr and Fe.

In one embodiment, the reaction zone (212, 312) in the process microchannel (210, 310) may be characterized by having a bulk flow path. The term "bulk flow path" refers to an open path (contiguous bulk flow region) within the process microchannels. A contiguous bulk flow region allows rapid fluid flow through the microchannels without large pressure drops. In one embodiment, the flow of fluid in the bulk flow region is laminar. Bulk flow regions within each process microchannel (210, 310) may have a cross-sectional area of about 0.05 to about 10,000 $mm^2$, and in one embodiment about 0.05 to about 5000 $mm^2$, and in one embodiment about 0.1 to about 2500 $mm^2$. The bulk flow regions may comprise from about 5% to about 95%, and in one embodiment about 30% to about 80% of the cross-section of the process microchannels.

In one embodiment, relatively short contact times, relatively high selectivity to the desired alkylation and/or acylation product, and/or relatively low rates of deactivation of the catalyst may be achieved by limiting the diffusion length or distance required for the catalyst. While not wishing to be bound by theory, it is believed that this may be analogous to the pore length in a Thiele modulus analysis. The Thiele modulus is defined as the pore length multiplied by the square root of a term defined as the reaction rate constant multiplied by the reactant mixture density divided by the effective diffusivity within the pore. The Thiele modulus may be related to the reaction effectiveness factor, where increasing values of the Thiele modulus gives lower effectiveness factors or, conversely, a lower effective use of the catalyst activity. This may be achieved during the alkylation of benzene with ethylene in the presence of a ZSM-5 zeolite catalyst when the catalyst is in the form of a thin layer on an engineered support such as a metallic foam or on the wall of the process microchannel. This allows for increased space velocities and operation at higher benzene to ethylene ratios. In one embodiment, the thin layer of catalyst can be produced using chemical vapor deposition. This thin layer may have a thickness in the range up to about 50 microns, and in one embodiment from about 0.1 to about 20 microns, and in one embodiment from about 0.1 to about 10 microns, and in one embodiment from about 0.1 to about 5 microns, and in one embodiment from abut 0.1 to about 1 micron, and in one embodiment about 0.25 micron. These dimensions may be smaller than the diameters of many ZSM-5 zeolite crystals. The effect of these thin layers is to reduce the time the reactants are within the active catalyst structure by reducing the diffusional distance. This decreases the time the reactants spend in the active portion of the catalyst. The result may be increased selectivity to the desired alkylation and/or acylation product and reduced production of coke. An advantage of this mode of catalyst deployment is that, unlike conventional catalysts in which the active portion of the catalyst is bound up in an inert low thermal conductivity binder, the active catalyst film may be in intimate contact with either the engineered support or the wall of the process microchannel. This may be used to leverage high heat transfer rates attainable in the microchannel reactor and allows for close control of temperature. The result is the ability to operate at increased temperature (faster kinetics) without promoting coking, thus producing higher productivity and yield and prolonging catalyst life.

EXAMPLE

A process microchannel having a height of 2 mm, a width of 25.4 mm and a length of 30.5 cm has a layer of ZSM-5 zeolite catalyst having a thickness of 0.25 micron coated on its interior wall. A premixed feed of benzene and ethylene containing two moles of benzene for every mole of ethylene flows through the process microchannel. The temperature of the feed mixture at the inlet is 500° C. The process microchannel is operated at a space velocity in excess of about 10,000 $hr^{-1}$ with an overall yield of ethylbenzene that may be estimated to be about 99%.

In one embodiment, the catalyst may be regenerated. This may be done by flowing a regenerating fluid through the process microchannels (210, 310, 410) in contact with the catalyst. The regenerating fluid may comprise hydrogen or a diluted hydrogen stream. The diluent may comprise nitrogen, argon, steam, methane, carbon dioxide, or a mixture of two or more thereof. The concentration of $H_2$ in the regenerating fluid may range up to about 100% by volume, and in one embodiment from about 1 to about 100% by volume, and in one embodiment about 1 to about 50% volume. The regenerating fluid may comprise oxygen or an oxygen containing fluid. The concentration of $O_2$ in the regenerating fluid may range up to about 95% by volume, and in one embodiment from about 1 to about 50% by volume. The regenerating fluid may flow from the header 104 through the process microchannels to the footer 106, or in the opposite direction from the footer 106 through the process microchannels to the header 104. The temperature of the regenerating fluid may be from about 20 to about 600° C., and in one embodiment about 20 to about 400° C., and in one embodiment about 80 to about 200° C. The pressure within the process microchannels (210, 310, 410, 940, 950, 960, 960A) during this regeneration step may range from about 1 to about 100 atmospheres, and in one embodiment about 1 to about 10 atmospheres. The residence time for the regenerating fluid in the process microchannels may range from about 0.001 to about 10 seconds, and in one embodiment about 0.01 second to about 1 second.

The contact time of the reactants with the catalyst within the process microchannels (210, 310, 410, 940, 950, 960, 960A) may be in the range up to about 10 minutes, and in one embodiment in the range from about 1 millisecond (ms) to about 10 minutes, and in one embodiment in the range from about 1 ms to about 5 minutes, and in one embodiment in the range from about 1 ms to about 2 minutes, and in one embodiment in the range from about 1 ms to about 1 minute, and in one embodiment from about 1 ms to about 500 ms, and in one embodiment about 1 ms to about 200 ms, and in one embodiment about 1 ms to about 100 ms, and in one embodiment about 1 ms to about 50 ms, and in one embodiment about 1 ms to about 20 ms, and in one embodiment about 1 ms to about 10 ms.

The weight hourly space velocity (WHSV) for the flow of the reactants and product through the microchannel reactor core 102 may be at least about 100 (ml feed)/(g catalyst)(hour). The WHSV may be in the range from about 100 to about 1,000,000, and in one embodiment from about 10,000 to about 1,000,000, and in one embodiment from about 10,000 to about 100,000 (ml feed)/(g catalyst)(hr).

The temperature of the reactants entering the microchannel reactor core 102 may be in the range from about 20° C. to about 500° C., and in one embodiment about 100° C. to about 400° C., and in one embodiment about 150° C. to about 250° C.

The temperature within the process microchannels in the microchannel reactor core 102 may be in the range from about 20° C. to about 500° C., and in one embodiment from about 100° C. to about 400° C., and in one embodiment from about 150° C. to about 250° C.

The temperature of the product exiting the microchannel reactor core 102 may be in the range from about 20° C. to about 500° C., and in one embodiment about 100° C. to about 400° C., and in one embodiment about 150° C. to about 250° C.

The pressure within the process microchannels in the microchannel reactor core 102 may be in the range up to about 100 atmospheres absolute pressure, and in one embodiment up to about 75 atmospheres, and in one embodiment up to about 50 atmospheres absolute pressure. In one embodiment, the pressure may be in the range from about 1 to about 50 atmospheres absolute pressure, and in one embodiment from about 10 to about 40 atmospheres, and in one embodiment from about 20 to about 30 atmospheres absolute pressure.

The pressure drop of the reactants and/or products as they flow through the process microchannels may be in the range up to about 5 atmospheres per meter of length of the process microchannel (atm/m), and in one embodiment up to about 1 atm/m, and in one embodiment up to about 0.1 atm/m.

The pressure drop for the second reactant feed stream flowing through the apertured sections (350, 450) may be in the range up to about 5 atm, and in one embodiment from about 0.001 to about 5 atm, and in one embodiment from about 0.001 to about 0.2 atm, and in one embodiment about 0.001 to about 0.05 atm.

The reactants and products flowing through the process microchannels may be in the form of a vapor, a liquid, or a mixture of vapor and liquid. The Reynolds Number for the flow of vapor through the process microchannels may be in the range from about 10 to about 10000, and in one embodiment about 100 to about 3000. The Reynolds Number for the flow of liquid through the process microchannels may be about 10 to about 10000, and in one embodiment about 100 to about 3000.

While not wishing to be bound by theory, it is believed that a high superficial velocity may be advantageous for reactions wherein both gas and liquid phases are present during the reaction. This is because the shear force of the fluid may act to thin the liquid layer that may form on the surface of the catalyst. Thinner liquid films may reduce the mass transfer resistance of the reactants to the catalyst surface and improve conversion at relatively short contact times for the reactants, for example, contact times less than about 500 milliseconds. In one embodiment, the superficial velocity for the fluids flowing through the process microchannels may be at least about 0.01 meters per second (m/s), and in one embodiment in the range from about 0.01 to about 5 m/s, and in one embodiment in the range from about 0.01 to about 2 m/s, and in one embodiment in the range from about 0.01 to about 1 m/s, and in one embodiment in the range from about 0.05 to about 0.5 m/s.

Figure 11:
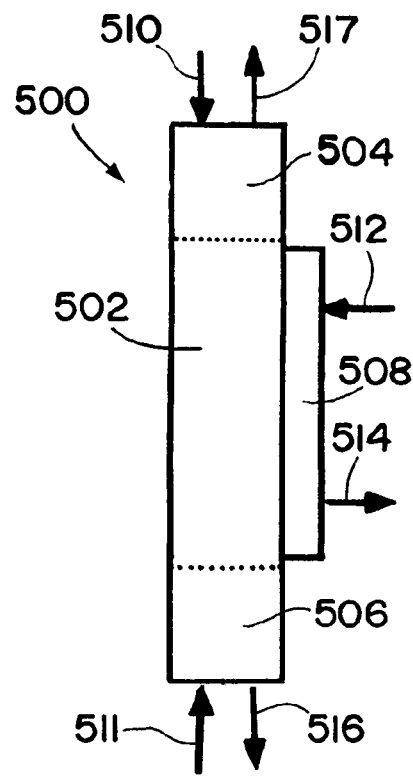
FIG. 11 is a schematic drawing illustrating the inventive process in a particular form wherein reactive distillation is used in a process to react with a first reactant feed stream and a second reactant feed stream to form an alkylation and/or acylation product.
Figure 12:
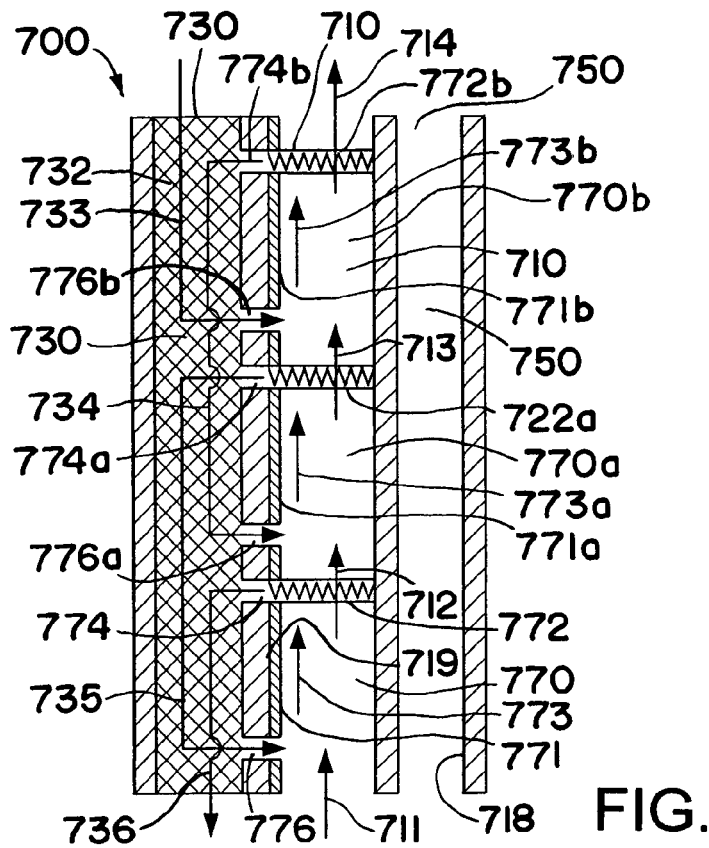
FIG. 12 is a schematic illustration of a repeating unit comprising a process microchannel containing multiple reactive distillation stages, a liquid channel containing a wicking region, and a heat exchange channel, that may be used in the microchannel reactor core of the microchannel reactor illustrated in FIG. 11.
Figure 13:
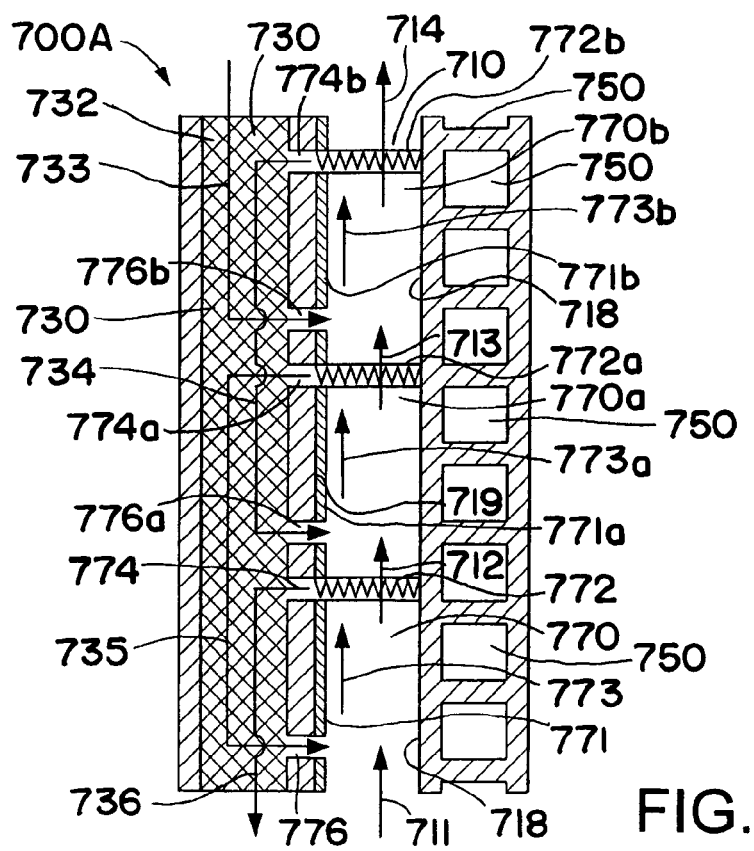
FIG. 13 is a schematic illustration of an alternate embodiment of a repeating unit comprising a process microchannel containing multiple reactive distillation stages, a liquid channel containing a wicking region, and a heat exchange channel, that may be used in the microchannel reactor core of the microchannel reactor illustrated in FIG. 11.

In one embodiment, the inventive process may employ the use of reactive distillation to form the desired alkylation and/or acylation products. This is illustrated in FIGS. 11-13. Referring to FIG. 11, the process may be operated using microchannel reactor 500, which may be referred to as a reactive distillation microchannel reactor. Microchannel reactor 500 comprises microchannel reactor core 502, feed stream header 504, feed stream header and product footer 506, and heat exchange manifold 508. The reactor core 502 contains one or more process microchannels. Each of the process microchannels contains one or more reaction zones. In one embodiment, a first reactant feed stream comprising a reactant substrate flows into the microchannel reactor 500 through the feed stream header 504, as indicated by arrow 510. A second reactant feed stream comprising an alkylating agent, an acylating agent, or a mixture thereof, flows into the microchannel reactor 500 through feed stream header and product footer 506, as indicated by arrow 511. Alternatively, the first reactant feed stream may enter the microchannel reactor 500 through the feed stream header and product footer 506, as indicated by arrow 511, and the second reactant feed stream may enter the microchannel reactor 500 through the feed stream header 504, as indicated by arrow 510. The reactant feed stream 510 entering the microchannel reactor 500 through the feed stream header 504 may be in the form of a liquid, while the reactant feed stream 511 entering the microchannel reactor 500 through feed stream header and product footer 506 may be in the form of a vapor.

The first reactant feed stream and the second reactant feed stream flow into the one or more process microchannels in the reactor core 502. In the process microchannels the reactant feed streams flow into the reaction zones wherein they contact each other and a catalyst and react to form the desired alkylation product and/or acylation product. The catalyst may be in the form of a liquid, a solid, or a combination thereof. The liquid catalyst may be mixed with either the first and/or second reactant feed streams. The liquid catalyst may be introduced into the reaction zones separately. The liquid catalyst may be in the form of dispersed droplets as discussed above. The solid catalyst may have any size and configuration that fits within the reaction zones, these sizes and configurations being the same as those discussed above. The alkylation product and/or acylation product flows from the reactor core 502 through the feed stream header and product footer 506, and from the feed stream header and product footer 506 out of the reactor, as indicated by arrow 516. The product may be in the form of a liquid. The reactant feed stream 511 may be reacted with the reactant feed stream 510 to form the product. Any unreacted components of the reactant feed stream 511 may be mixed with the product stream 516. Any unreacted components of the feed stream 511 that do not form a mixture with the product stream 516 may exit the microchannel reactor 500 through header 504, as indicated by arrow 517. Although an advantage of the inventive process is that a high level of conversion to the desired alkylation product and/or acylation product can be obtained with one pass through the microchannel reactor, in one embodiment, one or more reactants can be separated from the alkylation product and/or acylation product using conventional techniques and recycled back through the microchannel reactor 500. The unreacted reactants can be recycled through the microchannel reactor any number of times, for example, one, two, three, four times, etc.

During the inventive process heat may be transferred from the process microchannels in the microchannel reactor 500 to a heat sink. The heat sink may comprise one or more heat exchange channels and/or non-fluid cooling elements. These may be adjacent to or remote from the process microchannels. In one embodiment, a heat exchange fluid flows into heat exchange manifold 508, as indicated by arrow 512, and from heat exchange manifold 508 through heat exchange channels in the reactor core 502, and then back to the heat exchange manifold 508 and out of the heat exchange manifold 508, as indicated by arrow 514. The heat exchange manifold 508 may comprise one or more heat exchange headers and one or more heat exchange footers to separate the heat exchange inlet stream 512 from the heat exchange outlet stream 514. Heat exchange between the reactant feed streams and product, and the heat exchange fluid may be effected using convective heat transfer. In one embodiment, heat exchange may be enhanced by the heat exchange fluid undergoing an endothermic reaction and/or a full or partial phase change in the heat exchange channels in the reactor core 502. In one embodiment, non-fluid cooling elements can be used in place of or to supplement the heat exchange provided by the heat exchange fluid. In one embodiment, multiple heat exchange manifolds 508 may be provided over the length of the reactor core 502 to provide multiple heat exchange zones having different heat fluxes and/or temperatures. These may be the same as described above.

The microchannel reactor 500 may be employed in conjunction with storage vessels, pumps, valves, microprocessors, flow control devices, and the like, which are not shown in the drawings, but would be apparent to those skilled in the art. The microchannel reactor may be employed in conjunction with one or more downstream separation units, for example, one or more distillation, absorption, adsorption or membrane separation units. A higher conversion per pass, higher selectivity per pass, and/or a lower recycle ratio that may be achieved with the inventive process may eliminate the requirement for such downstream separation units or reduce the size or number of such downstream separation units. The microchannel reactor 500 may be constructed using the same materials and techniques as the microchannel reactor 100 discussed above.

Figure 11A:
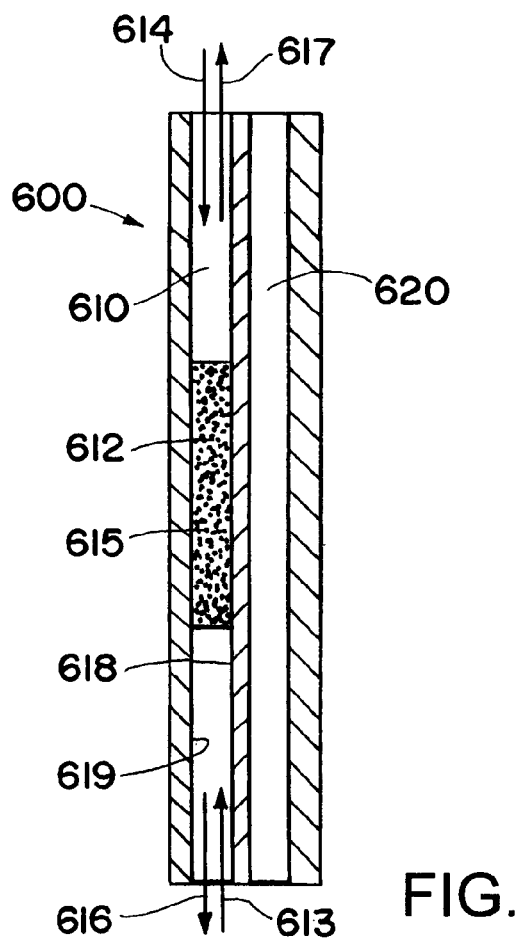
FIG. 11A is a schematic illustration of a repeating unit comprising a process microchannel and a heat exchange channel that may be used in the microchannel reactor core of the microchannel reactor illustrated in FIG. 11.

FIG. 11A illustrates repeating unit 600 which may be used in the reactor core 502 of the microchannel reactor 500. Repeating unit 600 comprises process microchannel 610 and heat exchange channel 620. Process microchannel 610 includes a reaction zone 612 wherein catalyst 615 is present. The first reactant feed stream flows through the feed stream header 504 into process microchannel 610, as indicated by arrow 614. The second reactant feed stream flows through the feed stream header and product footer 506 into process microchannel 610, as indicated by arrow 613. Alternatively, the second reactant feed stream could enter the process microchannel 610 in the direction indicated by arrow 614, and the first reactant feed stream could enter the process microchannel 610 in the direction indicated by arrow 613. The feed stream entering the process microchannel 610 in the direction indicated by arrow 614 may be a liquid, while the feed stream entering the process microchannel in the direction indicated by arrow 613 may be a vapor. The first reactant feed stream and the second reactant feed stream flow into the reaction zone 612 wherein they contact each other and the catalyst 615, and react to form the desired alkylation and/or acylation product. The product may be in the form of a liquid. The product exits the process microchannel 610, as indicated by arrow 616. The reactant feed stream 613 may be reacted with reactant feed stream 614 to form the product. Any unreacted components of the feed stream 613 may be mixed with the product stream 616. Any unreacted components of the feed stream 613 that do not form a mixture with the product stream 616 may exit the process microchannel 610, as indicated by arrow 617. The product stream 616 exiting the process microchannel 610 flows through the feed stream header and product footer 506, and out of the reactor 500, as indicated by arrow 516. Any unreacted components of the feed stream 613 that do not form a mixture with the product may exit the microchannel reactor 500 through the header 504, as indicated by arrow 517. Heat exchange fluid flows from heat exchange manifold 508 through heat exchange channel 620 and then back to heat exchange manifold 508. The flow of the heat exchange fluid through the heat exchange channel 620 may be co-current or counter-current to the flow of fluid flowing through the process microchannel 610 in the direction indicated by arrow 614. Alternatively, the heat exchange channel 620 could be oriented to provide for the flow of the heat exchange fluid in a direction that would be cross-current to the flow of fluid through the process microchannel 610. The process microchannel 610 and heat exchange channel 620 may contain surface features as discussed above, for modifying the flow of fluid and/or enhancing mixing within the channels. The repeating unit 600 illustrated in FIG. 11A may occur once with in the microchannel reactor core 502 or it may be repeated any number of times, for example, two, three, four, five, ten, twenty, fifty, one hundred, hundreds, one thousand, thousands, ten thousand, tens of thousands, one hundred thousand, hundreds of thousands, millions of times, etc.

FIG. 12 illustrates repeating unit 700 which may be used in the reactor core 502 of the microchannel reactor 500 illustrated in FIG. 11. Repeating unit 700 comprises process microchannel 710, liquid channel 730, and heat exchange channel 750. Liquid channel 730 is adjacent to process microchannel 710. Heat exchange channel 750 is adjacent to process microchannel 710. The illustrated embodiment depicted in FIG. 12 contains three microchannel reactive distillation stages, namely, microchannel reactive distillation stages 770, 770a, and 770b, housed within process microchannel 710. It will be understood, however, that the process microchannel 710 may house any desired number of microchannel reactive distillation stages, for example, four, five, six, seven, eight, ten, tens, hundreds, thousands, etc. Each of the microchannel reactive distillation stages comprises an interior catalyst-containing wall (771, 771a, 771b), a capture structure (772, 772a, 772b), a liquid exit (774, 774a, 774b), and a liquid entrance (776, 776a, 776b). Each microchannel reactive distillation stage may contain surface features, as discussed above, for modifying flow and/or enhancing mixing within each microchannel distillation stage. The capture structures (772, 772a, 772b) and the liquid exits (774, 774a, 774b) are adjacent to each other and are suitable for permitting the flow of liquid from the process microchannel 710 to the liquid channel 730. The liquid entrances (776, 776a, 776b) are positioned upstream from the liquid exits (774, 774a, 774b) and are suitable for permitting liquid to flow from the liquid channel 730 into the process microchannel 710. The liquid channel 730 contains wicking region 732. The wicking region 732 comprises porous flow passages which allow liquid to flow through the wicking region from the liquid exit (for example, liquid exit 774b) of each microchannel reactive distillation stage to the liquid entrance (for example, liquid entrance 776a) of the next adjacent upstream microchannel reactive distillation stage.

In operation, a liquid phase, which may comprise the first reactant feed stream, flows downwardly through a porous flow passage in the wicking region 732 in the liquid channel 730 to liquid entrance 776b, as indicated by arrow 733. The liquid phase enters microchannel distillation stage 770b and flows along catalyst-containing wall 771b as a thin film, as indicated by arrow 773b, until it contacts capture structure 772b. A vapor phase, which may comprise the second reactant feed stream, flows through capture structure 772a into microchannel distillation stage 770b, as indicated by arrow 713, and flows upwardly through microchannel distillation stage 770b until it contacts capture structure 772b. Alternatively, the first reactant feed stream could be used as the vapor phase, and the second reactant feed stream could be used as the liquid phase. The flow of the liquid phase along the catalyst-containing wall 771b is driven by drag from the flow of the vapor phase through the microchannel distillation stage 770b. In the microchannel distillation stage 770b the liquid phase and the vapor phase contact each other. Part of the vapor phase transfers to the liquid phase and reacts with the liquid phase to form the desired alkylation product and or acylation product. The liquid phase becomes a product rich liquid phase. The remainder of the vapor phase flows through capture structure 772b as indicated by arrow 714. The product rich liquid phase may flow from capture structure 772b through liquid exit 774b as a result of capillary force and then downwardly as a result of gravitational force through a porous flow passage in the wicking region 732, as indicated by arrow 734, and then through liquid entrance 776a as a result of capillary effect and gravity. The liquid phase flowing through liquid entrance 776a enters microchannel distillation stage 770a and flows along catalyst-containing wall 771a as a thin film, as indicated by arrow 773a, until it contacts capture structure 772a. The vapor phase flows through capture structure 772 into microchannel distillation stage 770, as indicated by arrow 712, and flows through microchannel distillation stage 770a until it contacts capture structure 772a. The vapor phase flow may be driven by a pressure differential. Within microchannel stage 770a, the liquid phase and the vapor phase contact each other. Part of the vapor phase transfers to the liquid phase and reacts with the liquid phase to form the desired alkylation product and/or acylation product. The concentration of product in the liquid phase increases. The remainder of the vapor phase flows through capture structure 772a into microchannel distillation stage 770b, as indicated by arrow 713. The resulting product rich liquid phase flows from capture structure 772a through liquid exit 774a downwardly through a porous flow passage in the wicking region 732 in liquid channel 730, as indicated by arrow 735, into liquid entrance 776. The liquid phase flows through liquid entrance 776 into microchannel distillation stage 770 and along catalyst-containing wall 771 as a thin film, as indicated by arrow 773, until it contacts capture structure 772. The vapor phase flows into microchannel distillation stage 770, as indicated by arrow 711, and flows upwardly through microchannel distillation stage 770 until it contacts capture structure 772. Within the microchannel distillation stage 770 the liquid phase and the vapor phase contact each other. Part of the vapor phase transfers to the liquid phase and reacts with the liquid phase to form the desired alkylation product and/or acylation product. The concentration of product in the liquid phase increases. The resulting product rich liquid phase flows from capture structure 772 through liquid exit 774 into the wicking region 732 within liquid channel 730 and downwardly through a porous flow passage in the wicking region 732, as indicated by arrow 736. The liquid phase flowing along line 736 has a higher concentration of product and a lower concentration of reactant than the liquid phase flowing downwardly through liquid channel 730 into liquid entrance 776b, as indicated by arrow 733. The vapor phase flowing through capture structure 772b, as indicated by arrow 714, has a lower concentration of the reactant than the vapor phase entering microchannel distillation stage 770, as indicated by arrow 711.

Heat exchange fluid may flow through heat exchange channel 750 in a direction that can be co-current or counter-current relative to the flow of the vapor phase through the process microchannel 710. Multiple heat exchange zones can be employed along the length of the process microchannel 710 to provide for different temperatures at different locations along the length of the process microchannel 710. For example, each reactive distillation stage (770, 770a, 770b) can be operated at a different temperature, if desired.

The microchannel distillation unit 700A illustrated in FIG. 13 is identical in design and operation to the microchannel distillation unit 700 illustrated in FIG. 12 with the exception that in the microchannel distillation unit 700A the heat exchange fluid flows through the heat exchange channels 750 in a direction that is cross-current to the flow of the vapor phase through the process microchannel 710.

Although only one repeating unit (600, 700, 700A) is illustrated in FIGS. 11A-13, there is practically no upper limit to the number of reactive distillation units that may be used in microchannel reactor 500. For example, one, two, three, four, five, six, eight, ten, twenty, fifty, one hundred, hundreds, one thousand, thousands, ten thousand, tens of thousands, one hundred thousand, hundreds of thousands, millions, etc., of the repeating units described above may be used. The process microchannels, and associated liquid channels and heat exchange channels may be aligned side-by-side or stacked one above another. Although the reactive distillation units (600, 700, 700A) depict vertical flow through the channels, these reactive distillation units may be aligned horizontally to provide for horizontal flow through the channels, or they may be aligned at an inclined angle from the horizontal.

Each of the process microchannels (610, 710) may have a cross section that has any configuration, for example, square, rectangular, circular, oval, trapezoidal, etc. Each of these process microchannels has at least one internal dimension of height or width of up to about 10 mm, and in one embodiment from about 0.05 to about 10 mm, and in one embodiment about 0.001 to about 5 mm, and in one embodiment about 0.05 to about 2 mm, and in one embodiment about 0.05 to about 1.5 mm, and in one embodiment about 0.05 to about 1 mm, and in one embodiment about 0.05 to about 0.5 mm. The other internal dimension of height or width may be of any value, for example, it may range from about 0.01 cm to about 2 cm, and in one embodiment from about 0.01 to about 1 cm, and in one embodiment from about 0.1 to about 1 cm. The length of each of the process microchannels (610, 710) may be of any value, for example, it may range from about 1 to about 200 cm, and in one embodiment about 1 to about 50 cm, and in one embodiment about 2 to about 10 cm.

The height of each microchannel distillation stage (770, 770a, 770b) from one capture structure (772, 772a, 772b) to the next capture structure (for example, from capture structure 772 to capture structure 772a) may range from about 2 to about 100 mm, and in one embodiment from about 2 to about 75 mm, and in one embodiment from about 2 to about 50 mm, and in one embodiment from about 2 to about 25 mm, and in one embodiment from about 5 to about 10 mm.

The catalyst-containing wall (771, 771a, 771b) may comprise any of the catalytic materials described above. The catalyst may be in the form of a deposit or coating on sidewall 719. The side wall 719 and/or catalyst may comprise a material or structure that enhances the adherence of the liquid phase to the side wall and/or catalyst as it flows along the internal wall as a thin film. The side wall 719 may be made of stainless steel. The thickness of the catalytic deposit or coating on the side wall 719 may be in the range from about 0.1 to about 100 microns, and in one embodiment about 0.1 to about 50 microns, and in one embodiment about 0.1 to about 20 microns, and in one embodiment about 0.1 to about 10 microns. The thin film flowing along the catalyst-containing wall, as indicated by arrows 773, 773a and 773b, may have a thickness of about 0.1 to about 500 microns, and in one embodiment about 0.5 to about 200 microns, and in one embodiment about 1 to about 50 microns.

The capture structure (772, 772a, 772b) may be any structure that permits the flow of vapor through the capture structure and assists in the movement of liquid contacting the capture structure to and through the liquid exits (774, 774a, 774b) to the wicking region 732. The capture structure can be in the form of a wire mesh screen or cones that project from the liquid exits (774, 774a, 774b). The capture structure may be in the form of inverted cones, liquid-nonwetting porous structures having a pore size gradient with pore sizes getting larger toward the wicking region 732, liquid-wetting porous structures having a pore size gradient with pore sizes getting smaller toward the wicking region 732, and fibers such as found in demisters or filter media. Mechanisms for capturing dispersed liquid particles include impingement (due to flow around obstructions), Brownian capture (long residence time in high surface area structure), gravity, centrifugal forces (high curvature in flow), or incorporating fields, such as electrical or sonic fields, to induce aerosol particle motion relative to the flow field.

Another use for the capture structure (772, 772a, 772b) may be to enhance heat transfer. If the capture structure has a high thermal conductivity, it can act as an extended surface for heat transfer. By being in thermal contact with heat exchange channel 750, the capture structure (772, 772a, 772b) promotes heat transfer between the heat exchange channel and the flowing liquid and vapor phases in the process microchannel 710.

In one embodiment, the capture structure (772, 772a, 772b) may be a perforated foil in the form of expanded tetrahedrally configured filaments. Examples include Delker expanded screens such as 10 AL 16-125 P and 5 Cu 14-125 P. These screens can have one or two orders of magnitude higher permeability than conventional woven screens. In addition, aluminum, copper, and other metal forms of these screens have relatively high thermal conductivities and also enhance heat transfer.

The liquid channel 730 may be a microchannel although it may have larger dimensions that would not characterize it as a microchannel. Each of these channels may have a cross section that has any configuration, for example, square, rectangular, circular, oval, trapezoidal, etc. Each channel may have an internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may range from about 1 mm to about 100 mm, and in one embodiment about 5 mm to about 50 mm, and in one embodiment about 10 mm to about 20 mm. The length of the liquid channel 730 may range from about 1 cm to about 200 cm, and in one embodiment about 1 cm to about 50 cm, and in one embodiment from about 2 cm to about 10 cm. The separation between each process microchannel 710 and the next adjacent liquid channel 730 may range from about 0.05 mm to about 5 mm, and in one embodiment about 0.2 mm to about 2 mm.

The wicking region 732 may be made of a wicking material that preferentially retains a liquid by capillary forces and in which there are multiple continuous channels through which liquids may travel by capillary flow. The channels may be regularly or irregularly shaped. Liquid will migrate through a dry wick, while liquid in a liquid-containing wick can be transported by gravitational force or by applying a pressure differential, such as suction, to a part or parts of the wick. The capillary pore size in the wicking material can be selected based on the contact angle of the liquid, the intended pressure gradient within the liquid channel 730, and the surface tension of the liquid.

The wicking region 732 can be made of different materials depending on the liquid that is intended to be transported through the wicking region 732. The wicking material may be a uniform material, a mixture of materials, a composite material, or a gradient material. For example, the wicking material may be graded by pore size or wettability to help drain liquid in a desired direction. Examples of wicking materials that may be used include: sintered metals, metal screens, metal foams, polymer fibers including cellulosic fibers, as well as other wetting porous materials. The capillary pore sizes in the wicking materials may be in the range of about 10 nm to about 1 mm, and in one embodiment about 100 nm to about 0.1 mm, where these sizes are the largest pore diameters in the cross-section of the wicking material observed by scanning electron microscopy (SEM). In one embodiment, the wicking region 732 is, or includes, a microchannel structure. Liquid in the microchannels migrates by capillary flow. The microchannels may be of any length and may have a depth of about 1 to about 1000 microns, and in one embodiment about 10 to about 500 microns. The microchannels may have a width of about 1 to about 1000 microns, and in one embodiment about 10 to about 100 microns. In one embodiment, the microchannels are microgrooves, that is, microchannels having a constant or decreasing width from the top to the bottom of the groove. In one embodiment, the microchannels form the mouth to a larger diameter pore for liquid transport.

In operation, the wicking region 732 should not be dry. A wet or saturated wick may be used to effectively transport liquid through capillary to a low pressure zone, such as low pressure created by suction.

Punctured and punctured/expanded foils may be used as the wicking material in the wicking region 732 and/or as the capture structures (772, 772a, 772b). Useful foils include Ultra Thin MicroGrid Precision-Expanded Foils, available from Delker Corporation. These materials are made in a flattened form and a three-dimensional expanded form. Although similar to conventional wire mesh screens, these materials are made from a single thin sheet by punching an array of holes while pulling the material. In the flattened form the holes are an array of diamonds. In the expanded form, the filaments are in a regular tetrahedral configuration. These materials can be made in thicknesses as small as about 0.0015 inch (1.5 mil) and from a variety of metals, including copper, aluminum and nickel.

Fresnel lenses may be used as the wicking material. Wicks that have microchannels having depths of less than about 100 microns, and in one embodiment about 50 to about 100 microns may be used to promote rapid mass transfer.

The wicking region 732 may be prepared by laser machining grooves into a ceramic tape in the green state. These wicks can be made, for example, with grooves less than 50 microns deep with openings less than 100 microns wide. These grooves typically have a rectangular shape. Ceramic wicks have a high surface energy, are chemically inert, and have high temperature stability. Another material that may be used is an intermetallic formed from two or more metals placed in intimate contact during a bonding process and which combine to form an alloy, compound, or metal solution. Useful intermetallics have properties similar to the ceramic materials. An advantage of engineered structures is fine control of the length-scale for mass transfer in the liquid phase which is desirable for distillation.

The wicking region 732 should not be permitted to dry out during operation since this could result in vapor escaping through the wicking region. One approach for avoiding dry-out is to add a flow restriction in capillary contact with the wick structure, such as a porous structure with a smaller pore size than the wick structure and limiting the magnitude of the suction pressure such that the non-wetting phase(s) cannot displace the wetting phase from the flow restriction. This type of flow restriction may be referred to as a pore throat. In one embodiment, a pore throat may be provided between the wicking region 732 and the liquid exits (774, 774a, 774b) and/or liquid entrances (776, 776a, 776b).

The heat exchange channels (750) may be microchannels although they may have larger dimensions that would not characterize them as microchannels. Each of the heat exchange channels may have an internal dimension of height or width of up to about 10 mm, and in one embodiment about 0.05 to about 10 mm, and in one embodiment about 0.05 to about 5 mm, and in one embodiment from about 0.05 to about 2 mm, and in one embodiment from about 0.5 to about 1 mm. The other internal dimension may be of any value, for example, from about 1 mm to about 50 cm, and in one embodiment about 1 mm to about 10 cm, and in one embodiment about 5 mm to about 5 cm. The length of the heat exchange channels may be of any value, for example, from about 1 cm to about 200 cm, and in one embodiment about 1 cm to about 50 cm. The separation between each process microchannel 710 or liquid channel 730 and the next adjacent heat exchange channel 750 may range from about 0.05 mm to about 5 mm, and in one embodiment about 0.2 mm to about 2 mm.

In one embodiment, the process microchannels 710, liquid channels 730, and heat exchange channels 750 have rectangular cross sections and are aligned in side-by-side vertically oriented interleaved planes or horizontally oriented interleaved stacked planes. These planes can be tilted at an inclined angle from the horizontal. These configurations may be referred to as parallel plate configurations. An array of these rectangular channels can be easily arranged in a compact unit for scale-up.

The flow rate of the vapor phase flowing through the process microchannels 710 may range from about 0.001 to about 5 liters per minute (lpm), and in one embodiment about 0.01 to about 2 lpm, and in one embodiment about 0.01 to about 1 lpm. The velocity of the vapor phase flowing through the process microchannels 710 may range from about 0.01 to about 500 meters per second (m/s), and in one embodiment about 0.01 to about 100 m/s, and in one embodiment about 0.1 to about 50 m/s. The Reynolds Number for the vapor phase flowing through the process microchannels 710 may range from about 100 to about 50,000, and in one embodiment about 100 to about 5,000. The gage pressure within the process microchannels 710 may be in the range from about 0.01 to about 1,000 atmospheres, and in one embodiment about 0.01 to about 100 atmospheres.

The flow rate of the liquid phase flowing as a thin film in the microchannel distillation stages (770, 770a, 770b) may range from about 0.001 to about 10 lpm, and in one embodiment from about 0.001 to about 5 lpm, and in one embodiment from about 0.001 to about 2 lpm, and in one embodiment from about 0.001 to about 1 lpm, and in one embodiment about 0.001 to about 0.1 lpm. The velocity of the thin film flowing in the distillation stages may range from about 0.001 to about 5 m/s, and in one embodiment about 0.001 to about 2 m/s, and in one embodiment about 0.01 to about 1 m/s. The Reynolds Number for the thin film flowing in the distillation stages may range from about 1 to about 1,000 and in one embodiment about 1 to about 200, wherein the hydraulic diameter of the thin film is defined as the average film thickness.

The flow rate of the liquid phase flowing through the wicking region 732 in the liquid channels 730, may range from about 0.0001 to about 1 lpm, and in one embodiment about 0.001 to about 0.1 lpm. The velocity of the liquid phase flowing through the liquid channels 730 may range from about 0.0001 to about 0.5 m/s, and in one embodiment about 0.0001 m/s to about 0.2 m/s. The Reynolds Number for the liquid phase flowing through the liquid channels 730 may range from about 10 to about 5,000 and in one embodiment about 10 to about 2,500. The gage pressure within the wicking region 732 in the liquid channels 730 may be in the range from about 0.01 to about 1,000 atmospheres, and in one embodiment about 0.01 to about 200 atmospheres. The pressure differential across the wicking region 732 may range from about 0.0001 to about 0.01 atmosphere, and in one embodiment about 0.0001 to about 0.005 atmosphere.

The heat exchange fluid entering the heat exchange channels 750 may have a temperature in the range from about −150° C. to about 400° C., and in one embodiment from about −100° C. to about 300° C. The heat exchange fluid exiting the heat exchange channels 750 may have a temperature in the range from about −100° C. to about 300° C., and in one embodiment from about −50° C. to about 250° C. The pressure drop for the heat exchange fluid as it flows through the heat exchange channels may range from about 0.0001 to about 5 atmospheres per meter of length of the heat exchange channel (atm/m), and in one embodiment from about 0.001 to about 1 atm/m. The Reynolds Number for the flow of heat exchange fluid flowing through the heat exchange channels may be in the range of about 10 to about 100,000, and in one embodiment about 200 to about 10,000.

The conversion of the reactant substrate may be about 30% or higher per cycle, and in one embodiment about 50% or higher, and in one embodiment about 90% or higher per cycle.

The conversion of alkylating and/or acylating agent may be about 80% or higher per cycle, and in one embodiment about 90% or higher, and in one embodiment about 99% or higher per cycle.

The yield of alkylation product and/or acylation product may be about 60% or higher per cycle, and in one embodiment about 70% or higher, and in one embodiment about 90% or higher per cycle.

While the invention has been explained in relation to various embodiments, it is to be understood that various modifications thereof will become apparent to those skilled in the art upon reading the specification. Therefore, it is to be understood that the invention disclosed herein is intended to cover such modifications as fall within the scope of the appended claims.

The invention claimed is:

1. A process for conducting an alkylation or acylation reaction in a microchannel reactor, the microchannel reactor comprising a microchannel reactor core comprising a plurality of process microchannels and a feed stream header for distributing a reactant mixture to the process microchannels, the feed stream header comprising a first reactant zone, a second reactant zone, and an apertured section positioned between the first reactant zone and the second reactant zone, the process comprising:
flowing a first reactant feed stream into the first reactant zone, flowing a second reactant feed stream through the second reactant zone and the apertured section into the first reactant zone where it is mixed with the first reactant feed stream to form a reactant mixture, the reactant mixture comprising a dispersed phase of the second reactant feed stream and a continuous phase of the first reactant feed stream,
the dispersed phase being in the form of gas bubbles and/or liquid droplets dispersed in the continuous phase, the reactant mixture comprising a reactant substrate, and an alkylating agent, an acylating agent or a mixture thereof, and
flowing the reactant mixture from the feed stream header into the process microchannels, and reacting the reactant substrate with the alkylating agent, acylating agent, or mixture thereof in the presence of a catalyst in the process microchannels at a temperature in the range from about 100° C. to about 500° C. to form a product comprising at least one alkylation product, at least one acylation product, or a mixture thereof, the weight hourly space velocity for the flow of reactants in the microchannel reactor core being at least about 100 milliliters of feed per gram of catalyst per hour;
transferring heat from the process microchannels to a heat sink; and
removing the product from the process microchannels.

2. The process of claim 1 wherein the catalyst is in the form of a liquid.

3. The process of claim 2 wherein the catalyst is mixed with the first reactant feed stream.

4. The process of claim 2 wherein the catalyst is mixed with the second reactant feed stream.

5. The process of claim 2 wherein the first reactant feed stream and the second reactant feed stream are mixed with the catalyst prior to entering the process microchannels.

6. The process of claim 1 wherein the process microchannels have internal dimensions of width or height of up to about 10 mm.

7. The process of claim 1 wherein the process microchannels have internal dimensions of width or height of up to about 2 mm.

8. The process of claim 1 wherein the process microchannels are made of a material comprising: steel; monel; inconel; aluminum; titanium; nickel; copper; brass; an alloy of any of the foregoing metals; a polymer; ceramics; glass; a composite comprising a polymer and fiberglass; quartz; silicon; or a combination of two or more thereof.

9. The process of claim 1 wherein the heat sink is adjacent to the process microchannels.

10. The process of claim 1 wherein the heat sink is remote from the process microchannels.

11. The process of claim 1 wherein the heat sink comprises at least one heat exchange channel.

12. The process of claim 11 wherein the heat exchange channel comprises a microchannel.

13. The process of claim 11 wherein the heat exchange channel has an internal dimension of width or height of up to about 10 mm.

14. The process of claim 11 wherein the heat exchange channel has an internal dimension of width or height of up to about 2 mm.

15. The process of claim 11 wherein the heat exchange channel is made of a material comprising: steel; monel; inconel; aluminum; titanium; nickel; copper; brass; an alloy of any of the foregoing metals; a polymer; ceramics; glass; a composite comprising polymer and fiberglass; quartz; silicon; or a combination of two or more thereof.

16. The process of claim 1 wherein the heat sink comprises one or more non-fluid cooling elements.

17. The process of claim 16 wherein the non-fluid cooling element is adjacent to the process microchannels.

18. The process of claim 16 wherein each process microchannel comprises one or more walls and the non-fluid cooling element is built into at least one of the walls of the process microchannels.

19. The process of claim 16 wherein each process microchannel comprises one or more walls and at least one of the walls of the process microchannel is formed from the non-fluid cooling element.

20. The process of claim 1 wherein the first reactant feed stream comprises one or more of an aliphatic compound, an aromatic compound, an aliphatic-substituted aromatic compound, an aromatic-substituted aliphatic compound, a hydrocarbon compound containing non-hydrocarbon groups, a hetero substituted hydrocarbon compound, or a mixture of two or more thereof.

21. The process of claim 1 wherein the first reactant feed stream comprises at least one aliphatic compound.

22. The process of claim 1 wherein the first reactant feed stream comprises at least one aromatic compound.

23. The process of claim 1 wherein the first reactant feed stream comprises at least one alkane and/or isoalkane.

24. The process of claim 1 wherein the first reactant feed stream comprises one or more polymers.

25. The process of claim 24 wherein the polymer is derived from one or more monomers containing 2 to about 12 carbon atoms.

26. The process of claim 1 wherein the first reactant feed stream comprises one or more of isobutane, isopentane, isohexane, 2-methyl butane, 2-methyl pentane and 3-methyl pentane.

27. The process of claim 1 wherein the first reactant feed stream comprises one or more of benzene, toluene, ethylbenzene, propylbenzene, xylene, mesitylene, methylethylbenzene, naphthalene, anthracene, phenanthrene, methylnaphthalene, dimethylnaphthalene and tetralin.

28. The process of claim 1 wherein the first reactant feed stream comprises one or more of phenol, benzene diol, naphthol and naphthalene diol.

29. The process of claim 1 wherein the first reactant feed stream comprises at least one aromatic amine, at least one pyridine, or a mixture thereof.

30. The process of claim 1 wherein the first reactant feed stream comprises one or more of aniline, toluidine, phenylene diamine and toluene diamine.

31. The process of claim 1 wherein the first reactant feed stream comprises one or more of o-xylene, m-xylene, p-xylene, toluene, tolyl aldehyde, amino toluene, o-cresol, m-cresol, p-cresol and phenyl aldehyde.

32. The process of claim 1 wherein the second reactant feed stream comprises an olefin containing from 2 to about 30 carbon atoms.

33. The process of claim 1 wherein the second reactant feed stream comprises an olefin containing from about 10 to about 18 carbon atoms.

34. The process of claim 1 wherein the second reactant feed stream comprises one or more of ethylene, propylene, butene-1, cis-butene-2, trans-butene-2, isobutylene, 1,3-butadiene, amylene, isoamylene, 2-pentene, 2-methyl-butene-2,1-pentene, 3-methyl-butene-1, 2-methyl-butene-1, isoprene, piperylene, cyclopentene, 1-hexene, 2-methyl-1-pentene, 2-methyl-2-pentene, 1-octene, diisobutylene, 1-decene, 1-dodecene, 2-dodecene, 1-tetradecene, 2-tetradecene, 1-hexadecene, 1-eicosene, α-pinene, camphene, limonene, and styrene.

35. The process of claim 1 wherein the second reactant feed stream comprises one or more of ethylene, propylene, butylene, isobutylene, and amylene.

36. The process of claim 1 wherein the product comprises one or more of ethylbenzene, $C_{10}$-$C_{18}$ alkyl benzene, cumene, cymene, refinery alkylate, detergent alkylate, and xylene.

37. The process of claim 1 wherein the product comprises an alkylated phenol, alkylated phenol derivative, or a mixture thereof.

38. The process of claim 1 wherein the product comprises an alkylated aromatic amine, an alkylated pyridene, or a mixture thereof.

39. The process of claim 1 wherein the product comprises one or more of dimethyl pentane, trimethyl pentane, 2,6-xylenol, o-cresol, and 5-tert-butyl-2,4-toluene diamine.

40. The process of claim 1 wherein the product comprises bisphenol A.

41. The process of claim 1 wherein the product comprises hydrocarbyl substituted carboxylic acid or anhydride.

42. The process of claim 11 wherein the process microchannels exchange heat with a heat exchange fluid flowing through the heat exchange channel.

43. The process of claim 42 wherein the heat exchange fluid undergoes a phase change as it flows through the heat exchange channel.

44. The process of claim 42 wherein the heat flux between the heat exchange channel and the process microchannels is in the range from about 0.01 to about 250 watts per square centimeter of surface area of the process microchannels.

45. The process of claim 11 wherein an endothermic process is conducted in the heat exchange channel.

46. The process of claim 45 wherein the endothermic process comprises a steam reforming reaction or a dehydrogenation reaction.

47. The process of claim 11 wherein the first reactant feed stream flows through the process microchannels in a first direction, and a heat exchange fluid flows through the heat exchange channel in a second direction, the second direction being cross current relative to the first direction.

48. The process of claim 11 wherein the first reactant feed stream flows through the process microchannels in a first direction, and a heat exchange fluid flows through the heat exchange channel in a second direction, the second direction being concurrent or counter current relative to the first direction.

49. The process of claim 11 wherein a heat exchange fluid flows through the heat exchange channel, the heat exchange fluid comprising the first reactant feed stream, the second reactant feed stream, or a mixture thereof.

50. The process of claim 11 wherein a heat exchange fluid flows through the heat exchange channel, the heat exchange fluid comprising one or more of air, steam, liquid water, carbon monoxide, carbon dioxide, gaseous nitrogen, liquid nitrogen, inert gas, gaseous hydrocarbon, oil, and liquid hydrocarbon.

51. The process of claim 1 wherein the apertured section comprises a relatively thin sheet overlying a relatively thick sheet or plate, the relatively thin sheet containing an array of relatively small apertures, and the relatively thick sheet or plate containing an array of relatively large apertures, at least some of the relatively small apertures being aligned with the relatively large apertures.

52. The process of claim 1 wherein the apertured section comprises apertures that are partially filled with a coating material.

53. The process of claim 1 wherein the apertured section is heat treated.

54. The process of claim 1 wherein the apertured section is made from a porous material.

55. The process of claim 54 wherein the porous material is metallic.

56. The process of claim 54 wherein the porous material is nonmetallic.

57. The process of claim 54 wherein the porous material is oxidized.

58. The process of claim 54 wherein the porous material is coated with alumina or nickel.

59. The process of claim 1 wherein the apertured section is made from a porous material, the surface of the porous material being treated by filling the pores on the surface with a liquid filler, solidifying the filler, grinding or polishing the surface, and removing the filler.

60. The process of claim 1 wherein the catalyst comprises a liquid catalyst.

61. The process of claim 1 wherein the catalyst comprises a solid catalyst.

62. The process of claim 1 wherein the catalyst comprises an acid catalyst.

63. The process of claim 1 wherein the catalyst comprises is a Friedel-Crafts catalyst.

64. The process of claim 1 wherein the catalyst comprises alumino-silicate, clay, ion-exchange resin, mixed oxide or supported acid.

65. The process of claim 1 wherein the catalyst comprises a zeolite.

66. The process of claim 1 wherein the catalyst comprises a hydrogenating metal component and a solid acid constituent.

67. The process of claim 1 wherein the catalyst comprises particulate solids.

68. The process of claim 1 wherein the catalyst is washcoated on interior walls of the process microchannel, grown on interior walls of the process microchannel from solution, or coated in situ on a fin structure.

69. The process of claim 1 wherein the catalyst comprises a support, an optional buffer layer overlying the support, an interfacial layer overlying the optional buffer layer or the support, and a catalyst material dispersed or deposited on the interfacial layer.

70. The process of claim 1 wherein the catalyst is supported by a support, the support being made of a material comprising one or more of silica gel, foamed copper, sintered stainless steel fiber, steel wool, alumina, poly(methyl methacrylate), polysulfonate, poly(tetrafluoroethylene), iron, nickel sponge, nylon, polyvinylidene difluoride, polypropylene, polyethylene, polyethylene ethylketone, polyvinyl alcohol, polyvinyl acetate, polyacrylate, polymethylmethacrylate, polystyrene, polyphenylene sulfide, polysulfone, polybutylene, or a combination of two or more thereof.

71. The process of claim 1 wherein the catalyst is supported on a support, the support comprising a heat conducting material.

72. The process of claim 1 wherein the catalyst is supported on a support, the support comprising an alloy comprising Ni, Cr and Fe, or an alloy comprising Fe, Cr, Al and Y.

73. The process of claim 1 wherein the catalyst is supported on a support having a flow-by configuration, a flow-through configuration, a honeycomb structure or a serpentine configuration.

74. The process of claim 1 wherein the catalyst is supported on a support having the configuration of a foam, felt, wad, fin, or a combination of two or more thereof.

75. The process of claim 1 wherein the catalyst is supported on a support having a flow-by configuration with an adjacent gap, a foam configuration with an adjacent gap, a fin structure with gaps, a washcoat on a substrate, or a gauze configuration with a gap for flow.

76. The process of claim 1 wherein the catalyst is supported on a support, the support comprising a fin assembly comprising at least one fin.

77. The process of claim 76 wherein the fin assembly comprises a plurality of parallel spaced fins.

78. The process of claim 76 wherein the fin has an exterior surface and a porous material overlies at least part of the exterior surface of the fin, the catalyst being supported by the porous material.

79. The process of claim 78 wherein the porous material comprises a coating, fibers, foam or felt.

80. The process of claim 76 wherein the fin has an exterior surface and a plurality fibers or protrusions extend from at least part of the exterior surface of the fin, the catalyst being supported by the protrusions.

81. The process of claim 76 wherein the fin has an exterior surface and the catalyst is: washcoated on at least part of the exterior surface of the fin; grown on at least part of the exterior surface of the fin from solution; or deposited on at least part of the exterior surface of the fin using vapor deposition.

82. The process of claim 76 wherein the fin assembly comprises a plurality of parallel spaced fins, at least one of the fins having a length that is different than the length of the other fins.

83. The process of claim 76 wherein the fin assembly comprises a plurality of parallel spaced fins, at least one of the fins having a height that is different than the height of the other fins.

84. The process of claim 76 wherein the fin has a cross section having the shape of a square, a rectangle, or a trapezoid.

85. The process of claim 76 wherein the fin is made of a material comprising: steel; aluminum; titanium; iron; nickel; platinum; rhodium; copper;
chromium; brass; an alloy of any of the foregoing metals; a polymer; ceramics; glass; a composite comprising polymer and fiberglass; quartz; silicon; or a combination of two or more thereof.

86. The process of claim 76 wherein the fin is made of an alloy comprising Ni, Cr and Fe, or an alloy comprising Fe, Cr, Al and Y.

87. The process of claim 76 wherein the fin is made of an $Al_2O_3$ forming material or a $Cr_2O_3$ forming material.

88. The process of claim 1 wherein the catalyst is in the form of a layer of ZSM-5 zeolite having a thickness of up to about 1 micron.

89. The process of claim 1 wherein the catalyst is positioned within a reaction zone in each process microchannel, the reaction zone having a bulk flow path comprising about 5% to about 95% of the cross section of the process microchannel.

90. The process of claim 1 wherein the contact time for the first reactant feed stream, second reactant feed stream and product with the catalyst is in the range up to about 10 minutes.

91. The process of claim 1 wherein the temperature within each process microchannel is in the range from about 100° C. to about 400° C.

92. The process of claim 1 wherein the gage pressure within each process microchannel is in the range up to about 50 atmospheres.

93. The process of claim 1 wherein the weight hourly space velocity for the flow of reactants through the microchannel reactor core is in the range from about 100 to about 1,000,000 milliliters of feed per gram of catalyst per hour.

94. The process of claim 1 wherein the pressure drop for the flow of reactants and product through the process microchannels is up to about 0.5 atmosphere per meter of length of the process microchannels.

95. The process of claim 11 wherein a heat exchange fluid flows through the heat exchange channel, the pressure drop for the heat exchange fluid flowing through the heat exchange channel being up to about 0.5 atmosphere per meter of length of the heat exchange channel.

96. The process of claim 1 wherein the conversion of the reactant substrate is about 30% or higher per cycle.

97. The process of claim 1 wherein the conversion of the alkylating and/or acylating agent is about 80% or higher per cycle.

98. The process of claim 1 wherein the yield of product is about 60% or higher per cycle.

99. The process of claim 1 wherein subsequent to removing the product from the process microchannels, the process further comprises flowing a regenerating fluid through the process microchannels in contact with the catalyst, the residence time for the regenerating fluid in the process microchannels being from about 0.001 to about 10 seconds.

100. The process of claim 1 wherein each process microchannel comprises surface features formed in and/or on one or more interior walls for modifying flow and/or enhancing mixing within the process microchannel.

101. The process of claim 11 wherein the heat exchange channel comprises surface features formed in and/or on one or more interior walls for modifying flow and/or enhancing mixing within the heat exchange channel.

102. The process of claim 100 wherein the surface features are in the form of depressions in and/or projections from one or more of the microchannel interior walls and are oriented at angles relative to the direction of flow of fluid through the process microchannel.

103. The process of claim 100 wherein the surface features comprise two or more layers stacked on top of each other and/or intertwined in a three-dimensional pattern.

104. The process of claim 100 wherein the surface features are in the form of circles, oblongs, squares, rectangles, checks, chevrons, wavy shapes, or combinations thereof.

105. The process of claim 100 wherein the surface features comprise sub-features where the major walls of the surface features further contain smaller surface features in the form of notches, waves, indents, holes, burrs, checks, scallops, or combinations thereof.

* * * * *